(12) United States Patent
Thakkar et al.

(10) Patent No.: US 11,771,900 B2
(45) Date of Patent: Oct. 3, 2023

(54) CIRCUITRY FOR MEDICAL STIMULATION SYSTEMS

(71) Applicant: Lungpacer Medical Inc., Vancouver (CA)

(72) Inventors: Viral S. Thakkar, Chester Springs, PA (US); Douglas G. Evans, Downingtown, PA (US)

(73) Assignee: Lungpacer Medical Inc., Burnaby (CA)

( * ) Notice: Subject to any disclaimer, the term of this patent is extended or adjusted under 35 U.S.C. 154(b) by 243 days.

(21) Appl. No.: 16/898,157

(22) Filed: Jun. 10, 2020

(65) Prior Publication Data

US 2020/0391027 A1 Dec. 17, 2020

Related U.S. Application Data

(60) Provisional application No. 62/860,452, filed on Jun. 12, 2019.

(51) Int. Cl.
| | |
|---|---|
| *A61N 1/36* | (2006.01) |
| *A61N 1/05* | (2006.01) |
| *A61N 1/04* | (2006.01) |

(52) U.S. Cl.
CPC .......... *A61N 1/3611* (2013.01); *A61N 1/0452* (2013.01); *A61N 1/0456* (2013.01);
(Continued)

(58) Field of Classification Search
CPC ............................ A61N 1/3611; A61N 1/0452
(Continued)

(56) References Cited

U.S. PATENT DOCUMENTS

| | | | |
|---|---|---|---|
| 1,693,734 A | 12/1928 | Waggoner | |
| 2,532,788 A | 12/1950 | Sarnoff | |

(Continued)

FOREIGN PATENT DOCUMENTS

| | | |
|---|---|---|
| CN | 1652839 A | 8/2005 |
| CN | 102143781 A | 8/2011 |

(Continued)

OTHER PUBLICATIONS

International Search Report in International Application No. PCT/US2020/037017, dated Sep. 24, 2020 (3 pages).

(Continued)

*Primary Examiner* — Nicole F Lavert
(74) *Attorney, Agent, or Firm* — Bookoff McAndrews, PLLC

(57) ABSTRACT

A medical device that includes a flexible body having a proximal end and a distal end, and an electrode positioned on the body proximate the distal end. The electrode is configured to provide an electrical charge for stimulating tissue. The medical device includes an electrical connection positioned on the body proximate the proximal end. The electrical connection is configured to electrically couple the electrode to a power source. The medical device includes an electrical lead connecting the electrode to the electrical connection. The lead is on or in the flexible body. The body is configured to have a first configuration prior to being secured to an exterior of a tube and a second configuration having a shape that conforms to a profile of the tube with the electrode secured to an exterior of the tube.

20 Claims, 19 Drawing Sheets

(52) U.S. Cl.
CPC .............. *A61N 1/0476* (2013.01); *A61N 1/05* (2013.01); *A61N 1/3601* (2013.01)

(58) Field of Classification Search
USPC .......................................................... 607/42
See application file for complete search history.

(56) References Cited

U.S. PATENT DOCUMENTS

| | | |
|---|---|---|
| 2,664,880 A | 1/1954 | Wales, Jr. |
| 3,348,548 A | 10/1967 | Chardack |
| 3,470,876 A | 10/1969 | John |
| 3,769,984 A | 11/1973 | Muench |
| 3,804,098 A | 4/1974 | Friedman |
| 3,817,241 A | 6/1974 | Grausz |
| 3,835,864 A | 9/1974 | Rasor et al. |
| 3,847,157 A | 11/1974 | Caillouette et al. |
| 3,851,641 A | 12/1974 | Toole et al. |
| 3,896,373 A | 7/1975 | Zelby |
| 3,938,502 A | 2/1976 | Bom |
| 3,983,881 A | 10/1976 | Wickham |
| 4,054,881 A | 10/1977 | Raab |
| 4,072,146 A | 2/1978 | Howes |
| 4,114,601 A | 9/1978 | Abels |
| 4,143,872 A | 3/1979 | Havstad et al. |
| 4,173,228 A | 11/1979 | Childress et al. |
| 4,249,539 A | 2/1981 | Mezrich et al. |
| 4,317,078 A | 2/1982 | Weed et al. |
| 4,380,237 A | 4/1983 | Newbower |
| 4,407,294 A | 10/1983 | Vilkomerson |
| 4,416,289 A | 11/1983 | Bresler |
| 4,431,005 A | 2/1984 | Mccormick |
| 4,431,006 A | 2/1984 | Trimmer et al. |
| 4,445,501 A | 5/1984 | Bresler |
| RE31,873 E | 4/1985 | Howes |
| 4,573,481 A | 3/1986 | Bullara |
| 4,586,923 A | 5/1986 | Gould et al. |
| 4,587,975 A | 5/1986 | Salo et al. |
| 4,643,201 A | 2/1987 | Stokes |
| 4,674,518 A | 6/1987 | Salo |
| 4,681,117 A | 7/1987 | Brodman et al. |
| 4,683,890 A | 8/1987 | Hewson |
| 4,697,595 A | 10/1987 | Breyer et al. |
| 4,706,681 A | 11/1987 | Breyer et al. |
| 4,771,788 A | 9/1988 | Millar |
| 4,819,662 A | 4/1989 | Heil, Jr. et al. |
| 4,827,935 A | 5/1989 | Geddes et al. |
| 4,830,008 A | 5/1989 | Meer |
| 4,840,182 A | 6/1989 | Carlson |
| 4,852,580 A | 8/1989 | Wood |
| 4,860,769 A | 8/1989 | Fogarty et al. |
| 4,905,698 A | 3/1990 | Strohl, Jr. et al. |
| 4,911,174 A | 3/1990 | Pederson et al. |
| 4,934,049 A | 6/1990 | Kiekhafer et al. |
| 4,944,088 A | 7/1990 | Doan et al. |
| 4,951,682 A | 8/1990 | Petre |
| 4,957,110 A | 9/1990 | Vogel et al. |
| 4,989,617 A | 2/1991 | Memberg et al. |
| 5,005,587 A | 4/1991 | Scott |
| 5,036,848 A | 8/1991 | Hewson |
| 5,042,143 A | 8/1991 | Holleman et al. |
| 5,056,519 A | 10/1991 | Vince |
| 5,115,818 A | 5/1992 | Holleman et al. |
| 5,146,918 A | 9/1992 | Kallok et al. |
| 5,170,802 A | 12/1992 | Mehra |
| 5,184,621 A | 2/1993 | Vogel et al. |
| 5,224,491 A | 7/1993 | Mehra |
| 5,243,995 A | 9/1993 | Maier |
| 5,265,604 A | 11/1993 | Vince |
| 5,267,569 A | 12/1993 | Lienhard |
| 5,314,463 A | 5/1994 | Camps et al. |
| 5,316,009 A | 5/1994 | Yamada |
| 5,324,322 A | 6/1994 | Grill, Jr. et al. |
| 5,330,522 A | 7/1994 | Kreyenhagen |
| 5,345,936 A | 9/1994 | Pomeranz et al. |
| 5,383,923 A | 1/1995 | Webster, Jr. |
| 5,411,025 A | 5/1995 | Webster, Jr. |
| 5,417,208 A | 5/1995 | Winkler |
| 5,451,206 A | 9/1995 | Young |
| 5,456,254 A | 10/1995 | Pietroski et al. |
| 5,465,717 A | 11/1995 | Imran et al. |
| 5,476,498 A | 12/1995 | Ayers |
| 5,486,159 A | 1/1996 | Mahurkar |
| 5,507,725 A | 4/1996 | Savage et al. |
| 5,524,632 A | 6/1996 | Stein et al. |
| 5,527,358 A | 6/1996 | Mehmanesh et al. |
| 5,531,686 A | 7/1996 | Lundquist et al. |
| 5,549,655 A | 8/1996 | Erickson |
| 5,555,618 A | 9/1996 | Winkler |
| 5,567,724 A | 10/1996 | Kelleher et al. |
| 5,584,873 A | 12/1996 | Shoberg et al. |
| 5,604,231 A | 2/1997 | Smith et al. |
| 5,665,103 A | 9/1997 | Lafontaine et al. |
| 5,678,535 A | 10/1997 | Dimarco |
| 5,683,370 A | 11/1997 | Luther et al. |
| 5,709,853 A | 1/1998 | Iino et al. |
| 5,716,392 A | 2/1998 | Bourgeois et al. |
| 5,733,255 A | 3/1998 | Dinh et al. |
| 5,755,765 A | 5/1998 | Hyde et al. |
| 5,776,111 A | 7/1998 | Tesio |
| 5,779,732 A | 7/1998 | Amundson |
| 5,782,828 A | 7/1998 | Chen et al. |
| 5,785,706 A | 7/1998 | Bednarek |
| 5,788,681 A | 8/1998 | Weaver et al. |
| 5,813,399 A | 9/1998 | Isaza et al. |
| 5,814,086 A | 9/1998 | Hirschberg et al. |
| RE35,924 E | 10/1998 | Winkler |
| 5,824,027 A | 10/1998 | Hoffer et al. |
| 5,827,192 A | 10/1998 | Gopakumaran et al. |
| 5,916,163 A | 6/1999 | Panescu et al. |
| 5,944,022 A | 8/1999 | Nardella et al. |
| 5,954,761 A | 9/1999 | Machek et al. |
| 5,967,978 A | 10/1999 | Littmann et al. |
| 5,971,933 A | 10/1999 | Gopakumaran et al. |
| 5,983,126 A | 11/1999 | Wittkampf |
| 6,006,134 A | 12/1999 | Hill et al. |
| 6,024,702 A | 2/2000 | Iversen |
| 6,096,728 A | 8/2000 | Collins et al. |
| 6,120,476 A | 9/2000 | Fung et al. |
| 6,123,699 A | 9/2000 | Webster, Jr. |
| 6,126,649 A | 10/2000 | Vantassel et al. |
| 6,136,021 A | 10/2000 | Tockman et al. |
| 6,157,862 A | 12/2000 | Brownlee et al. |
| 6,161,029 A | 12/2000 | Spreigl et al. |
| 6,165,133 A | 12/2000 | Rapoport |
| 6,166,048 A | 12/2000 | Bencherif |
| 6,171,277 B1 | 1/2001 | Ponzi |
| 6,183,463 B1 | 2/2001 | Webster, Jr. |
| 6,198,970 B1 | 3/2001 | Freed et al. |
| 6,198,974 B1 | 3/2001 | Webster, Jr. |
| 6,201,994 B1 | 3/2001 | Warman et al. |
| 6,208,881 B1 | 3/2001 | Champeau |
| 6,210,339 B1 | 4/2001 | Kiepen et al. |
| 6,212,435 B1 | 4/2001 | Lattner et al. |
| 6,216,045 B1 | 4/2001 | Black et al. |
| 6,236,892 B1 | 5/2001 | Feler |
| 6,240,320 B1 | 5/2001 | Spehr et al. |
| 6,249,708 B1 | 6/2001 | Nelson et al. |
| 6,251,126 B1 | 6/2001 | Ottenhoff et al. |
| 6,269,269 B1 | 7/2001 | Ottenhoff et al. |
| 6,292,695 B1 | 9/2001 | Webster, Jr. et al. |
| 6,295,475 B1 | 9/2001 | Morgan |
| 6,360,740 B1 | 3/2002 | Ward et al. |
| 6,397,108 B1 | 5/2002 | Camps et al. |
| 6,400,976 B1 | 6/2002 | Champeau |
| 6,415,183 B1 | 7/2002 | Scheiner et al. |
| 6,415,187 B1 | 7/2002 | Kuzma et al. |
| 6,438,427 B1 | 8/2002 | Rexhausen et al. |
| 6,445,953 B1 | 9/2002 | Bulkes et al. |
| 6,449,507 B1 | 9/2002 | Hill et al. |
| 6,463,327 B1 | 10/2002 | Lurie et al. |
| 6,493,590 B1 | 12/2002 | Wessman et al. |
| 6,508,802 B1 | 1/2003 | Rosengart et al. |
| 6,526,321 B1 | 2/2003 | Spehr |
| 6,569,114 B2 | 5/2003 | Ponzi et al. |

(56) References Cited

U.S. PATENT DOCUMENTS

| | | |
|---|---|---|
| 6,584,362 B1 | 6/2003 | Scheiner et al. |
| 6,585,718 B2 | 7/2003 | Hayzelden et al. |
| 6,587,726 B2 | 7/2003 | Lurie et al. |
| 6,602,242 B1 | 8/2003 | Fung et al. |
| 6,610,713 B2 | 8/2003 | Tracey |
| 6,630,611 B1 | 10/2003 | Malowaniec |
| 6,643,552 B2 | 11/2003 | Edell et al. |
| 6,651,652 B1 | 11/2003 | Waard |
| 6,682,526 B1 | 1/2004 | Jones et al. |
| 6,702,780 B1 | 3/2004 | Gilboa et al. |
| 6,718,208 B2 | 4/2004 | Hill et al. |
| 6,721,603 B2 | 4/2004 | Zabara et al. |
| 6,757,970 B1 | 7/2004 | Kuzma et al. |
| 6,778,854 B2 | 8/2004 | Puskas |
| 6,779,257 B2 | 8/2004 | Kiepen et al. |
| 6,844,713 B2 | 1/2005 | Steber et al. |
| RE38,705 E | 2/2005 | Hill et al. |
| 6,881,211 B2 | 4/2005 | Schweikert et al. |
| 6,885,888 B2 | 4/2005 | Rezai |
| 6,907,285 B2 | 6/2005 | Denker et al. |
| 6,934,583 B2 | 8/2005 | Weinberg et al. |
| 6,981,314 B2 | 1/2006 | Black et al. |
| 6,999,820 B2 | 2/2006 | Jordan |
| 7,018,374 B2 | 3/2006 | Schon et al. |
| 7,047,627 B2 | 5/2006 | Black et al. |
| 7,071,194 B2 | 7/2006 | Teng |
| 7,072,720 B2 | 7/2006 | Puskas |
| 7,077,823 B2 | 7/2006 | McDaniel |
| 7,080,645 B2 | 7/2006 | Genger et al. |
| 7,082,331 B1 | 7/2006 | Park et al. |
| 7,130,700 B2 | 10/2006 | Gardeski et al. |
| 7,142,903 B2 | 11/2006 | Rodriguez et al. |
| 7,149,585 B2 | 12/2006 | Wessman et al. |
| 7,155,278 B2 | 12/2006 | King et al. |
| 7,167,751 B1 | 1/2007 | Whitehurst et al. |
| 7,168,429 B2 | 1/2007 | Matthews et al. |
| 7,184,829 B2 | 2/2007 | Hill et al. |
| 7,206,636 B1 | 4/2007 | Turcott |
| 7,212,867 B2 | 5/2007 | Van et al. |
| 7,225,016 B1 | 5/2007 | Koh |
| 7,225,019 B2 | 5/2007 | Jahns et al. |
| 7,229,429 B2 | 6/2007 | Martin et al. |
| 7,231,260 B2 | 6/2007 | Wallace et al. |
| 7,235,070 B2 | 6/2007 | Vanney |
| 7,269,459 B1 | 9/2007 | Koh |
| 7,277,757 B2 | 10/2007 | Casavant et al. |
| 7,283,875 B2 | 10/2007 | Larsson et al. |
| 7,340,302 B1 | 3/2008 | Falkenberg et al. |
| 7,363,085 B1 | 4/2008 | Benser et al. |
| 7,363,086 B1 | 4/2008 | Koh et al. |
| 7,371,220 B1 | 5/2008 | Koh et al. |
| 7,416,552 B2 | 8/2008 | Paul et al. |
| 7,421,296 B1 | 9/2008 | Benser et al. |
| 7,454,244 B2 | 11/2008 | Kassab et al. |
| 7,519,425 B2 | 4/2009 | Benser et al. |
| 7,519,426 B1 | 4/2009 | Koh et al. |
| 7,522,953 B2 | 4/2009 | Gharib et al. |
| 7,553,305 B2 | 6/2009 | Honebrink et al. |
| 7,555,349 B2 | 6/2009 | Wessman et al. |
| 7,569,029 B2 | 8/2009 | Clark et al. |
| 7,591,265 B2 | 9/2009 | Lee et al. |
| 7,593,760 B2 | 9/2009 | Rodriguez et al. |
| 7,613,524 B2 | 11/2009 | Jordan |
| 7,636,600 B1 | 12/2009 | Koh |
| 7,670,284 B2 | 3/2010 | Padget et al. |
| 7,672,728 B2 | 3/2010 | Libbus et al. |
| 7,672,729 B2 | 3/2010 | Koh et al. |
| 7,676,275 B1 | 3/2010 | Farazi et al. |
| 7,676,910 B2 | 3/2010 | Kiepen et al. |
| 7,697,984 B2 | 4/2010 | Hill et al. |
| 7,747,323 B2 | 6/2010 | Libbus et al. |
| 7,771,388 B2 | 8/2010 | Olsen et al. |
| 7,783,362 B2 | 8/2010 | Whitehurst et al. |
| 7,794,407 B2 | 9/2010 | Rothenberg |
| 7,797,050 B2 | 9/2010 | Libbus et al. |
| 7,813,805 B1 | 10/2010 | Farazi |
| 7,819,883 B2 | 10/2010 | Westlund et al. |
| 7,840,270 B2 | 11/2010 | Ignagni et al. |
| 7,853,302 B2 | 12/2010 | Rodriguez et al. |
| 7,869,865 B2 | 1/2011 | Govari et al. |
| 7,891,085 B1 | 2/2011 | Kuzma et al. |
| 7,925,352 B2 | 4/2011 | Stack et al. |
| 7,949,409 B2 | 5/2011 | Bly et al. |
| 7,949,412 B1 | 5/2011 | Harrison et al. |
| 7,962,215 B2 | 6/2011 | Ignagni et al. |
| 7,970,475 B2 | 6/2011 | Tehrani et al. |
| 7,972,323 B1 | 7/2011 | Bencini et al. |
| 7,974,693 B2 | 7/2011 | David et al. |
| 7,974,705 B2 | 7/2011 | Zdeblick et al. |
| 7,979,128 B2 | 7/2011 | Tehrani et al. |
| 7,994,655 B2 | 8/2011 | Bauer et al. |
| 8,000,765 B2 | 8/2011 | Rodriguez et al. |
| 8,019,439 B2 | 9/2011 | Kuzma et al. |
| 8,021,327 B2 | 9/2011 | Selkee |
| 8,036,750 B2 | 10/2011 | Caparso et al. |
| 8,050,765 B2 | 11/2011 | Lee et al. |
| 8,052,607 B2 | 11/2011 | Byrd |
| 8,104,470 B2 | 1/2012 | Lee et al. |
| 8,116,872 B2 | 2/2012 | Tehrani et al. |
| 8,121,692 B2 | 2/2012 | Haefner et al. |
| 8,135,471 B2 | 3/2012 | Zhang et al. |
| 8,140,164 B2 | 3/2012 | Tehrani et al. |
| 8,147,486 B2 | 4/2012 | Honour et al. |
| 8,160,701 B2 | 4/2012 | Zhao et al. |
| 8,160,711 B2 | 4/2012 | Tehrani et al. |
| 8,195,297 B2 | 6/2012 | Penner |
| 8,200,336 B2 | 6/2012 | Tehrani et al. |
| 8,206,343 B2 | 6/2012 | Racz |
| 8,224,456 B2 | 7/2012 | Daglow et al. |
| 8,233,987 B2 | 7/2012 | Gelfand et al. |
| 8,233,993 B2 | 7/2012 | Jordan |
| 8,239,037 B2 | 8/2012 | Glenn et al. |
| 8,244,358 B2 | 8/2012 | Tehrani et al. |
| 8,244,359 B2 | 8/2012 | Gelfand et al. |
| 8,244,378 B2 | 8/2012 | Bly et al. |
| 8,255,056 B2 | 8/2012 | Tehrani |
| 8,256,419 B2 | 9/2012 | Sinderby et al. |
| 8,265,736 B2 | 9/2012 | Sathaye et al. |
| 8,265,759 B2 | 9/2012 | Tehrani et al. |
| 8,275,440 B2 | 9/2012 | Rodriguez et al. |
| 8,280,513 B2 | 10/2012 | Tehrani et al. |
| 8,315,713 B2 | 11/2012 | Burnes et al. |
| 8,321,808 B2 | 11/2012 | Goetz et al. |
| 8,335,567 B2 | 12/2012 | Tehrani et al. |
| 8,340,783 B2 | 12/2012 | Sommer et al. |
| 8,348,941 B2 | 1/2013 | Tehrani |
| 8,369,954 B2 | 2/2013 | Stack et al. |
| 8,374,704 B2 | 2/2013 | Desai et al. |
| 8,388,541 B2 | 3/2013 | Messerly et al. |
| 8,388,546 B2 | 3/2013 | Rothenberg |
| 8,391,956 B2 | 3/2013 | Zellers et al. |
| 8,401,640 B2 | 3/2013 | Zhao et al. |
| 8,401,651 B2 | 3/2013 | Caparso et al. |
| 8,406,883 B1 | 3/2013 | Barker |
| 8,406,885 B2 | 3/2013 | Ignagni et al. |
| 8,412,331 B2 | 4/2013 | Tehrani et al. |
| 8,412,350 B2 | 4/2013 | Bly |
| 8,428,711 B2 | 4/2013 | Lin et al. |
| 8,428,726 B2 | 4/2013 | Ignagni et al. |
| 8,428,730 B2 | 4/2013 | Stack et al. |
| 8,433,412 B1 | 4/2013 | Westlund et al. |
| 8,442,638 B2 | 5/2013 | Libbus et al. |
| 8,457,764 B2 | 6/2013 | Ramachandran et al. |
| 8,467,876 B2 | 6/2013 | Tehrani |
| 8,473,068 B2 | 6/2013 | Farazi |
| 8,478,412 B2 | 7/2013 | Ignagni et al. |
| 8,478,413 B2 | 7/2013 | Karamanoglu et al. |
| 8,478,426 B2 | 7/2013 | Barker |
| 8,483,834 B2 | 7/2013 | Lee et al. |
| 8,504,158 B2 | 8/2013 | Karamanoglu et al. |
| 8,504,161 B1 | 8/2013 | Kornet et al. |
| 8,509,901 B2 | 8/2013 | Tehrani |
| 8,509,902 B2 | 8/2013 | Cho et al. |
| 8,509,919 B2 | 8/2013 | Yoo et al. |

(56) References Cited

U.S. PATENT DOCUMENTS

| | | |
|---|---|---|
| 8,511,303 B2 | 8/2013 | Djupesland |
| 8,512,256 B2 | 8/2013 | Rothenberg |
| 8,522,779 B2 | 9/2013 | Lee et al. |
| 8,527,036 B2 | 9/2013 | Jalde et al. |
| 8,532,793 B2 | 9/2013 | Morris et al. |
| 8,554,323 B2 | 10/2013 | Haefner et al. |
| 8,560,072 B2 | 10/2013 | Caparso et al. |
| 8,560,086 B2 | 10/2013 | Just et al. |
| 8,571,662 B2 | 10/2013 | Hoffer |
| 8,571,685 B2 | 10/2013 | Daglow et al. |
| 8,615,297 B2 | 12/2013 | Sathaye et al. |
| 8,617,228 B2 | 12/2013 | Wittenberger et al. |
| 8,620,412 B2 | 12/2013 | Griffiths et al. |
| 8,620,450 B2 | 12/2013 | Tockman et al. |
| 8,626,292 B2 | 1/2014 | McCabe et al. |
| 8,630,707 B2 | 1/2014 | Zhao et al. |
| 8,644,939 B2 | 2/2014 | Wilson et al. |
| 8,644,952 B2 | 2/2014 | Desai et al. |
| 8,646,172 B2 | 2/2014 | Kuzma et al. |
| 8,650,747 B2 | 2/2014 | Kuzma et al. |
| 8,676,323 B2 | 3/2014 | Ignagni et al. |
| 8,676,344 B2 | 3/2014 | Desai et al. |
| 8,694,123 B2 | 4/2014 | Wahlstrand et al. |
| 8,696,656 B2 | 4/2014 | Abboud et al. |
| 8,706,223 B2 | 4/2014 | Zhou et al. |
| 8,706,235 B2 | 4/2014 | Karamanoglu et al. |
| 8,706,236 B2 | 4/2014 | Ignagni et al. |
| 8,718,763 B2 | 5/2014 | Zhou et al. |
| 8,725,259 B2 | 5/2014 | Kornet et al. |
| 8,738,154 B2 | 5/2014 | Zdeblick et al. |
| 8,755,889 B2 | 6/2014 | Scheiner |
| 8,774,907 B2 | 7/2014 | Rothenberg |
| 8,781,578 B2 | 7/2014 | McCabe et al. |
| 8,781,582 B2 | 7/2014 | Ziegler et al. |
| 8,781,583 B2 | 7/2014 | Cornelussen et al. |
| 8,801,693 B2 | 8/2014 | He et al. |
| 8,805,511 B2 | 8/2014 | Karamanoglu et al. |
| 8,838,245 B2 | 9/2014 | Lin et al. |
| 8,858,455 B2 | 10/2014 | Rothenberg |
| 8,863,742 B2 | 10/2014 | Blomquist et al. |
| 8,886,277 B2 | 11/2014 | Kim et al. |
| 8,897,879 B2 | 11/2014 | Karamanoglu et al. |
| 8,903,507 B2 | 12/2014 | Desai et al. |
| 8,903,509 B2 | 12/2014 | Tockman et al. |
| 8,909,341 B2 | 12/2014 | Gelfand et al. |
| 8,914,113 B2 | 12/2014 | Zhang et al. |
| 8,918,169 B2 | 12/2014 | Kassab et al. |
| 8,918,987 B2 | 12/2014 | Kuzma et al. |
| 8,923,971 B2 | 12/2014 | Haefner et al. |
| 8,942,823 B2 | 1/2015 | Desai et al. |
| 8,942,824 B2 | 1/2015 | Yoo et al. |
| 8,948,884 B2 | 2/2015 | Ramachandran et al. |
| 8,968,299 B2 | 3/2015 | Kauphusman et al. |
| 8,972,015 B2 | 3/2015 | Stack et al. |
| 8,983,602 B2 | 3/2015 | Sathaye et al. |
| 9,008,775 B2 | 4/2015 | Sathaye et al. |
| 9,026,231 B2 | 5/2015 | Hoffer |
| 9,037,264 B2 | 5/2015 | Just et al. |
| 9,042,981 B2 | 5/2015 | Yoo et al. |
| 9,072,864 B2 | 7/2015 | Putz |
| 9,072,896 B2 | 7/2015 | Dar et al. |
| 9,072,899 B1 | 7/2015 | Nickloes |
| 9,108,058 B2 | 8/2015 | Hoffer |
| 9,108,059 B2 | 8/2015 | Hoffer |
| 9,125,578 B2 | 9/2015 | Grunwald |
| 9,138,580 B2 | 9/2015 | Ignagni et al. |
| 9,138,585 B2 | 9/2015 | Saha et al. |
| 9,144,680 B2 | 9/2015 | Kaula et al. |
| 9,149,642 B2 | 10/2015 | McCabe et al. |
| 9,168,377 B2 | 10/2015 | Hoffer |
| 9,174,046 B2 | 11/2015 | Francois et al. |
| 9,199,075 B1 | 12/2015 | Westlund |
| 9,205,258 B2 | 12/2015 | Simon et al. |
| 9,216,291 B2 | 12/2015 | Lee et al. |
| 9,220,898 B2 | 12/2015 | Hoffer |
| 9,226,688 B2 | 1/2016 | Jacobsen et al. |
| 9,226,689 B2 | 1/2016 | Jacobsen et al. |
| 9,242,088 B2 | 1/2016 | Thakkar et al. |
| 9,259,573 B2 | 2/2016 | Tehrani et al. |
| 9,295,846 B2 | 3/2016 | Westlund et al. |
| 9,314,618 B2 | 4/2016 | Imran et al. |
| 9,333,363 B2 | 5/2016 | Hoffer et al. |
| 9,345,422 B2 | 5/2016 | Rothenberg |
| 9,370,657 B2 | 6/2016 | Tehrani et al. |
| 9,398,931 B2 | 7/2016 | Wittenberger et al. |
| 9,415,188 B2 | 8/2016 | He et al. |
| 9,427,566 B2 | 8/2016 | Reed et al. |
| 9,427,588 B2 | 8/2016 | Sathaye et al. |
| 9,468,755 B2 | 10/2016 | Westlund |
| 9,474,894 B2 | 10/2016 | Mercanzini et al. |
| 9,485,873 B2 | 11/2016 | Shah et al. |
| 9,498,625 B2 | 11/2016 | Bauer |
| 9,498,631 B2 | 11/2016 | Demmer et al. |
| 9,504,837 B2 | 11/2016 | Demmer et al. |
| 9,532,724 B2 | 1/2017 | Grunwald et al. |
| 9,533,160 B2 | 1/2017 | Brooke et al. |
| 9,539,429 B2 | 1/2017 | Brooke et al. |
| 9,545,511 B2 | 1/2017 | Thakkar et al. |
| 9,561,369 B2 | 2/2017 | Burnes et al. |
| 9,566,436 B2 | 2/2017 | Hoffer et al. |
| 9,572,982 B2 | 2/2017 | Burnes et al. |
| 9,597,509 B2 | 3/2017 | Hoffer et al. |
| 9,615,759 B2 | 4/2017 | Hurezan et al. |
| 9,623,239 B2 | 4/2017 | Francois et al. |
| 9,623,252 B2 | 4/2017 | Sathaye et al. |
| 9,662,494 B2 | 5/2017 | Young et al. |
| 9,682,235 B1 | 6/2017 | O'Mahony et al. |
| 9,694,185 B2 | 7/2017 | Bauer |
| 9,717,899 B2 | 8/2017 | Kuzma et al. |
| 9,724,018 B2 | 8/2017 | Cho et al. |
| 9,744,349 B2 | 8/2017 | Westlund et al. |
| 9,744,351 B1 | 8/2017 | Gelfand et al. |
| 9,776,005 B2 | 10/2017 | Meyyappan et al. |
| 9,861,817 B2 | 1/2018 | Cho et al. |
| 9,872,989 B2 | 1/2018 | Jung et al. |
| 9,884,178 B2 | 2/2018 | Bouton et al. |
| 9,884,179 B2 | 2/2018 | Bouton et al. |
| 9,919,149 B2 | 3/2018 | Imran et al. |
| 9,931,504 B2 | 4/2018 | Thakkar et al. |
| 9,950,167 B2 | 4/2018 | Hoffer et al. |
| 9,956,132 B2 | 5/2018 | Francois et al. |
| 9,956,396 B2 | 5/2018 | Young et al. |
| 9,968,785 B2 | 5/2018 | Hoffer et al. |
| 9,968,786 B2 | 5/2018 | Bauer |
| 9,987,488 B1 | 6/2018 | Gelfand et al. |
| 9,999,768 B2 | 6/2018 | Gelfand et al. |
| 10,022,546 B2 | 7/2018 | Hoffer et al. |
| 10,035,017 B2 | 7/2018 | Thakkar et al. |
| 10,039,920 B1 | 8/2018 | Thakkar et al. |
| 10,195,429 B1 | 2/2019 | Thakkar et al. |
| 10,293,164 B2 | 5/2019 | Nash et al. |
| 10,300,270 B2 | 5/2019 | Gelfand et al. |
| 10,315,035 B2 | 6/2019 | Bauer |
| 10,335,592 B2 | 7/2019 | Bauer et al. |
| 10,369,361 B2 | 8/2019 | Bauer et al. |
| 10,391,314 B2 | 8/2019 | Hoffer et al. |
| 10,406,366 B2 | 9/2019 | Westlund et al. |
| 10,406,367 B2 | 9/2019 | Meyyappan |
| 10,413,203 B2 | 9/2019 | Saha et al. |
| 10,448,995 B2 | 10/2019 | Olson |
| 10,493,271 B2 | 12/2019 | Bauer |
| 2001/0052345 A1 | 12/2001 | Niazi |
| 2002/0026228 A1 | 2/2002 | Schauerte |
| 2002/0056454 A1 | 5/2002 | Samzelius |
| 2002/0065544 A1 | 5/2002 | Smits et al. |
| 2002/0087156 A1 | 7/2002 | Maguire et al. |
| 2002/0128546 A1 | 9/2002 | Silver |
| 2002/0188325 A1 | 12/2002 | Hill et al. |
| 2003/0078623 A1 | 4/2003 | Weinberg et al. |
| 2003/0125786 A1 | 7/2003 | Gliner et al. |
| 2003/0195571 A1 | 10/2003 | Burnes et al. |
| 2004/0003813 A1 | 1/2004 | Banner et al. |
| 2004/0010303 A1 | 1/2004 | Bolea et al. |
| 2004/0030362 A1 | 2/2004 | Hill et al. |

(56) References Cited

U.S. PATENT DOCUMENTS

| | | |
|---|---|---|
| 2004/0044377 A1 | 3/2004 | Larsson et al. |
| 2004/0064069 A1 | 4/2004 | Reynolds et al. |
| 2004/0077936 A1 | 4/2004 | Larsson et al. |
| 2004/0088015 A1 | 5/2004 | Casavant et al. |
| 2004/0111139 A1 | 6/2004 | McCreery |
| 2004/0186543 A1 | 9/2004 | King et al. |
| 2004/0210261 A1 | 10/2004 | King et al. |
| 2005/0004565 A1 | 1/2005 | Vanney |
| 2005/0013879 A1 | 1/2005 | Lin et al. |
| 2005/0021102 A1 | 1/2005 | Ignagni et al. |
| 2005/0027338 A1 | 2/2005 | Hill |
| 2005/0033136 A1 | 2/2005 | Govari et al. |
| 2005/0033137 A1 | 2/2005 | Oral et al. |
| 2005/0043765 A1 | 2/2005 | Williams et al. |
| 2005/0065567 A1 | 3/2005 | Lee et al. |
| 2005/0070981 A1 | 3/2005 | Verma |
| 2005/0075578 A1 | 4/2005 | Gharib et al. |
| 2005/0085865 A1 | 4/2005 | Tehrani |
| 2005/0085866 A1 | 4/2005 | Tehrani |
| 2005/0085867 A1 | 4/2005 | Tehrani et al. |
| 2005/0085868 A1 | 4/2005 | Tehrani et al. |
| 2005/0085869 A1 | 4/2005 | Tehrani et al. |
| 2005/0096710 A1 | 5/2005 | Kieval |
| 2005/0109340 A1 | 5/2005 | Tehrani |
| 2005/0113710 A1 | 5/2005 | Stahmann et al. |
| 2005/0115561 A1 | 6/2005 | Stahmann et al. |
| 2005/0131485 A1 | 6/2005 | Knudson et al. |
| 2005/0138791 A1 | 6/2005 | Black et al. |
| 2005/0138792 A1 | 6/2005 | Black et al. |
| 2005/0143787 A1 | 6/2005 | Boveja et al. |
| 2005/0165457 A1 | 7/2005 | Benser et al. |
| 2005/0182454 A1 | 8/2005 | Gharib et al. |
| 2005/0187584 A1 | 8/2005 | Denker et al. |
| 2005/0192655 A1 | 9/2005 | Black et al. |
| 2005/0251238 A1 | 11/2005 | Wallace et al. |
| 2005/0251239 A1 | 11/2005 | Wallace et al. |
| 2005/0288728 A1 | 12/2005 | Libbus et al. |
| 2005/0288730 A1 | 12/2005 | Deem et al. |
| 2006/0030894 A1 | 2/2006 | Tehrani |
| 2006/0035849 A1 | 2/2006 | Spiegelman et al. |
| 2006/0058852 A1 | 3/2006 | Koh et al. |
| 2006/0074449 A1 | 4/2006 | Denker et al. |
| 2006/0122661 A1 | 6/2006 | Mandell |
| 2006/0122662 A1 | 6/2006 | Tehrani et al. |
| 2006/0130833 A1 | 6/2006 | Younes |
| 2006/0142815 A1 | 6/2006 | Tehrani et al. |
| 2006/0149334 A1 | 7/2006 | Tehrani et al. |
| 2006/0155222 A1 | 7/2006 | Sherman et al. |
| 2006/0167523 A1 | 7/2006 | Tehrani et al. |
| 2006/0188325 A1 | 8/2006 | Dolan |
| 2006/0195159 A1 | 8/2006 | Bradley et al. |
| 2006/0217791 A1 | 9/2006 | Spinka et al. |
| 2006/0024222 A1 | 10/2006 | Bradley et al. |
| 2006/0224209 A1 | 10/2006 | Meyer |
| 2006/0229677 A1 | 10/2006 | Moffitt et al. |
| 2006/0247729 A1 | 11/2006 | Tehrani et al. |
| 2006/0253161 A1 | 11/2006 | Libbus et al. |
| 2006/0253182 A1 | 11/2006 | King |
| 2006/0258667 A1 | 11/2006 | Teng |
| 2006/0259107 A1 | 11/2006 | Caparso et al. |
| 2006/0282131 A1 | 12/2006 | Caparso et al. |
| 2006/0287679 A1 | 12/2006 | Stone |
| 2007/0005053 A1 | 1/2007 | Dando |
| 2007/0021795 A1 | 1/2007 | Tehrani |
| 2007/0027448 A1 | 2/2007 | Paul et al. |
| 2007/0087314 A1 | 4/2007 | Gomo |
| 2007/0093875 A1 | 4/2007 | Chavan et al. |
| 2007/0106357 A1 | 5/2007 | Denker et al. |
| 2007/0112402 A1 | 5/2007 | Grill et al. |
| 2007/0112403 A1 | 5/2007 | Moffitt et al. |
| 2007/0118183 A1 | 5/2007 | Gelfand et al. |
| 2007/0150006 A1 | 6/2007 | Libbus et al. |
| 2007/0168007 A1 | 7/2007 | Kuzma et al. |
| 2007/0173900 A1 | 7/2007 | Siegel et al. |
| 2007/0191908 A1 | 8/2007 | Jacob et al. |
| 2007/0196780 A1 | 8/2007 | Ware et al. |
| 2007/0203549 A1 | 8/2007 | Demarais et al. |
| 2007/0208388 A1 | 9/2007 | Jahns et al. |
| 2007/0221224 A1 | 9/2007 | Pittman et al. |
| 2007/0240718 A1 | 10/2007 | Daly |
| 2007/0250056 A1 | 10/2007 | Vanney |
| 2007/0250162 A1 | 10/2007 | Royalty |
| 2007/0255379 A1 | 11/2007 | Williams et al. |
| 2007/0265611 A1 | 11/2007 | Ignagni et al. |
| 2007/0288076 A1 | 12/2007 | Bulkes et al. |
| 2008/0039916 A1 | 2/2008 | Colliou et al. |
| 2008/0065002 A1 | 3/2008 | Lobl et al. |
| 2008/0125828 A1 | 5/2008 | Ignagni et al. |
| 2008/0161878 A1 | 7/2008 | Tehrani et al. |
| 2008/0167695 A1 | 7/2008 | Tehrani et al. |
| 2008/0177347 A1 | 7/2008 | Tehrani et al. |
| 2008/0183186 A1 | 7/2008 | Bly et al. |
| 2008/0183187 A1 | 7/2008 | Bly |
| 2008/0183239 A1 | 7/2008 | Tehrani et al. |
| 2008/0183240 A1 | 7/2008 | Tehrani et al. |
| 2008/0183253 A1 | 7/2008 | Bly |
| 2008/0183254 A1 | 7/2008 | Bly et al. |
| 2008/0183255 A1 | 7/2008 | Bly et al. |
| 2008/0183259 A1 | 7/2008 | Bly et al. |
| 2008/0183264 A1 | 7/2008 | Bly et al. |
| 2008/0183265 A1 | 7/2008 | Bly et al. |
| 2008/0188903 A1 | 8/2008 | Tehrani et al. |
| 2008/0215106 A1 | 9/2008 | Lee et al. |
| 2008/0288010 A1 | 11/2008 | Tehrani et al. |
| 2008/0288015 A1 | 11/2008 | Tehrani et al. |
| 2008/0312712 A1 | 12/2008 | Penner |
| 2008/0312725 A1 | 12/2008 | Penner |
| 2009/0024047 A1 | 1/2009 | Shipley et al. |
| 2009/0036947 A1 | 2/2009 | Westlund et al. |
| 2009/0118785 A1 | 5/2009 | Ignagni et al. |
| 2009/0275956 A1 | 11/2009 | Burnes et al. |
| 2009/0275996 A1 | 11/2009 | Burnes et al. |
| 2009/0276022 A1 | 11/2009 | Burnes et al. |
| 2009/0318993 A1 | 12/2009 | Eidenschink et al. |
| 2010/0022950 A1 | 1/2010 | Anderson et al. |
| 2010/0036451 A1 | 2/2010 | Hoffer |
| 2010/0077606 A1 | 4/2010 | Black et al. |
| 2010/0094376 A1 | 4/2010 | Penner |
| 2010/0114227 A1 | 5/2010 | Cholette |
| 2010/0114254 A1 | 5/2010 | Kornet |
| 2010/0198296 A1 | 8/2010 | Ignagni et al. |
| 2010/0204766 A1 | 8/2010 | Zdeblick et al. |
| 2010/0268311 A1 | 10/2010 | Cardinal et al. |
| 2010/0319691 A1 | 12/2010 | Lurie et al. |
| 2011/0034977 A1 | 2/2011 | Janik et al. |
| 2011/0060381 A1 | 3/2011 | Ignagni et al. |
| 2011/0077726 A1 | 3/2011 | Westlund et al. |
| 2011/0093032 A1 | 4/2011 | Boggs, II et al. |
| 2011/0118815 A1 | 5/2011 | Kuzma et al. |
| 2011/0230932 A1 | 9/2011 | Tehrani et al. |
| 2011/0230935 A1 | 9/2011 | Zdeblick |
| 2011/0230945 A1 | 9/2011 | Ohtaka et al. |
| 2011/0270358 A1 | 11/2011 | Davis et al. |
| 2011/0288609 A1 | 11/2011 | Tehrani et al. |
| 2012/0035684 A1 | 2/2012 | Thompson et al. |
| 2012/0035691 A1* | 2/2012 | Tockman ............ A61N 1/36114 607/116 |
| 2012/0053654 A1 | 3/2012 | Tehrani et al. |
| 2012/0078320 A1 | 3/2012 | Schotzko et al. |
| 2012/0130217 A1 | 5/2012 | Kauphusman et al. |
| 2012/0158091 A1 | 6/2012 | Tehrani et al. |
| 2012/0209284 A1 | 8/2012 | Westlund et al. |
| 2012/0215278 A1 | 8/2012 | Penner |
| 2012/0323293 A1 | 12/2012 | Tehrani et al. |
| 2013/0018247 A1 | 1/2013 | Glenn et al. |
| 2013/0018427 A1 | 1/2013 | Pham et al. |
| 2013/0023972 A1 | 1/2013 | Kuzma et al. |
| 2013/0030496 A1 | 1/2013 | Karamanoglu et al. |
| 2013/0030497 A1 | 1/2013 | Karamanoglu et al. |
| 2013/0030498 A1 | 1/2013 | Karamanoglu et al. |
| 2013/0060245 A1 | 3/2013 | Grunewald et al. |
| 2013/0116743 A1 | 5/2013 | Karamanoglu et al. |
| 2013/0123891 A1 | 5/2013 | Swanson |
| 2013/0131743 A1 | 5/2013 | Yamasaki et al. |

(56) References Cited

U.S. PATENT DOCUMENTS

| | | |
|---|---|---|
| 2013/0158625 A1 | 6/2013 | Gelfand et al. |
| 2013/0165989 A1 | 6/2013 | Gelfand et al. |
| 2013/0167372 A1 | 7/2013 | Black et al. |
| 2013/0197601 A1 | 8/2013 | Tehrani et al. |
| 2013/0237906 A1 | 9/2013 | Park et al. |
| 2013/0268018 A1 | 10/2013 | Brooke et al. |
| 2013/0289686 A1 | 10/2013 | Masson et al. |
| 2013/0296964 A1 | 11/2013 | Tehrani |
| 2013/0296973 A1 | 11/2013 | Tehrani et al. |
| 2013/0317587 A1 | 11/2013 | Barker |
| 2013/0333696 A1 | 12/2013 | Lee et al. |
| 2014/0067032 A1 | 3/2014 | Morris et al. |
| 2014/0088580 A1 | 3/2014 | Wittenberger et al. |
| 2014/0114371 A1 | 4/2014 | Westlund et al. |
| 2014/0121716 A1 | 5/2014 | Casavant et al. |
| 2014/0128953 A1 | 5/2014 | Zhao et al. |
| 2014/0148780 A1 | 5/2014 | Putz |
| 2014/0316486 A1 | 10/2014 | Zhou et al. |
| 2014/0324115 A1 | 10/2014 | Ziegler et al. |
| 2014/0378803 A1 | 12/2014 | Geistert et al. |
| 2015/0018839 A1 | 1/2015 | Morris et al. |
| 2015/0034081 A1 | 2/2015 | Tehrani et al. |
| 2015/0045810 A1 | 2/2015 | Hoffer et al. |
| 2015/0045848 A1 | 2/2015 | Cho et al. |
| 2015/0119950 A1 | 4/2015 | Demmer et al. |
| 2015/0148877 A1* | 5/2015 | Thakkar ............ A61M 25/0147 607/116 |
| 2015/0165207 A1 | 6/2015 | Karamanoglu |
| 2015/0196354 A1 | 7/2015 | Haverkost et al. |
| 2015/0196356 A1 | 7/2015 | Kauphusman et al. |
| 2015/0202448 A1 | 7/2015 | Hoffer et al. |
| 2015/0231348 A1 | 8/2015 | Lee et al. |
| 2015/0250982 A1 | 9/2015 | Osypka et al. |
| 2015/0265833 A1 | 9/2015 | Meyyappan et al. |
| 2015/0283340 A1 | 10/2015 | Zhang et al. |
| 2015/0290476 A1 | 10/2015 | Krocak et al. |
| 2015/0359487 A1 | 12/2015 | Coulombe |
| 2015/0374252 A1 | 12/2015 | De et al. |
| 2015/0374991 A1 | 12/2015 | Morris et al. |
| 2016/0001072 A1 | 1/2016 | Gelfand et al. |
| 2016/0129244 A1 | 5/2016 | Westlund |
| 2016/0144078 A1 | 5/2016 | Young et al. |
| 2016/0193460 A1 | 7/2016 | Xu et al. |
| 2016/0228696 A1 | 8/2016 | Imran et al. |
| 2016/0239627 A1 | 8/2016 | Cerny et al. |
| 2016/0256692 A1 | 9/2016 | Baru |
| 2016/0310730 A1 | 10/2016 | Martins et al. |
| 2016/0331326 A1 | 11/2016 | Xiang et al. |
| 2016/0367815 A1 | 12/2016 | Hoffer |
| 2017/0007825 A1 | 1/2017 | Thakkar et al. |
| 2017/0013713 A1 | 1/2017 | Shah et al. |
| 2017/0021163 A1 | 1/2017 | Westlund et al. |
| 2017/0021166 A1 | 1/2017 | Bauer et al. |
| 2017/0028191 A1 | 2/2017 | Mercanzini et al. |
| 2017/0036017 A1 | 2/2017 | Tehrani et al. |
| 2017/0050033 A1 | 2/2017 | Wechter |
| 2017/0143973 A1 | 5/2017 | Tehrani |
| 2017/0143975 A1 | 5/2017 | Hoffer et al. |
| 2017/0196503 A1 | 7/2017 | Narayan et al. |
| 2017/0224993 A1 | 8/2017 | Sathaye et al. |
| 2017/0232250 A1 | 8/2017 | Kim et al. |
| 2017/0252558 A1 | 9/2017 | O'Mahony et al. |
| 2017/0291023 A1 | 10/2017 | Kuzma et al. |
| 2017/0296812 A1 | 10/2017 | O'Mahony et al. |
| 2017/0312006 A1 | 11/2017 | McFarlin et al. |
| 2017/0312507 A1 | 11/2017 | Bauer et al. |
| 2017/0312508 A1 | 11/2017 | Bauer et al. |
| 2017/0312509 A1 | 11/2017 | Bauer et al. |
| 2017/0326354 A1 | 11/2017 | Westlund et al. |
| 2017/0326359 A1 | 11/2017 | Gelfand et al. |
| 2017/0347921 A1 | 12/2017 | Haber et al. |
| 2018/0001086 A1 | 1/2018 | Bartholomew et al. |
| 2018/0008821 A1 | 1/2018 | Gonzalez et al. |
| 2018/0110562 A1 | 4/2018 | Govari et al. |
| 2018/0117265 A1 | 5/2018 | Armes |
| 2018/0117334 A1 | 5/2018 | Jung |
| 2018/0256440 A1 | 9/2018 | Francois et al. |
| 2018/0280692 A1 | 10/2018 | Gelfand et al. |
| 2018/0326209 A1 | 11/2018 | Gelfand et al. |
| 2018/0339156 A1* | 11/2018 | Nash ................ A61N 1/36185 |
| 2019/0247656 A1 | 8/2019 | Bauer |
| 2019/0255322 A1 | 8/2019 | Bauer et al. |
| 2019/0351229 A1 | 11/2019 | Westlund et al. |

FOREIGN PATENT DOCUMENTS

| | | |
|---|---|---|
| EP | 0993840 A1 | 4/2000 |
| EP | 1304135 A2 | 4/2003 |
| EP | 0605796 B1 | 8/2003 |
| EP | 0783346 B2 | 1/2007 |
| EP | 2489395 A1 | 8/2012 |
| FR | 2801509 A1 | 6/2001 |
| JP | H08510677 A | 11/1996 |
| JP | 2003503119 A | 1/2003 |
| JP | 2010516353 A | 5/2010 |
| JP | 2011200571 A | 10/2011 |
| JP | 2012000195 A | 1/2012 |
| WO | WO-9407564 A2 | 4/1994 |
| WO | WO-9508357 A1 | 3/1995 |
| WO | WO-9964105 A1 | 12/1999 |
| WO | WO-9965561 A1 | 12/1999 |
| WO | WO-0100273 A1 | 1/2001 |
| WO | WO-02058785 A1 | 8/2002 |
| WO | WO-03005887 A2 | 1/2003 |
| WO | WO-03094855 A1 | 11/2003 |
| WO | WO-2005018524 A2 | 3/2005 |
| WO | WO-2006063339 A2 | 6/2006 |
| WO | WO-2006110338 A1 | 10/2006 |
| WO | WO-2006115877 A1 | 11/2006 |
| WO | WO-2007053508 A1 | 5/2007 |
| WO | WO-2008092246 A1 | 8/2008 |
| WO | WO-2008094344 A1 | 8/2008 |
| WO | WO-2009006337 A1 | 1/2009 |
| WO | WO-2009134459 A2 | 11/2009 |
| WO | WO-2010029842 A1 | 3/2010 |
| WO | WO-2010148412 A1 | 12/2010 |
| WO | WO-2011094631 A1 | 8/2011 |
| WO | WO-2011158410 A1 | 12/2011 |
| WO | WO-2012106533 A2 | 8/2012 |
| WO | 2013/086461 A1 | 6/2013 |
| WO | WO-2013131187 A1 | 9/2013 |
| WO | WO-2013188965 A1 | 12/2013 |
| WO | WO-2014008171 A1 | 1/2014 |
| WO | WO-2015075548 A1 | 5/2015 |
| WO | WO-2015109401 A1 | 7/2015 |
| WO | WO-2019154834 A1 | 8/2019 |
| WO | WO-2019154837 A1 | 8/2019 |
| WO | WO-2019154839 A1 | 8/2019 |

OTHER PUBLICATIONS

Antonica A., et al., "Vagal Control of Lymphocyte Release from Rat Thymus," Journal of the Autonomic Nervous System, ELSEVIER, vol. 48(3), Aug. 1994, pp. 187-197.

Ataya, A., et al., "Temporary Transvenous Diaphragmatic Neurostimulation in Prolonged Mechanically Ventilated Patients: A Feasibility Trial (RESCUE 1)," Critical Care Explorations, vol. 2, pp. 1-7, 2020.

Ayas N.T., et al., "Prevention of Human Diaphragm Atrophy with Short periods of Electrical Stimulation," American Journal of Respiratory and Critical Care Medicine, Jun. 1999, vol. 159(6), pp. 2018-2020.

Borovikova, et al., "Role of the Vagus Nerve in the Anti-Inflammatory Effects of CNI-1493," Proceedings of the Annual Meeting of Professional Research Scientists: Experimental Biology 2000, Abstract 97.9, Apr. 15-18, 2000.

Borovikova L.V., et al., "Role of Vagus Nerve Signaling in CNI-1493-Mediated Suppression of Acute Inflammation," Autonomic Neuroscience: Basic and Clinical, vol. 85 (1-3), Dec. 20, 2000, pp. 141-147.

(56) References Cited

OTHER PUBLICATIONS

Borovikova L.V., et al., "Vagus Nerve Stimulation Attenuates the Systemic Inflammatory Response to Endotoxin," Nature, Macmillan Magazines Ltd, vol. 405, May 25, 2000, pp. 458-462.
Chinese Search Report for Application No. CN2013/80023357.5, dated Jul. 24, 2015.
Co-pending U.S. Appl. No. 15/606,867, filed May 26, 2017.
Daggeti, W.M. et al., "Intracaval Electrophrenic Stimulation. I. Experimental Application during Barbiturate Intoxication Hemorrhage and Gang," Journal of Thoracic and Cardiovascular Surgery, 1966, vol. 51 (5), pp. 676-884.
Daggeti, W.M. et al., "Intracaval electrophrenic stimulation. II. Studies on Pulmonary Mechanics Surface Tension Urine Flow and Bilateral Ph," Journal of Thoracic and Cardiovascular Surgery, 1970, vol. 60(1 ), pp. 98-107.
De Gregorio, M.A. et al., "The Gunther Tulip Retrievable Filter: Prolonged Temporary Filtration by Repositioning within the Inferior Vena Cava," Journal of Vascular and Interventional Radiology, 2003, vol. 14, pp. 1259-1265.
Deng Y-J et al., "The Effect of Positive Pressure Ventilation Combined with Diaphragm Pacing on Respiratory Mechanics in Patients with Respiratory Failure; Respiratory Mechanics," Chinese critical care medicine, Apr. 2011, vol. 23(4), pp. 213-215.
Elkins, M. et al., "Inspiratory muscle training facilitates weaning from mechanical ventilation among patients in the intensive care unit: a systematic review," Journal of Physiotherapy, vol. 61, pp. 1-10, 2015.
Escher, Doris J.W. et al., "Clinical Control of Respiration by Transvenous Phrenic Pacing," American Society for Artificial Internal Organs: Apr. 1968—vol. 14—Issue 1—pp. 192-197.
European Search Report for Application No. 13758363, dated Nov. 12, 2015.
European Search Report for Application No. EP17169051.4, dated Sep. 8, 2017, 7 pages.
Extended European Search Report for Application No. 14864542.7, dated Jun. 2, 2017, 8 pages.
Extended European Search Report for Application No. 15740415.3, dated Jul. 7, 2017.
Fleshner M., et al., "Thermogenic and Corticosterone Responses to Intravenous Cytokines (IL-1β and TNF-α) are Attenuated by Subdiaphragmatic Vagotomy," Journal of Neuroimmunology, vol. 86, Jun. 1998, pp. 134-141.
Frisch S., "A Feasibility Study of a Novel Minimally Invasive Approach for Diaphragm Pacing," Master of Science Thesis, Simon Fraser University, 2009, p. 148.
Furman, S., "Transvenous Stimulation of the Phrenic Nerves," Journal of Thoracic and Cardiovascular Surgery, 1971, vol. 62 (5), pp. 743-751.
Gaykema R.P.A. et al., "Subdiaphragmatic Vagotomy Suppresses Endotoxin-Induced Activation of Hypothalamic Corticotropin-Releasing Hormone Neurons and ACTH Secretion," Endocrinology, The Endocrine Society, vol. 136 (10), 1995, pp. 4717-4720.
Gupta A.K., "Respiration Rate Measurement Based on Impedance Pneumography," Data Acquisition Products, Texas Instruments, Application Report, SBAA181, Feb. 2011, 11 pages.
Guslandi M., "Nicotine Treatment for Ulcerative Colitis," The British Journal of Clinical Pharmacology, Blackwell Science Ltd, vol. 48, 1999, pp. 481-484.
Hoffer J.A. et al., "Diaphragm Pacing with Endovascular Electrodes", IFESS 2010—International Functional Electrical Stimulation Society, 15th Anniversary Conference, Vienna, Austria, Sep. 2010.
Huffman, William J. et al., "Modulation of Neuroinflammation and Memory Dysfunction Using Percutaneous Vagus Nerve Stimulation in Mice," Brain Stimulation, 2018.
Ishii, K. et al., "Effects of Bilateral Transvenous Diaphragm Pacing on Hemodynamic Function in Patients after Cardiac Operations," J. Thorac. Cardiovasc. Surg., 1990.
Japanese Office Action in corresponding Japanese Application No. 2014-560202, dated Dec. 6, 2016, 4 pages.
Japanese Office Action in corresponding Japanese Application No. 2014-560202, dated Oct. 17, 2017, 5 pages.
Kawashima K., et al., "Extraneuronal Cholinergic System in Lymphocytes," Pharmacology & Therapeutics, ELSEVIER, vol. 86, 2000, pp. 29-48.
Levine S., et al., "Rapid disuse atrophy of diaphragm fibers in mechanically ventilated humans," New England Journal of Medicine, 2008, vol. 358, pp. 1327-1335.
Lungpacer: Therapy, News.< http://lungpacer.com>. Accessed Dec. 27, 2016.
Madretsma, G.S., et al., "Nicotine Inhibits the In-vitro Production of Interleukin 2 and Tumour Necrosis Factor-α by Human Mononuclear Cells," Immunopharmacology, ELSEVIER, vol. 35 (1), Oct. 1996, pp. 47-51.
Mankowski, R.T., et al., "Intraoperative hemidiaphragm electrical stimulation reduces oxidative stress and upregulates autophagy in surgery patients undergoing mechanical ventilation: exploratory study," Journal of Translational Medicine, vol. 14, pp. 1-7, 2016.
Marcy, T.W. et al., "Diaphragm Pacing for Ventilatory Insufficiency," Journal of Intensive Care Medicine, 1987, vol. 2 (6), pp. 345-353.
Martin, A.D. et al., "Inspiratory muscle strength training improves weaning outcome in failure to wean patients: a randomized trial," Critical Care, vol. 15, pp. 1-12, 2011.
Meyyappan R., "Diaphragm Pacing during Controlled Mechanical Ventilation: Pre-Clinical Observations Reveal A Substantial Improvement In Respiratory Mechanics", 17th Biennial Canadian Biomechanics Society Meeting, Burnaby, BC, Jun. 6-9, 2012.
Nabutovsky, Y., et al., "Lead Design and Initial Applications of a New Lead for Long-Term Endovascular Vagal Stimulation," PACE, Blackwell Publishing, Inc, vol. 30(1), Jan. 2007, pp. S215-S218.
Notification of Reasons for Rejection and English language translation issued in corresponding Japanese Patent Application No. 2015-517565, dated Mar. 28, 2017, 6 pages.
Onders R.,, "A Diaphragm Pacing as a Short- Term Assist to Positive Pressure Mechanical Ventilation in Critical Care Patients," Chest, Oct. 24, 2007, vol. 132(4), pp. 5715-5728.
Onders R.,, "Diaphragm Pacing for Acute Respiratory Failure," Difficult Decisions in Thoracic Surgery, Chapter 37, Springer-Verlag, 2011, M.K. Ferguson (ed.), pp. 329-335.
Onders R, et al., "Diaphragm Pacing with Natural Orifice Transluminal Endoscopic Surgery: Potential for Difficult-To-Wean Intensive Care Unit Patients," Surgical Endoscopy, 2007, vol. 21, pp. 475-479.
Pavlovic D., et al., "Diaphragm Pacing During Prolonged Mechanical Ventilation of the Lungs could Prevent from Respiratory Muscle Fatigue," Medical Hypotheses, vol. 60 (3), 2003, pp. 398-403.
Planas R.F., et al., "Diaphragmatic Pressures: Transvenous vs. Direct Phrenic Nerve Stimulation," Journal of Applied Physiology, vol. 59(1), 1985, pp. 269-273.
Romanovsky, A.A., et al., "The Vagus Nerve in the Thermoregulatory Response to Systemic Inflammation," American Journal of Physiology, vol. 273 (1 Pt 2), 1997, pp. R407-13.
Salmela L., et al., "Verification of the Position of a Central Venous Catheter by Intra-Atrial ECG. When does this method fail?," Acta Anasthesiol Scand, vol. 37 (1), 1993, pp. 26-28.
Sandborn W.J., "Transdermal Nicotine for Mildly to Moderately Active Ulcerative Colitis," Annals of Internal Medicine, vol. 126 (5), Mar. 1, 1997, pp. 364-371.
Sandoval R., "A Catch/Ike Property-Based Stimulation Protocol for Diaphragm Pacing", Master of Science Coursework project, Simon Fraser University, Mar. 2013.
Sarnoff, S.J. et al., "Electrophrenic Respiration," Science, 1948, vol. 108, p. 482.
Sato E., et al., "Acetylcholine Stimulates Alveolar Macrophages to Release Inflammatory Cell Chemotactic Activity," American Journal of Physiology, vol. 274 (Lung Cellular and Molecular Physiology 18), 1998, pp. L970-79.
Sato, K.Z., et al., "Diversity of mRNA Expression for Muscarinic Acetylcholine Receptor Subtypes and Neuronal Nicotinic Acetylcholine Receptor Subunits in Human Mononuclear Leukocytes and Leukemic Cell Lines," Neuroscience Letters, vol. 266 (1), 1999, pp. 17-20.

(56) References Cited

OTHER PUBLICATIONS

Schauerte P., et al., "Transvenous Parasympathetic Nerve Stimulation in the Inferior Vena Cava and Atrioventricular Conduction," Journal of Cardiovascular Electrophysiology, vol. 11 (1), Jan. 2000, pp. 64-69.

Schauerte P.N., et al., "Transvenous Parasympathetic Cardiac Nerve Stimulation: An Approach for Stable Sinus Rate Control," Journal of Cardiovascular Electrophysiology, vol. 10 (11), Nov. 1999, pp. 1517-1524.

Scheinman R.I., et al., "Role of Transcriptional Activation of IKBa in Mediation of Immunosuppression by Glucocorticoids," Science, vol. 270, Oct. 13, 1995, pp. 283-286.

Sher, M.E., et al., "The Influence of Cigarette Smoking on Cytokine Levels in Patients with Inflammatory Bowel Disease," Inflammatory Bowel Diseases, vol. 5 (2), May 1999, pp. 73-78.

Steinlein, O., "New Functions for Nicotinic Acetylcholine Receptors?," Behavioural Brain Research, vol. 95, 1998, pp. 31-35.

Sternberg E.M., (Series Editor) "Neural-Immune Interactions in Health and Disease," The Journal of Clinical Investigation, vol. 100 (11), Dec. 1997, pp. 2641-2647.

Sykes., A.P., et al., "An Investigation into the Effect and Mechanisms of Action of Nicotine in Inflammatory Bowel Disease," Inflammation Research, vol. 49, 2000, pp. 311-319.

Toyabe S., et al., "Identification of Nicotinic Acetylcholine Receptors on Lymphocytes in the Periphery as well as Thymus in Mice," Immunology, vol. 92, 1997, pp. 201-205.

Van Dijk A.P.M., et al., "Transdermal Nicotine Inhibits Interleukin 2 Synthesis by Mononuclear Cells Derived from Healthy Volunteers," European Journal of Clinical Investigation, vol. 28, 1998, pp. 664-671.

Wanner, A. et al., "Trasvenous Phrenic Nerve Stimulation in Anesthetized Dogs," Journal of Applied Physiology, 1973, vol. 34 (4), pp. 489-494.

Watkins L.R., et al., "Blockade of lnterleukin-1 Induced Hyperthermia by Subdiaphragmatic Vagotomy: Evidence for Vagal Mediation of Immune-Brain Communication," Neuroscience Letters, vol. 183, 1995, pp. 27-31.

Watkins L.R., et al., "Implications of Immune-to-Brain Communication for Sickness and Pain," PNAS (Proceedings of the National Academy of Sciences of the USA), vol. 96 (14), Jul. 6, 1999, pp. 7710-7713.

Whaley K., et al., "C2 Synthesis by Human Monocytes is Modulated by a Nicotinic Cholinergic Receptor," Nature, vol. 293, Oct. 15, 1981, pp. 580-582 (and reference page).

PCT Search Report dated Oct. 26, 2018 for PCT Application No. PCT/IB2018/000603, 7 pages.

PCT Search Report and Written Opinion dated Oct. 17, 2018 for PCT Application No. PCT/US2018/043661, 13 pages.

\* cited by examiner

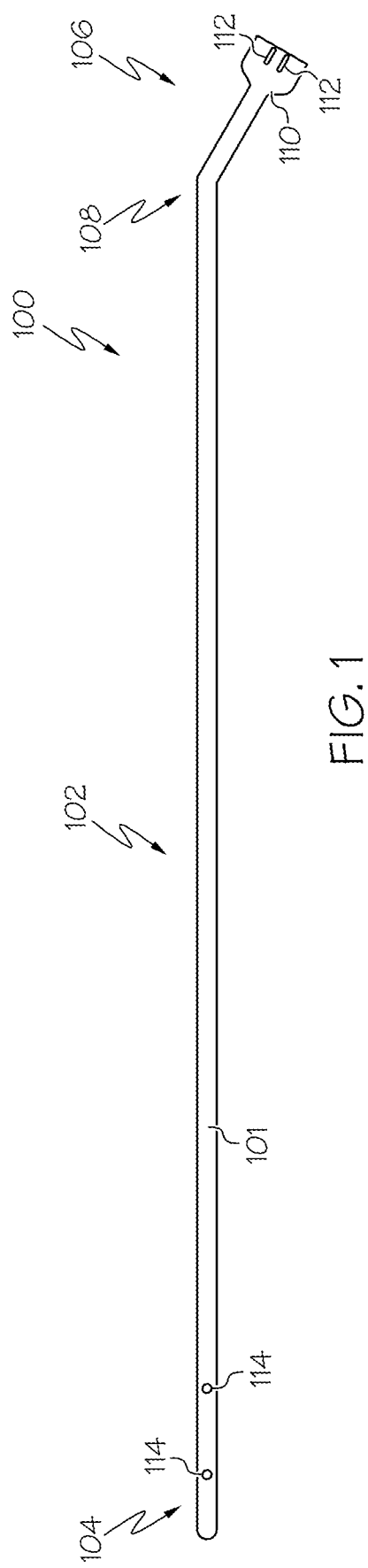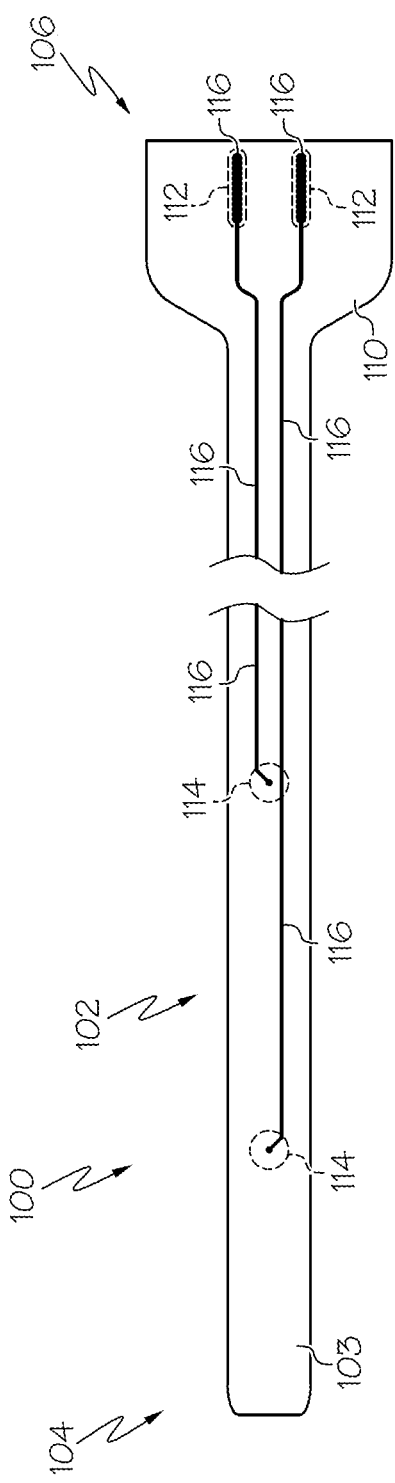

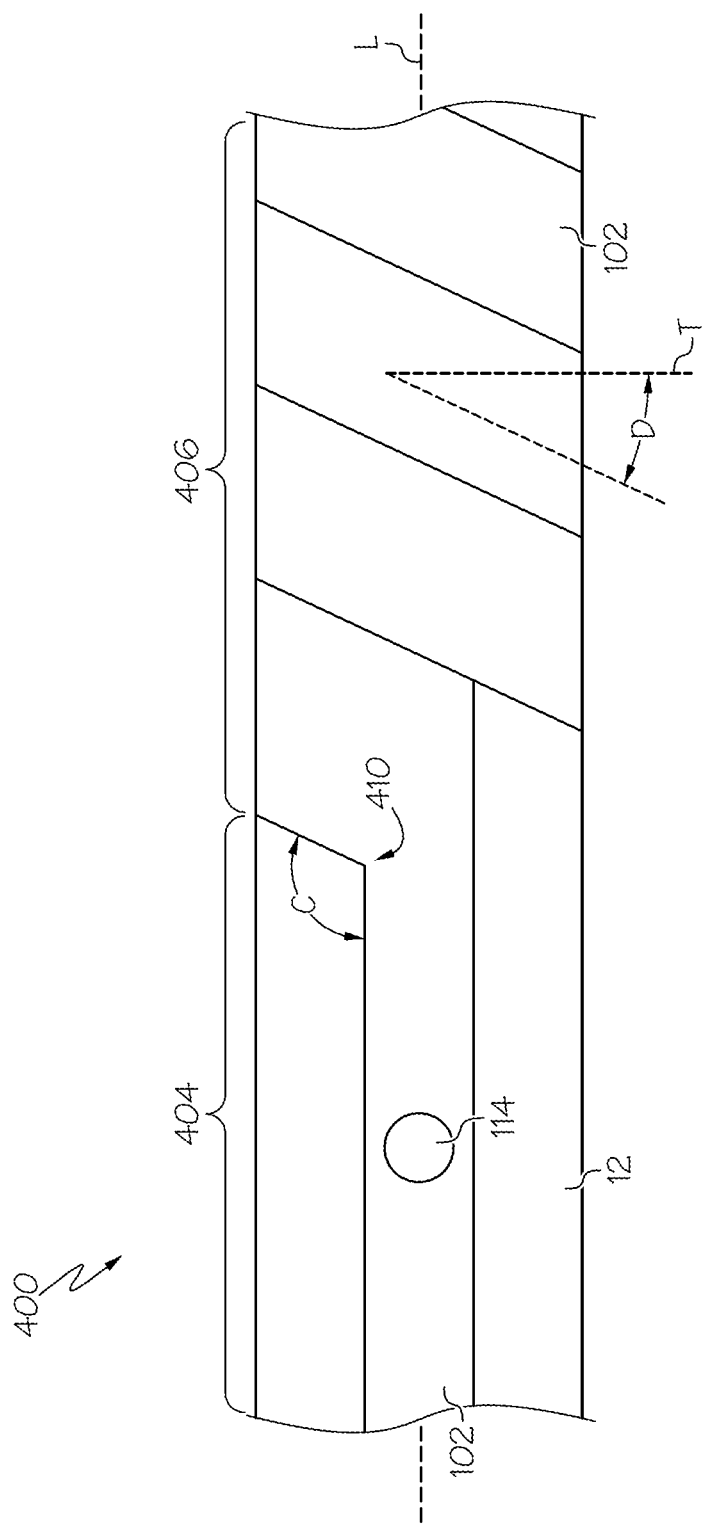

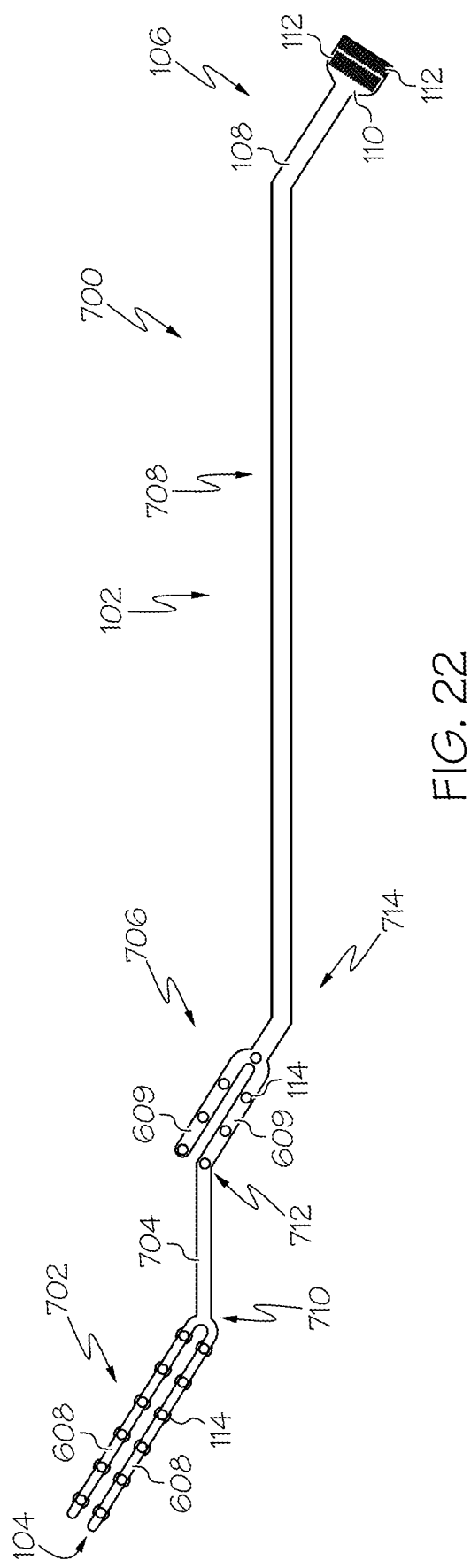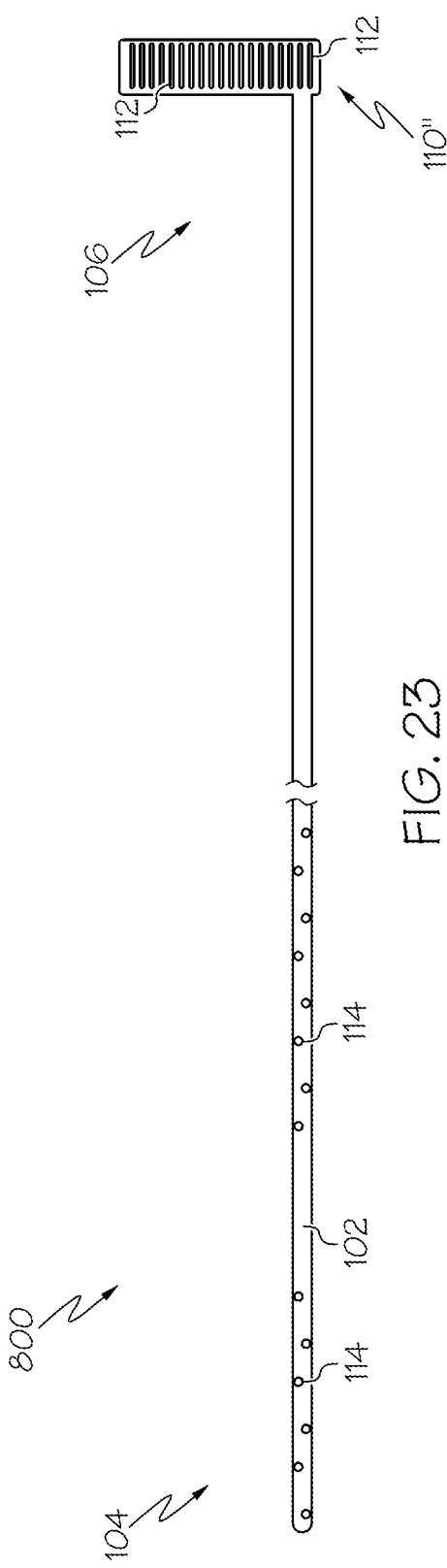
FIG. 22
FIG. 23

CIRCUITRY FOR MEDICAL STIMULATION SYSTEMS

CROSS-REFERENCE TO RELATED APPLICATION

This application claims priority to U.S. Provisional Application No. 62/860,452, filed on Jun. 12, 2019, which is hereby incorporated by reference in its entirety. All publications, patent applications, and patents mentioned in this specification are herein incorporated by reference in their entirety to the same extent as if each individual document was specifically individually indicated to be incorporated by reference.

TECHNICAL FIELD

Embodiments of this disclosure relate to systems, devices, and apparatuses for providing electrical circuits, leads, and/or electrodes on medical devices configured for stimulation of a body. Embodiments of this disclosure generally relate to medical devices (including systems) for the stimulation of nerves and/or muscles, including a flexible circuitry construction for use during the stimulation of muscles and/or nerves. In embodiments, systems may restore, enhance, and/or modulate diminished neurophysiological functions using electrical stimulation. Some embodiments provide a flexible layer disposed over a medical device for positioning electrodes external of the device and adjacent to one or more target nerves during a procedure.

BACKGROUND

Critical care patients, particularly those requiring invasive mechanical ventilation (MV), may generally experience higher levels of diaphragm, lung, brain, heart, and/or other organ injury. The respiratory muscles (e.g., diaphragm, sternocleidomastoid, scalenes, pectoralis minor, external intercostals, internal intercostals, abdominals, quadratus, etc.) may rapidly lose mass and strength during MV. A patient's lungs may suffer from ventilator-induced trauma, including high and low pressure injuries. Cognitive effects of MV may be caused by several factors, including aberrant neuro-signaling and inflammatory responses. Limiting a duration for which patients are subjected to MV may contribute toward minimizing such negative side effects. However, rapid respiratory muscle atrophy in MV patients makes it challenging to transition patients away from a dependency on MV. Options may be limited for strengthening the respiratory muscles of critical care patients, particularly for those that are on MV, so that they may regain an ability to breathe without external respiratory support.

SUMMARY

Embodiments of the present disclosure relate to, among other things, systems, devices, and methods for applying stimulation to one or more anatomical targets. Embodiments of flexible circuitry apparatuses for the systems and devices described herein may be used with MV, such as, for example, stimulation of respiratory nerves and/or respiratory muscles. Each of the embodiments disclosed herein may include one or more of the features described in connection with any of the other disclosed embodiments.

In one example, a medical device may include a flexible body having a proximal end and a distal end and an electrode positioned on the body proximate the distal end. The electrode is configured to provide an electrical charge for stimulating tissue. The medical device may include an electrical connection positioned on the body proximate the proximal end. The electrical connection is configured to electrically couple the electrode to a power source. The medical device may include an electrical lead connecting the electrode to the electrical connection, wherein the lead is on or in the flexible body. The body is configured to have a first configuration prior to being secured to an exterior of a tube and a second configuration having a shape that conforms to a profile of the tube with the electrode secured to an exterior of the tube Any of the systems or methods disclosed herein may include any of the following features. The medical device may include the tube. The flexible body is helically wound about the exterior of the tube in a plurality of winds, to achieve the second configuration. The medical device may include the tube, and securing the flexible body about the exterior of the tube causes the tube to have regions of varying flexibility at locations of the tube having the flexible body. The flexible body includes a dielectric substrate film disposed between the electrode and the electrical lead. The flexible body further includes a hole through the dielectric substrate film, and the hole is filled with a conductive material electrically connecting the electrode to the electrical lead. The medical device includes a sensor, an electronic chip, or an integrated circuit disposed within the dielectric substrate film and between the electrode and the electrical lead. The flexible body, in the first configuration, includes at least one segment having an enlarged width relative to an adjacent portion of the flexible body, wherein the at least one segment is less flexible than the adjacent portion of the flexible body. The flexible body, in the first configuration, includes at least one segment having a nonlinear configuration adjacent to a portion of the flexible body having a linear configuration, wherein the at least one segment is more flexible than the portion. The medical device includes the tube. The flexible body, in the first configuration, includes at least one bend between the proximal end and the distal end such that a longitudinal axis of a proximal portion proximal to the bend is transverse to a longitudinal axis of a distal portion distal to the bend. A flexibility of a segment of the medical device having the proximal portion differs from a flexibility of a segment of the medical device having the distal portion, due to the arrangements of the proximal and distal portions on the tube. The at least one bend causes a change in direction of a helical wind of the flexible body about the tube, when the flexible body is on the second configuration. The flexible body includes at least one segment having a stiffening structure that is configured to increase a stiffness of the flexible body relative to an adjacent portion of the flexible body. The flexible body includes at least one segment at the distal end having a plurality of branches, wherein each of the plurality of branches includes an array of electrodes. The at least one segment is angled relative to the proximal end such that such that a longitudinal axis of the plurality of branches is transverse to a longitudinal axis of the flexible body. The flexible body includes a second segment proximal of the distal end and having a plurality of second branches, wherein each of the plurality of second branches includes a second array of electrodes.

In another example, a medical device may include a tube having a longitudinal length and at least one lumen. The tube is configured to receive at least one of a device and a fluid in the at least one lumen. The medical device may include a flexible body having a stimulation array configured to provide an electrical charge for stimulating tissue. The flexible body includes a proximal portion and a distal portion separated from the proximal portion by at least one bend. The flexible body is configured to cover at least a portion of the longitudinal length of the tube such that the stimulation array is disposed about an exterior of the tubular body. The at least one bend is configured to arrange one of the proximal portion and the distal portion in a linear configuration and the other of the proximal portion and the distal portion in a nonlinear configuration relative to the tube, when the flexible body is wound about the exterior of the tube.

Any of the systems or methods disclosed herein may include any of the following features. The stimulation array includes a distal electrode array positioned on the flexible body proximate to the distal portion. The distal electrode array is configured to provide the electrical charge for stimulating tissue at a first location. The stimulation array includes a proximal electrode array positioned on the flexible body proximate to the proximal portion. The proximal electrode array is configured to provide the electrical charge for stimulating tissue at a second location that is different than the first location. The stimulation array includes an electrical connection positioned on the flexible body proximate to the proximal portion and configured to electrically couple the distal electrode array and the proximal electrode array to a power source. The at least one bend causes a change in direction of a helical wind of the flexible body about the tube, and a longitudinal axis of the proximal portion proximal to the at least one bend is transverse to a longitudinal axis of the distal portion distal to the at least one bend. A flexibility of a portion of the medical device having the proximal portion differs from a flexibility of a portion of the medical device having the distal portion, due to the arrangements of the proximal portion and distal portion on the tube.

In another example, a medical device may include a tube and a circuit having a flexible body including a proximal portion and a distal portion that is angled relative to the proximal portion. The distal portion having a plurality of branches each including an array of electrodes configured to provide an electrical charge for stimulating tissue. The flexible body is configured to engage the tube with the proximal portion disposed over the tube in a helical configuration, and the distal portion is disposed over the tube in a linear configuration, such that the plurality of branches is arranged substantially parallel to a longitudinal axis of the tube.

Any of the systems or methods disclosed herein may include any of the following features. The plurality of branches are positioned about a circumference of the tube at spaced intervals. The circuit is configured to modify a flexibility of the tube when the flexible body engages the tube, with the flexibility varying between a segment of the tube having the proximal portion and a segment of the tube having the distal portion.

It may be understood that both the foregoing general description and the following detail description are exemplary and explanatory only and are not restriction of the invention, as claimed.

BRIEF DESCRIPTION OF THE DRAWINGS

The accompanying drawings, which are incorporated in and constitute a part of this specification, illustrate non-limiting embodiments of the present disclosure and together with the description serve to explain the principles of the disclosure.

FIG. 1 illustrates a side view of an exemplary circuit device including a series of electrical and conductive components, according to various embodiments of the present disclosure;

FIG. 2 illustrates a partial side view of the circuit device of FIG. 1 including electrical circuitry associated with the electrical and conductive components, according to one or more embodiments of the present disclosure;

FIG. 17A illustrates a partial side view of the circuit device of FIG. 17 with the distal segment including a bend, according to one or more embodiments of the present disclosure;

FIG. 22 illustrates a side view of another exemplary circuit device including an angled intermediate segment formed of a pair of branches and an angled distal segment formed of a pair of branches, according to one or more embodiments of the present disclosure;

FIG. 23 illustrates a side view of an exemplary circuit device including an electrical circuit at a proximal end, according to one or more embodiments of the present disclosure.

DETAILED DESCRIPTION

Figure 3:
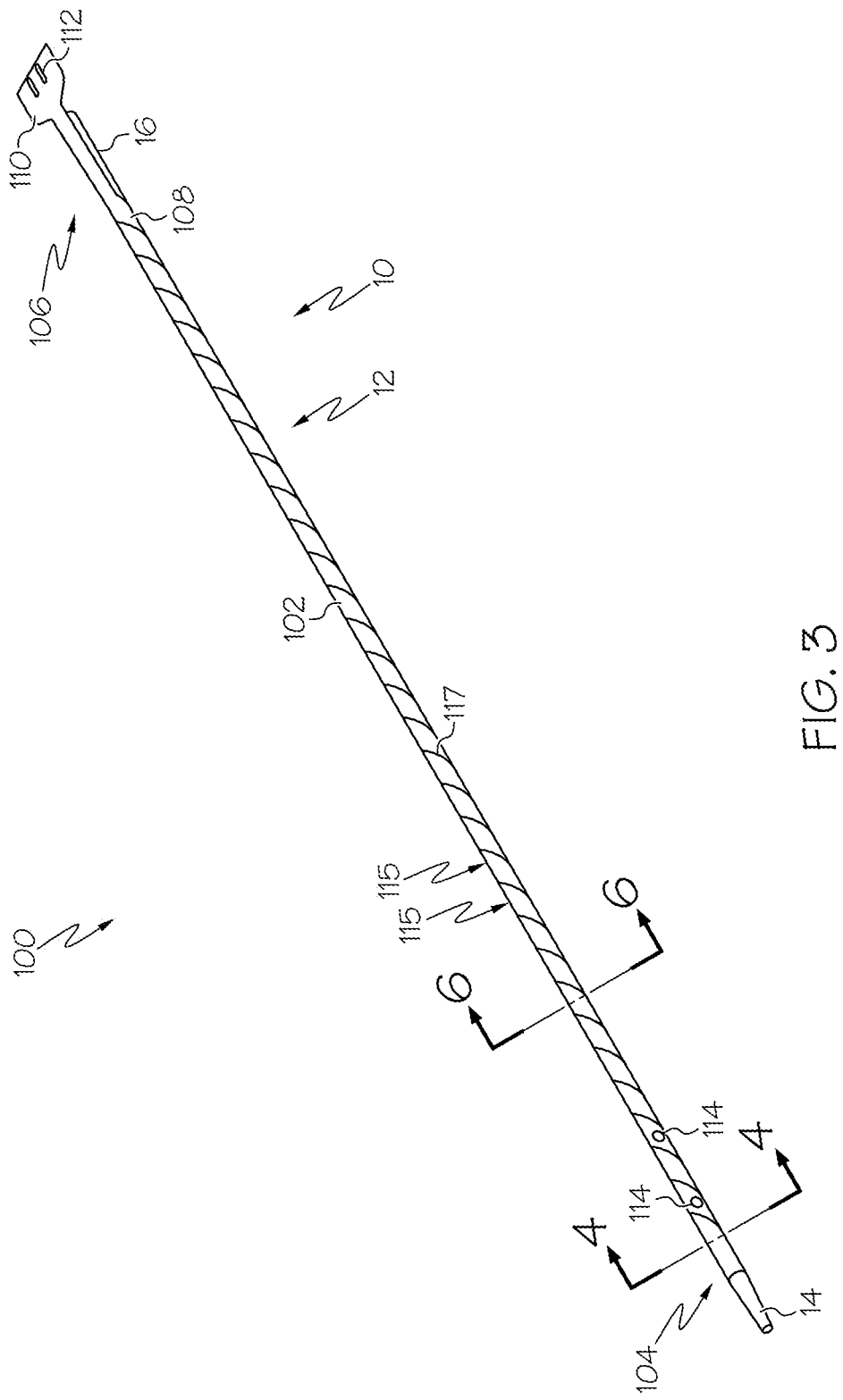
FIG. 3 illustrates a perspective view of the circuit device of FIG. 1 attached to a medical device in a helical configuration, according to various embodiments.

Throughout the following description, specific details are set forth to provide a more thorough understanding to persons skilled in the art. The following description of examples of the technology is not intended to be exhaustive or to limit the system to the precise forms of any example embodiment. Accordingly, the description and drawings are to be regarded in an illustrative sense, rather than a restrictive sense.

All publications and patent applications mentioned in this specification are herein incorporated by reference in their entirety to the same extent as if each individual publication or patent application was specifically indicated to be incorporated by reference. For example, embodiments of the present disclosure may be used in combination with one or more systems, catheters, apparatuses, and electrodes described in U.S. Pat. Nos. 8,571,662, 9,242,088, 9,333,363, 9,776,005, 10,039,920, 10,293,164, U.S. Pat. Pub. 2015/0045810, U.S. Pat. Pub. 2019/0001126, U.S. Pat. Pub. 2019/0175908, U.S. Pat. Pub. 2019/0038894, and/or U.S. Pat. Pub. 2020/0147364; the disclosures of all of which are hereby incorporated by reference.

Further aspects of the disclosures and features of example embodiments are illustrated in the appended drawings and/or described in the text of this specification and/or described in the accompanying claims. It may be understood that both the foregoing general description and the following detailed description are exemplary and explanatory only and are not restrictive of the invention, as claimed.

As used herein, the terms "comprises," "comprising," "including," "having," or other variations thereof, are intended to cover a non-exclusive inclusion such that a process, method, article, or apparatus that comprises a list of elements does not include only those elements, but may include other elements not expressly listed or inherent to such a process, method, article, or apparatus.

Additionally, the term "exemplary" is used herein in the sense of "example," rather than "ideal." As used herein, the term "proximal" means a direction closer to an operator and the term "distal" means a direction further from an operator. The term "approximately" or like terms (e.g., "about," "substantially") encompass values within 10% of the stated value.

Reference will now be made in detail to examples of the present disclosure described above and illustrated in the accompanying drawings. Wherever possible, the same reference numbers will be used throughout the drawings to refer to the same or like parts.

FIG. 1 shows a circuit device 100 according to an example of the present disclosure. Circuit device 100 may include a flexible body 102 having a longitudinal length defined between a distal end 104 and a proximal end 106. Flexible body 102 may include a flexible, planar substrate defined by an exterior surface 101 and an interior surface 103 (FIG. 2). In the example, flexible body 102 may generally include a linear configuration between distal end 104 and an intermediate portion of flexible body 102 distal of proximal end 106. Additionally, flexible body 102 may have a substantially constant and nominal width between distal end 104 and proximal end 106.

Flexible body 102 may include a bend 108 adjacent to proximal end 106 such that proximal end 106 may have a transverse alignment relative to the intermediate portion of flexible body 102 and distal end 104 (the axis of end 106 is transverse to the axis of the intermediate portion). As described further herein, bend 108 may form an angle that aligns a longitudinal axis of proximal end 106 with a central axis of a medical device. Flexible body 102 may further include a proximal tab 110 at proximal end 106 that may have a width that is relatively greater than a width of flexible body 102 at distal end 104 and/or the intermediate portion. Proximal tab 110 may be sized and/or shaped to receive one or more circuitry components thereon, such as conductive pads 112.

Flexible body 102 may be formed of a flexible material having pliability properties such that circuit device 100 may be configured to deform a shape, geometry, and/or configuration of flexible body 102. For example, flexible body 102 may be formed of Liquid Crystal Polymer (LCP), thermoplastics, polyimide, PEEK polyester, silicone, other elastomers, and the like. Flexible body 102 may be construed of multiple layers of materials, such as, for example, electrically conductive and/or non-conductive materials. As described in further detail below, circuit device 100 may be configured to engage a medical device and flexible body 102 may be configured to conform to a profile of the medical device when attached thereto.

Still referring to FIG. 1, circuit device 100 is an electrical connection device that may include a flexible printed circuit board and/or a flex ribbon circuit. For example, circuit device 100 may include flexible circuitry on flexible body 102, such as one or more (e.g., a plurality) electrical and/or conductive components including conductive pads 112 and electrodes 114. In the present example, circuit device 100 includes a pair of electrodes 114 patterned on exterior surface 101 adjacent to distal end 104 and a pair of conductive pads 112 patterned on exterior surface 101 adjacent to proximal end 106. Conductive pads 112 are included on proximal tab 110, and circuit device 100 may include at least one conductive pad 112 for each electrode 114 on flexible body 102.

Conductive pads 112 may be configured to connect electrodes 114 to an ancillary device (e.g., a programmable energy delivery system, a power source, etc.) for transmission of an electric current thereto. Electrodes 114 may be configured to treat a target site of a subject (e.g., a patient) when receiving the electrical current from the ancillary device. For example, electrodes 114 may be operable to stimulate a target site (e.g., a nerve, ganglia, etc.), deliver energy to tissue (e.g., thermal, electrical, etc.), and/or sense a physiologic parameter from or at the target site when distal end 104 is positioned at the target site.

Still referring to FIG. 1, electrodes 114 may form one or more stimulation arrays that are wired or wirelessly connected to one or more circuits, processors, devices, systems, applications, units, or controllers. Each electrode 114 of the stimulation array may include one or more nodes for delivering stimulation. As described in further detail herein, electrodes 114 may be supported on a medical device (e.g., an intravenous catheter, a guidewire, a stimulation lead, a needle, a probe, a lead, a patch, etc.) and may be configured to be placed on, or inserted into, a patient (e.g., a neck, torso, blood vessel, etc.) or placed on the surface of the skin. It should be understood that additional and/or fewer electrodes 114 of varying shapes and/or sizes may be included on flexible body 102 than those shown and described herein.

Electrodes 114 may be positioned along exterior surface 101 in various complex arrangements relative to one another to form high current densities along flexible body 102. It should be appreciated that flexible body 102 may be configured to permit enhanced variety in positioning electrodes 114 axially and radially along a circumference of a medical device (e.g., a catheter) when circuit device 100 is attached thereto. Stated differently, a position of electrodes 114 may not be limited by a structure of a medical device, such as, for example, a geometry of an inner lumen of the medical device, due to the incorporation of electrodes 114 on circuit device 100 in lieu of the medical device.

Electrodes 114 may be configured to deliver stimulation as monopolar, bipolar, tripolar, or other multipolar electrodes. As used herein, a stimulation transmitted by electrodes 114 may refer to an electrical signal transmitted by a single electrode 114 (anode) to the ground reference (cathode) that is positioned away from the anode to generate a larger electrical field (monopolar electrical stimulation); an electrical signal transmitted from an anode electrode 114 to a cathode electrode 114 (bipolar stimulation); or an electrical signal transmitted from one or more electrodes 114 to one or more other electrodes 114 (multipolar electrical stimulation) (e.g., from a cathode to two anodes, from two cathodes to an anode, or from a cathode to three or more anodes, or from two cathodes to two anodes, etc.). As any of these electrode combinations and configurations are contemplated, for clarity when referring to one or more processes, methods, or modes of operation, such types of electrical signal transmission may all be referred to as a stimulation transmitted by one electrode 114 or a combination of electrodes 114.

Referring now to FIG. 2, interior surface 103 of flexible body 102 is shown and a relative position of conductive pads 112 and electrodes 114 on exterior surface 101 are schematically depicted for illustrative purposes. Each conductive pad 112 may be connected to a corresponding electrode 114 via a conductive (electrical) lead 116 extending along interior surface 103. Conductive leads 116 may include circuit traces patterned on interior surface 103, and conductive leads 116 may define a conductive pathway between conductive pads 112 and electrodes 114.

Conductive leads 116 may be configured to negate a necessity of including wires to connect electrodes 114 to a power source, thereby simplifying a circuitry construction of circuit device 100. Each conductive lead 116 may include a distal end positioned adjacent to distal end 104 at a location of electrode 114, and a proximal end positioned adjacent to proximal end 106 at a location of conductive pad 112.

It should be understood that conductive pads 112 and electrodes 114 may be patterned on exterior surface 101 opposite of conductive leads 116 on interior surface 103. Circuit device 100 may include at least one conductive lead 116 for each corresponding pair of conductive pads 112 and electrodes 114 on flexible body 102. An electrical current received by circuit device 100 from an ancillary device (e.g., a power source, etc.) at conductive pads 112 may be delivered to electrodes 114 via conductive leads 116.

In some embodiments, flexible body 102 may include a shape memory alloy wire (not shown) disposed along exterior surface 101 and/or interior surface 103. The wire may be configured to selectively manipulate a shape of flexible body 102, such as, for example, in response to receiving a current and/or an increase in temperature (e.g., from a subject's body, etc.). As described in further detail below, the wire may be operable to adjust a shape of a medical device when circuit device 100 is attached thereto. Control of a shape and/or orientation of the medical device may allow for control of a stimulation field generated by electrodes 114. As noted above, a shape and intensity of a stimulation field may be further controlled by a shape, size, charge, and/or arrangement of electrodes 114 relative to one another along flexible body 102.

Referring to FIG. 3, circuit device 100 is shown disposed over and attached to a medical device 10. Medical device 10 may include a tubular body 12 having a longitudinal length defined between a distal tip 14 and a proximal tip 16. In some embodiments, medical device 10 may include a catheter, a flexible tube, a sheath, a scope, a lead, a probe, a hypotube, a patch, a cable, and/or various other flexible instruments suitable for intravascular, percutaneous, or transcutaneous delivery. In the example, medical device 10 may include an intravenous catheter having a flexibility sufficient to traverse a subject's blood vessels, esophagus, nasal cavity, and/or various other anatomical lumens, passageways, etc.

In some examples, tubular body 12 may be formed of an extruded polymer having homogenous properties (e.g., a constant thickness, etc.) between distal tip 14 and proximal tip 16 such that tubular body 12 may include a substantially consistent flexural strength along the longitudinal length. In other embodiments, circuit device 100 may be configured to increase a material thickness along certain portions of tubular body 12 and/or include one or more structures that modify the properties of tubular body 12 (e.g., increase or decrease rigidity or flexibility, affect shape memory, etc.) when flexible body 102 is attached thereto.

Tubular device 12 may include one or more lumens (see FIG. 6) defined between distal tip 14 and proximal tip 16. The one or more lumens may be sized, shaped, and configured to receive one or more devices therein, including, but not limited to, an irrigation device, an ultrasound device, an optical device, an imaging device, a sensing device, an illumination device, a guidewire, a diagnostic or therapeutic device, etc., and/or receive a fluid. Distal tip 14 may include an opening in communication with the one or more lumens of tubular body 12 such that the one or more devices received within the lumens may extend outwardly from distal tip 14 through the opening. Distal tip 14 may have an atraumatic configuration to minimize injury to tissue when traversed through a subject.

Circuit device 100 may be disposed about medical device 10 and secured to an outer surface of tubular body 12. Flexible body 102 is configured to have a first configuration prior to being secured to an exterior of tubular body 12 and a second configuration having a shape that conforms to a profile of the tubular body 12 with electrodes 114 secured to an exterior of tubular body 12. Accordingly, flexible body 102 may be configured to conform to a geometry of tubular body 12 (e.g., cylindrical). In the example, distal end 104 may be secured to a distal portion of tubular body 12 adjacent to and proximal of distal tip 14. Proximal end 106 may be secured to a proximal portion of tubular body 12 adjacent to and distal of proximal tip 16.

Circuit device 100 may be attached to medical device 10 at one or more locations and by various methods, including, for example, bonding flexible body 102 to an exterior of tubular body 12 (e.g., thermal bonding, thermal welding, thermal lamination, ultrasonic welding, laser welding, RF welding, adhesive bonding, solvent bonding, chemical reaction, and/or solvent bonding). It should be appreciated that a resulting flexural property of tubular body 12 may vary based on various factors, including but not limited to, the method of bonding flexible body 102 thereto, a configuration/arrangement of flexible body 102 relative to tubular body 12, and/or a material composition of flexible body 102. In some embodiments, circuit device 100 may be treated to modify the surface properties of flexible body 102 prior to limitation or bonding onto tubular body 12. Examples of surface treatments may include, but are not limited to, micro-blasting, sand blasting, plasma treatment, chemical etching, filing, grinding, electroplating, thermal spraying, physical vapor deposition, electron beam heating, and more.

The resulting flexural properties of the combined assembly of medical device 10 and circuit device 100 may influence the performance of tubular body 12 during a procedure. For example, the flexural properties may be decreased in specific regions along a longitudinal length of tubular body 12 to influence where tubular body 12 may bend during a procedure, such as when navigating through anatomical structures of a subject. The flexural properties may be decreased to further reduce stress along specific regions of tubular body 12 that may be maintained in a bent configuration when positioned at a target site within a subject. In some embodiments, the flexural properties may be configured to influence a direction of bending tubular body 12.

Still referring to FIG. 3, flexible body 102 may be disposed about tubular body 12 in various arrangements and/or configurations to position electrodes 114 at a desired location relative to tubular body 12. It should be appreciated that electrodes 114 may be positioned at a variety of axial locations along tubular member 12, and/or various radial positions around tubular member 12, to achieve varying physical properties of medical device 10. For example, flexible body 102 may be attached to tubular body 12 in a manner that may be parallel or transverse (e.g., perpendicular) to a central axis of tubular body 12.

In the present example, flexible body 102 may be attached to tubular body 12 at an angle that is transverse to a central axis of tubular body 12 such that circuit device 100 is secured to medical device 10 in a helical configuration. Flexible body 102 may be wound about the central axis of tubular body 12 in a plurality of helical winds 115 (i.e., helix turns). A pair of adjacent helical winds 115 may form a gap 117 therebetween. Electrodes 114 may be wrapped around a circumference of tubular body 12 and flexible body 102 may conform to a profile of tubular body 12.

Still referring to FIG. 3, flexible body 102 may be helically wrapped with a substantially constant pitch and uniform gaps 117 between adjacent helical winds 115. Accordingly, circuit device 100 may have constant flexural properties along a longitudinal length of flexible body 102. In other embodiments, flexible body 102 may be helically wrapped to have varying pitches and/or gaps (see FIGS. 16-17), including no gaps, to selectively adjust the flexural properties of circuit device 100 at various locations along tubular body 12.

A substantial length of tubular body 12 may be disposed underneath flexible body 102. As described above, bend 108 may form an angle between an intermediate portion of flexible body 102 and proximal end 106 to align proximal end 106 with the central axis of tubular body 12. Accordingly, the plurality of helical winds 115 may terminate at bend 108 such that proximal end 106 may extend substantially parallel to tubular body 12. Stated differently, the helical configuration of flexible body 102 may extend from distal end 104 to bend 108 such that proximal portion 106 may be maintained in a non-helical (e.g., linear) configuration that is parallel to the central axis of tubular body 12.

Still referring to FIG. 3, distal tip 14 may be positioned relatively distal of distal end 104, and proximal tip 16 may be positioned proximal of bend 108 and relatively distal of proximal tab 110. Accordingly, proximal tab 110 may extend proximally of proximal tip 16. As described in greater detail below, proximal tab 110 may extend beyond proximal tip 16 for receipt within a hub 140 (see FIG. 9).

Figure 4:
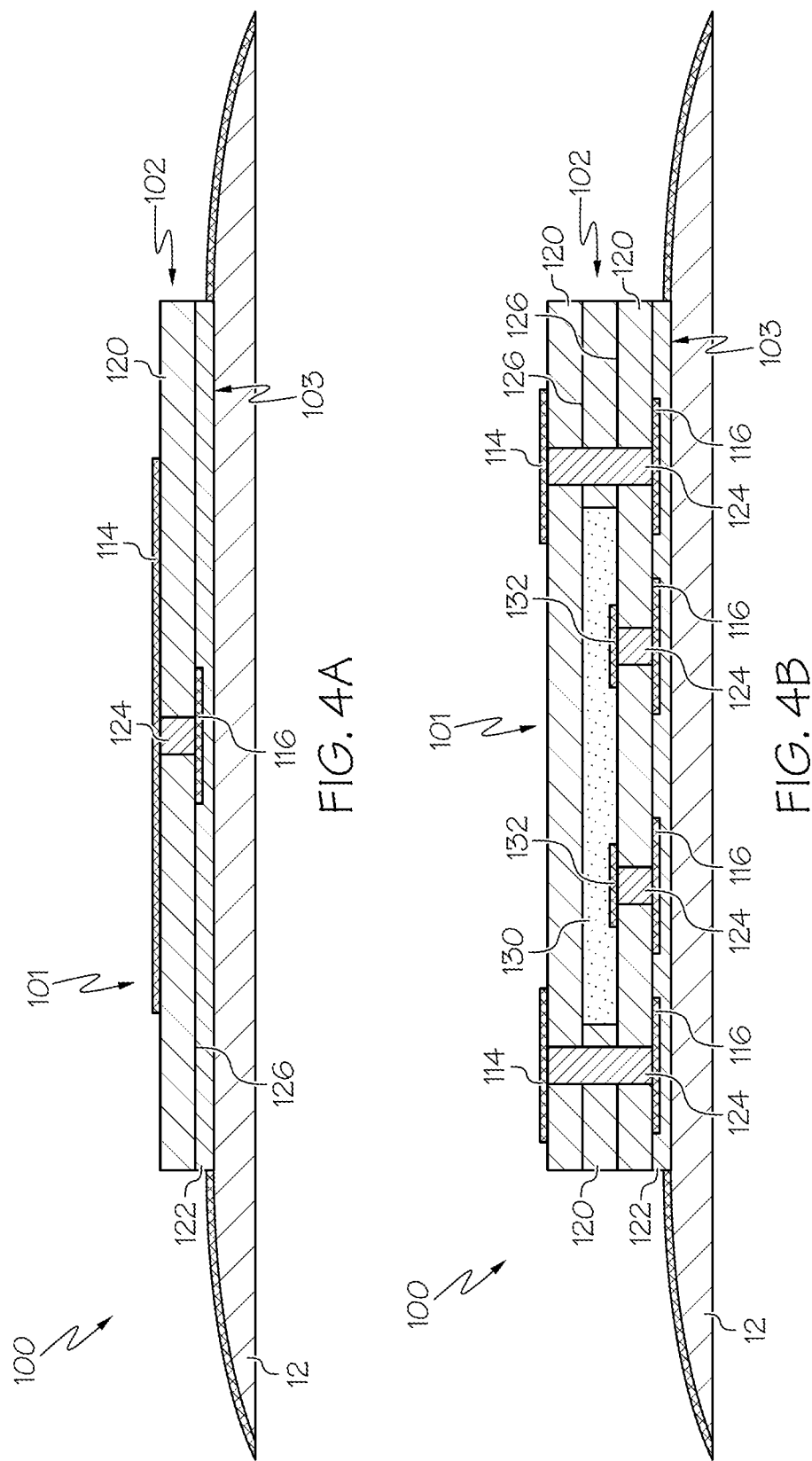
FIG. 4A illustrates a cross-sectional view of the circuit device of FIG. 1 attached to the medical device of FIG. 3 and including an electrode, according to one or more embodiments.
FIG. 4B illustrates a cross-sectional view of the circuit device of FIG. 1 attached to the medical device of FIG. 3 and including a device component, according to one or more embodiments.

FIGS. 4A-4B are exemplary partial cross-sectional views of FIG. 3, taken at line 4-4. Referring now to FIG. 4A, an exemplary flexible circuitry construction of flexible body 102 is schematically depicted. For example, flexible body 102 may be formed of one or more electrically conductive and/or insulating materials that form conductive pathways between distal end 104 and proximal end 106. Electrode 114 may define a first conductive layer and conductive lead 116 may define a second conductive layer. Circuit device 100 may further include a base layer 120 formed of one or more dielectric substrate films disposed between the pair of electrically conductive layers. Electrode 114 and conductive lead 116 may be affixed to base layer 120 by, for example, depositing, adhering, and/or bonding the layers together.

In some examples, base layer 120 may have a thickness ranging from about 12 microns to about 125 microns. The one or more dielectric substrate films forming base layer 120 may comprise polymer materials, such as, for example, polyimides, polyesters, liquid crystal polymer (LCP), polyethylene naphthalate, polyvinyliden fluoride, polyetherimide, various fluoropolymers (FEP), etc. In some examples, the polymer materials comprising base layer 120 may be biocompatible with tissue.

Still referring to FIG. 4A, the one or more electrically conductive materials forming electrode 114 and/or conductive lead 116 may comprise, for example, copper, gold, graphene, silver, nickel, platinum, platinum-iridium alloy, iridium oxide, titanium nitride, tungsten, alloys, and/or combinations thereof. In other embodiments, conductive lead 116 may be patterned to form various other electrical circuit elements.

For example, the electrically conductive layer forming conductive lead 116 may be patterned using additive processes (e.g., spraying, sputtering, sputter coating, screen printing, stenciling, electrodeposition, electroplating, atomic layer deposition, and/or digital printing, etc.) and/or subtractive processes (e.g., chemical etching, laser etching, and/or laser machining, etc.). Stated differently, flexible body 102 may include the desired electrical circuit traces and/or other electrical circuit elements by selectively removing a portion of conductive lead 116 via one or more of the additive and/or subtractive processes described above.

Still referring to FIG. 4A, electrode 114 may be affixed to an opposing side of base layer 120 as conductive lead 116. Further, electrode 114 may be interconnected with conductive lead 116 and through base layer 120 by a via 124. Via 124 may be a hole formed through base layer 120 by, for example, drilling, laser cutting, and/or mechanically puncturing base layer 120 and/or the pair of opposing conductive layers (e.g., electrode 114, conductive lead 116). In some embodiments, circuit device 100 may include a plurality of vias 124, each of which may be filled with a conductive material configured to connect electrode 114 and conductive lead 116 through base layer 120.

In some embodiments, an exterior surface of electrode 114 and/or conductive lead 116 may have one or more materials and/or finishes included thereon, such as, for example, via additive processing (e.g., electrodeposition, electroplating, electroless plating, sputtering, sputter coating, etc.). The one or more materials and/or finishes included on electrode 114 and/or conductive lead 116 may include, for example, nickel, silver, gold, platinum, platinum iridium, titanium nitride, and the like. The one or more materials and/or finishes may be operable to enhance a conductivity, corrosion resistance, and/or a biocompatibility of circuit device 100.

Additionally, an insulative or non-conductive substrate, layer, coating, film, and/or finish may be attached (e.g., bonded, soldered, etc.) to flexible body 102 to provide insulation of electrode 114, conductive lead 116, and/or base layer 120. Such materials may include, for example, tetrafluoroethylene (TFE), polytetrafluoroethylene (PTFE), polyimide, polyetheretherketone (PEEK) polyester, silicon, and other various flexible substrates.

Still referring to FIG. 4A, a protective cover layer may be included on circuit device 100 and bonded to base layer 120 and/or conductive lead 116. The protective cover layer may include a film and/or finishing (e.g., laminate adhesive layer, etc.) configured to protect the conductive lead 116 (and/or other electrical components) from environmental exposure to moisture, contaminants, mechanical damage, etc., during use of circuit device 100 in a procedure. In the present example, circuit device 100 may include a coverlay film 122 bonded to a surface of conductive lead 116 and base layer 120 with an adhesive 126. Coverlay film 122 may be configured and operable to protect conductive leads 116.

Referring now to FIG. 4B, another exemplary flexible circuitry construction of flexible body 102 is schematically depicted. In this example, flexible body 102 includes a plurality of base layers 120 (e.g., dielectric substrate films) secured to one another by at least one adhesive layer 126 positioned between a pair of adjacent base layers 120. Flexible body 102 may further include a plurality of electrodes 114 disposed over an upper-most base layer 120, with each electrode 114 including a corresponding conductive lead 116 disposed under a lower-most base layer 120 (adjacent to tubular body 12).

Each electrode 114 may be interconnected with conductive lead 116 by a respective via 124 that extends through the plurality of base layers 120 disposed therebetween. Each via 124 may be filled with a conductive material configured to connect the conductive materials (e.g., electrode 114 and conductive lead 116) to one another through the plurality of base layers 120 and adhesive layers 126 positioned therebetween. In the present example, flexible body 102 may include three base layers 120 and one coverlay film 122 disposed beneath base layers 120.

Still referring to FIG. 4B, flexible body 102 may further include a device component 130 embedded between the plurality of base layers 120. Device component 130 may be positioned in alignment with a center base layer 120 and between an upper-most base layer 120 and a lower-most base layer 120. Flexible body 102 may further include one or more conductive layers 132 in contact with device component 130 and one or more (e.g., a plurality) vias 124 (filled with conductive material) connecting conductive layers 132 with corresponding conductive leads 116. It should be understood that circuit device 100 may include a respective conductive pad 112 at proximal end 106 corresponding to each of the plurality of electrodes 114 and device component 130.

Device component 130 may include various systems, including, for example, a sensor, an electronic chip, an integrated circuit, and the like. In some embodiments, device component 130 may be fully enclosed between the plurality of base layers 120; while in other embodiments, at least a portion of device component 130 may be exposed from the plurality of base layers 120. In this instance, device component 130 may be accessible to a subject's tissue and/or fluids during use of circuit device 100 in a procedure. For example, device component 130 may include a sensing system configured to detect a signal (e.g., cardiac signal, impedance, temperature, flow, pressure, chemical composition, blood gas, etc.) from a subject (i.e., a patient) to facilitate determining a position of circuit device 100 therein, and/or to detect stimulation of an anatomical target based on a physical response of the subject.

Although not shown in FIGS. 4A-4B, in some embodiments, an adhesive, a polymer, or other filling material may be included to provide a smooth transition between one or more edges of flexible body 102 and a surface of tubular body 12. By providing a smooth transition, medical device 10 and circuit device 100 may be inserted and/or removed from the subject with minimal resistance and potential for tissue trauma.

In other embodiments, device component 130 may include flex detection circuitry that may be configured to detect the flexure of flexible body 102 during a procedure at various regions along the longitudinal length of tubular body 12. Such information may guide a placement of tubular body 12 and/or provide anatomical information to an operator of medical device 10. For example, device component 130 may include a strain circuit, a piezo circuit, and/or various other sensors configured to measure a compression and/or expansion (e.g., lateral extension, longitudinal elongation, etc.) of opposite surfaces of tubular body 12 to determine a two or three-dimensional spatial orientation (e.g., distance, rotation, etc.) of tubular body 12 relative to a subject.

Figure 5:
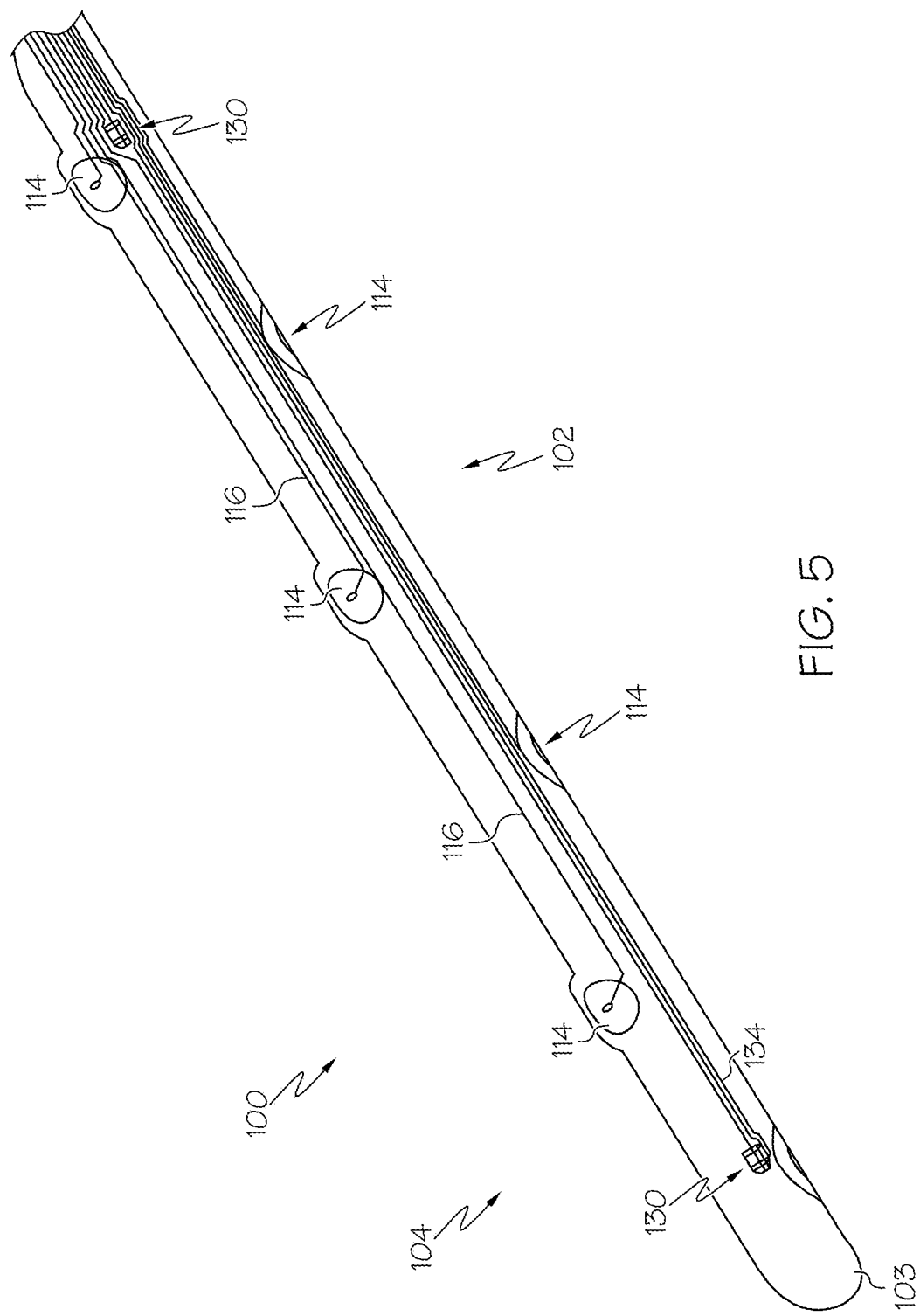
FIG. 5 illustrates a perspective view of the circuit device of FIG. 1 including a device component, according to one or more embodiments of the present disclosure.

Additionally and/or alternatively, one or more integrated circuits may be directly attached to flexible body 102 to provide further localized smart circuitry. For example, as shown in FIG. 5, one or more device components 130 may be attached (e.g., soldered) to interior surface 103 at various positions along flexible body 102, such as adjacent to distal end 104. In this instance, device components 130 extend laterally outward from interior surface 130, thereby forming a protruding profile relative to interior surface 103.

Circuit device 100 may include a circuit trace 134 along interior surface 103 for each device component 130 included on flexible body 102. Circuit traces 134 may interconnect device components 130 with a corresponding conductive pad 112 at proximal end 106 (FIG. 1). In the present example, medical device 10 may include a longitudinal slot, channel, and/or groove formed along an outer perimeter of tubular body 12 that is sized and shaped to receive the one or more device components 130 when flexible body 102 is secured thereto. The one or more slots on tubular body 12 may receive device components 130 therein to accommodate a flush engagement of flexible body 102 with tubular body 12.

Figure 6:
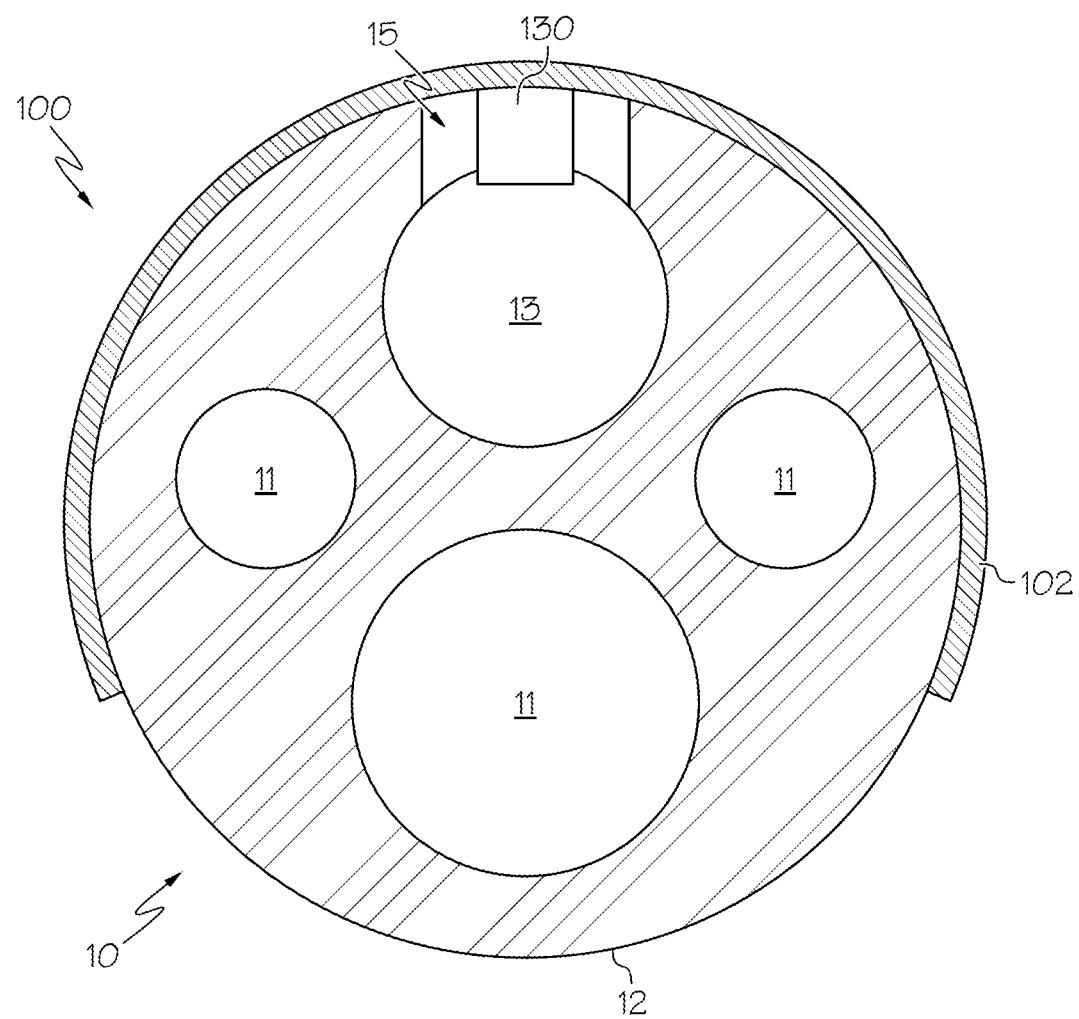
FIG. 6 illustrates a cross-sectional view of the circuit device of FIG. 1 with the device component received within a slot of the medical device of FIG. 3, according to one or more embodiments of the present disclosure.

Referring now to FIG. 6, at least one slot 15 may be formed along at least one surface of tubular body 12. Slot 15 may extend through tubular body 12 and into at least one lumen 13 of tubular body 12. Accordingly, lumen 13 may be exposed to an exterior of tubular body 12 via slot 15. It should be understood that tubular body 12 may include a plurality of other lumens 11 that are separate from the at least one lumen 13 aligned with slot 15. Accordingly, the plurality of lumens 11 are not in fluid communication with lumen 13 or with one another. In other examples, two or more of the plurality of lumens 11 may be interconnected with one another and/or with lumen 13 at one or more locations.

Flexible body 102 may be secured to tubular body 12 such that device component 130 may be aligned with and received in slot 15. Thus, interior surface 103 may be flush against an exterior surface of tubular body 12. It should be appreciated that flexible body 102 may cover and/or encapsulate a majority of tubular body 102. Accordingly, slot 115 may be covered when flexible body 102 is attached to tubular body 12, thereby sealing lumen 13 with interior surface 103. Device component 130 may include, for example, a thermistor sensor, an electronic chip, a resistor, a diode, a capacitor, a strain gauge, a piezoelectric sensor, an integrated circuit, and various other electronic devices.

By way of example, device component 130 may be configured to measure a temperature of a fluid, such as, for example, a fluid disposed within one of the plurality of lumens 11, 13 and/or positioned external of medical device 10. Circuit device 100 may be configured to measure a change in temperature based on the temperature data detected by device component 130. In some examples, circuit device 100 may be configured to measure a flow rate and/or other characteristics of the fluid based on the temperature data sensed by device component 130. In other examples, device component 130 may be configured to heat fluid (e.g., blood, etc.) located external of circuit device 100 and measure a temperature change of the fluid at one or more locations along a longitudinal length and/or lateral width of circuit device 100. For example, at least one location for measuring a temperature change of the fluid may be positioned relatively distal to the heat source (e.g., distal component 130) for determining a flow rate or other properties of the fluid.

Figure 7A:
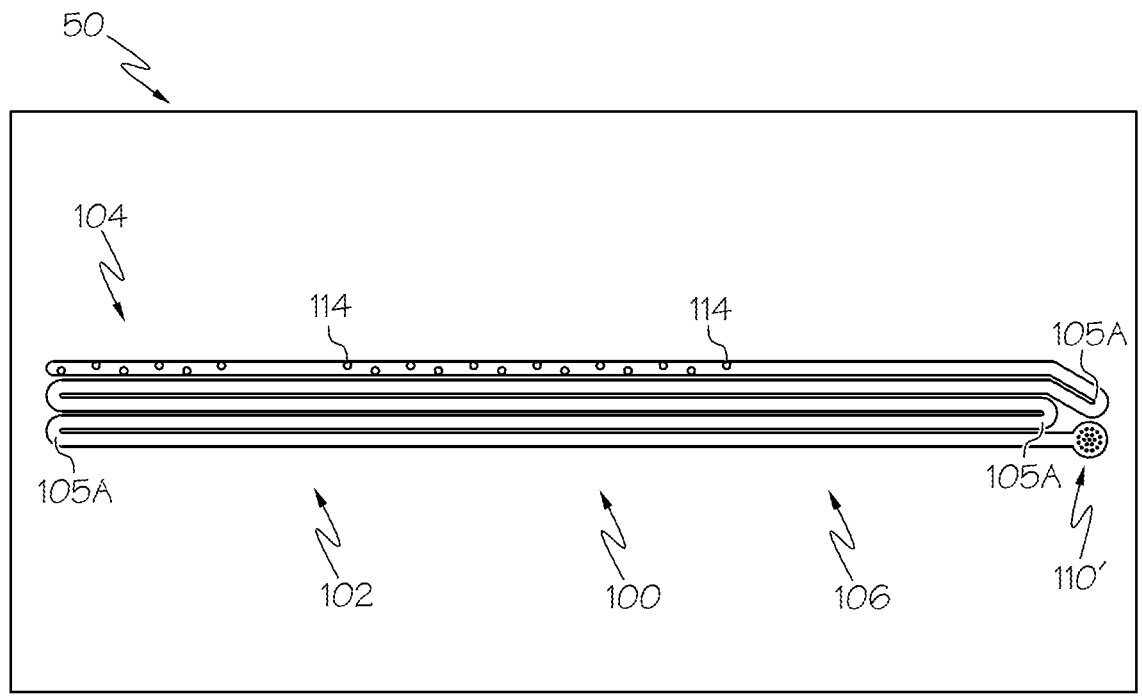
FIG. 7A illustrates a side view the circuit device of FIG. 1 printed on a planar sheet and including one or more curved bends, according to one or more embodiments of the present disclosure.

In some embodiments, as seen in FIG. 7A, circuit device 100 may be printed on a dielectric substrate film in sheet format, such as on a planar sheet 50. Flexible body 102 may be cut from sheet 50 in various desired sizes, shapes, and/or configurations. For example, flexible body 102 may be printed to have a substantially constant width between distal end 104 and proximal end 106. Further, flexible body 102 may be printed to have various suitable lengths between distal end 104 and proximal end 106 in accordance with a longitudinal length of tubular body 12.

Proximal end 106 may be printed on sheet 10 with various configurations, sizes, and/or shapes. For example, proximal end 106 may be printed to include bend 108 having a desired angle. It should be appreciated that bend 108 may define a plurality of angles and/or degrees of curvature between proximal end 106 and an intermediate portion of flexible body 102. Further, proximal end 106 may be printed to include a squared end defining proximal tab 110 (FIGS. 1-3). In other examples, proximal end 106 may be printed to omit bend 108 entirely and/or to include a circular end defining another exemplary proximal tab 110'.

Figure 7B:
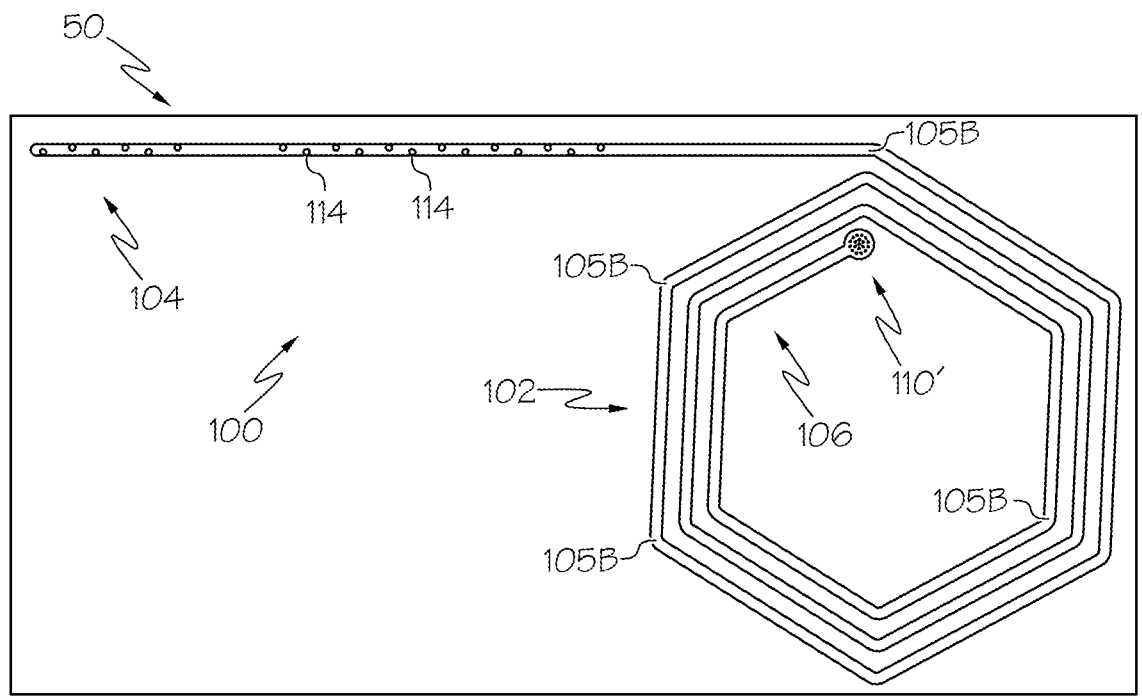
FIG. 7B illustrates a side view of the circuit device of FIG. 1 printed on a planar sheet and including one or more angular bends, according to one or more embodiments of the present disclosure.

Still referring to FIG. 7A, flexible body 102 may be printed on sheet 50 with one or more bends 105A to accommodate various longitudinal lengths. Bends 105A may be sized to minimize material use on sheet 50 when printing circuit device 100 thereon. For example, the one or more bends 105A may range from about 90 degrees to about 180 degrees. In other examples, as seen in FIG. 7B, flexible body 102 may be printed on sheet 50 with one or more bends 105B that range from about 1 degree to about 89 degrees, such as 45 degrees. In this instance, flexible body 102 may be more easily straightened for attachment onto tubular body 102 than when circuit device 100 is printed with the one or more bends 105A (e.g., bends having a greater angle).

Figure 8:
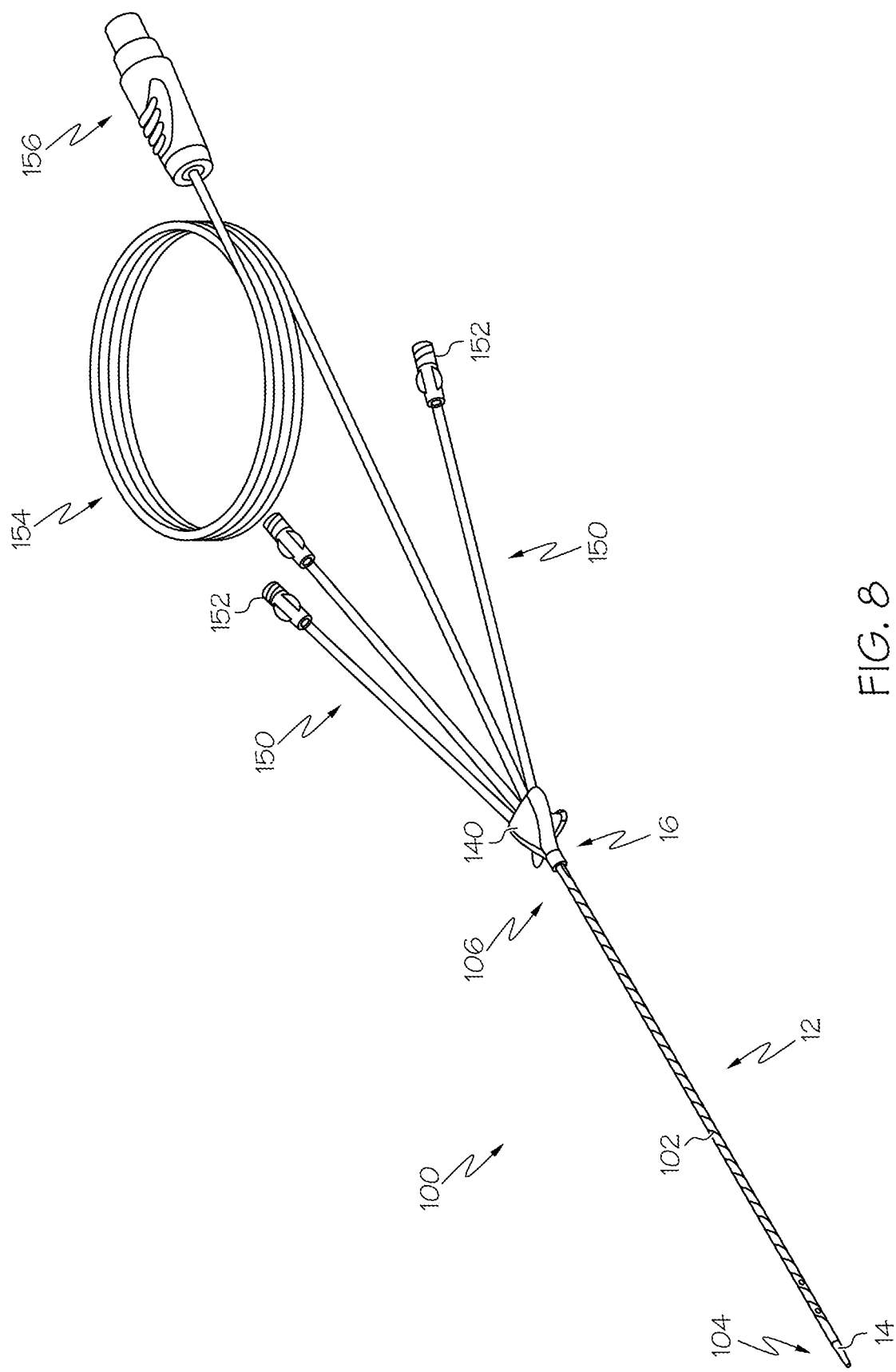
FIG. 8 illustrates a perspective of the circuit device of FIG. 1 attached to the medical device of FIG. 3 and including a hub; according to an embodiment of the present disclosure.

Referring now to FIG. 8, hub 140 may be configured and operable to receive tubular member 12 and flexible body 102 therein. In some embodiments, tubular member 12 and flexible body 102 may be coupled to hub 140; while in other embodiments, hub 140 may be molded over tubular member 12 and flexible body 102. Hub 140 may extend proximally from proximal tip 16 and include one or more extension tubes 150 coupled and/or molded to a proximal end of hub 140. Hub 140 may be configured to interconnect lumens 11 (FIG. 6) with extension tubes 150.

Extension tubes 150 may include a coupling mechanism 152 (e.g., a luer connector, a female adapter, a fitting, and/or other fluid tight connector assemblies) at a distal end of each extension tube 150 for securely coupling an ancillary device (e.g., a tool, a sensor, a cable, a fiber, etc.). Extension tubes 150 may facilitate receipt of the one or more ancillary devices into lumens 11 via hub 140. In some examples, extension tubes 150 may be configured to couple hub 140 to a fluid source for delivering a fluid (e.g., drug, therapeutic agent, etc.) to lumens 11. Extension tubes 150 may be further configured to extract a fluid sample (e.g., blood) collected from medical device 10 and received at hub 140 via lumens 11.

In other examples, extension tubes 150 may receive an ancillary device for monitoring a pressure and/or a temperature (e.g., a sensor) and/or for positioning tubular body 12 within a patient (e.g., a guidewire). Other ancillary devices, such as, for example, optical fibers, ultrasound cameras, intravascular imagers, filters, lasers, lights, and the like may be introduced into lumens 11 through hub 140 and from extension tubes 150.

Still referring to FIG. 8, hub 140 may include a protective sheath 154 secured thereto. Protective sheath 154 may include an electrical connector 156 at a proximal end of protective sheath 154 and may define a channel housing one or more wires and/or cables. As described in further detail herein, the wires may be coupled to electrical connector 156 at a proximal end and be received within hub 140 for connection to flexible body 102 at a distal end.

Figure 9:
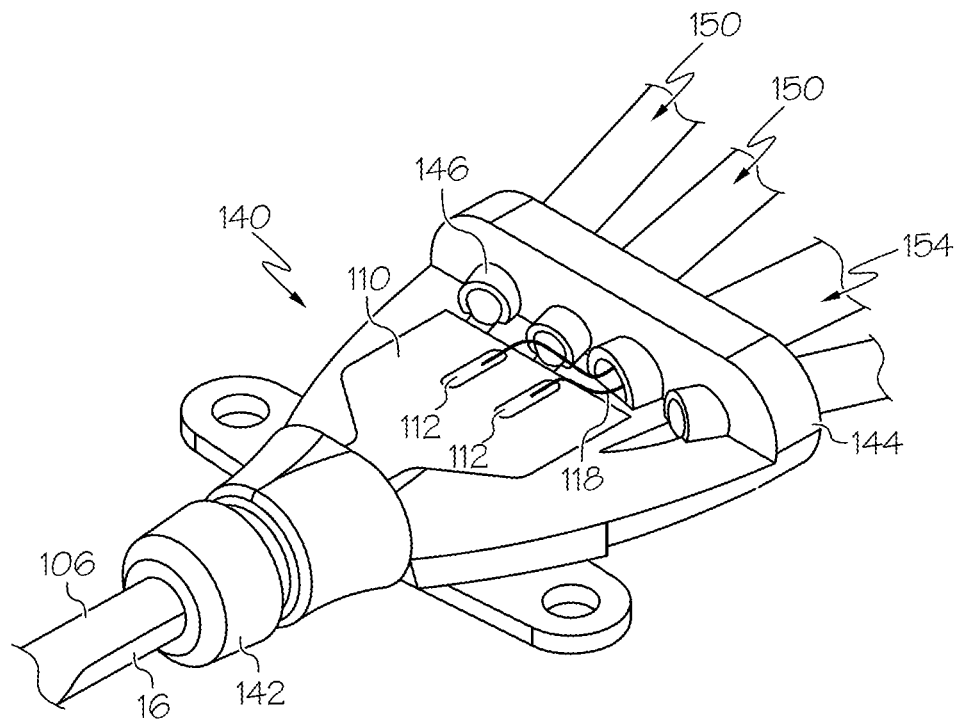
FIG. 9 illustrates a partial perspective view of the circuit device of FIG. 1 electrically coupled to the hub of FIG. 8 in a first configuration, according to one or more embodiments of the present disclosure.

FIG. 9 shows hub 140 with at least a top wall of hub 140 omitted for illustrative purposes. Proximal end 106 may be received through an inlet 142 of hub 140 such that proximal tab 110 is disposed within hub 140. Hub 140 may further include a proximal wall 144, positioned opposite inlet 142, and one or more outlets 146 formed through proximal wall 144. Each extension tube 150 and protective sheath 154 may be coupled to at least one outlet 146. In some examples, hub 140 may receive one or more wires 118 from protective sheath 154 via at least one outlet 146.

It should be appreciated that proximal hub 140 may incorporate one or more features for facilitating an electrical connection with wires 118. The one or more wires 118 may be connected to conductive pads 112 to thereby establish electrical communication between wires 118 and electrodes 114 (e.g., via conductive leads 116). An electrical junction between conductive pads 112 and wires 118 may be formed by various suitable attachment methods, including, for example, solder, laser weld, conductive adhesive, hot bar, interference, friction fits, and/or various other mechanical connection methods.

Further, the electric junction may be reinforced with potting, overmolding, encapsulating, mechanical fasteners, and/or combinations thereof. Each wire 118 may extend through protective sheath 154 and may terminate at electrical connector 156. Electrical connector 156 may be selectively coupled to a power source configured to supply electrodes 114 with electrical power.

Still referring to FIG. 9, hub 140 may include a rigid body defining a fixed and stable interaction point between flexible body 102 and wires 118. Accordingly, hub 140 may be configured to provide strain relief to flexible body 102 and wires 118 at the juncture between proximal tab 110 and wires 118. In some embodiments, the rigid body of hub 140 may be formed of a thermoplastic material having dielectric properties. Thus, hub 140 may be configured to electrically isolate the connections of conductive pads 112 with wires 118.

Figure 10:
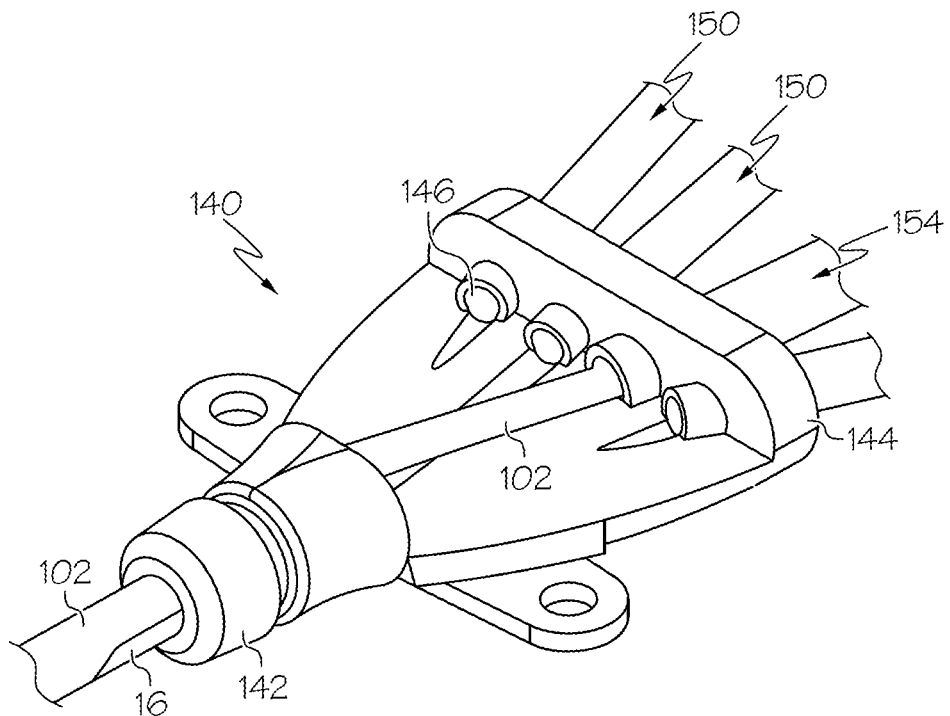
FIG. 10 illustrates a partial perspective view of the circuit device of FIG. 1 electrically coupled to the hub of FIG. 8 in a second configuration, according to one or more embodiments of the present disclosure.

FIG. 10 shows another configuration of circuit device 100 in which at least an intermediate portion of flexible body 102 may be received through inlet 142 and into the respective outlet 146 coupled with protective sheath 154. Accordingly, a portion of flexible body 102 may extend through protective sheath 154 and be received within electrical connector 156. It should be understood that wires 118 may be omitted entirely from the present example such that proximal tab 110 may be directly coupled to the power source.

Figure 11:
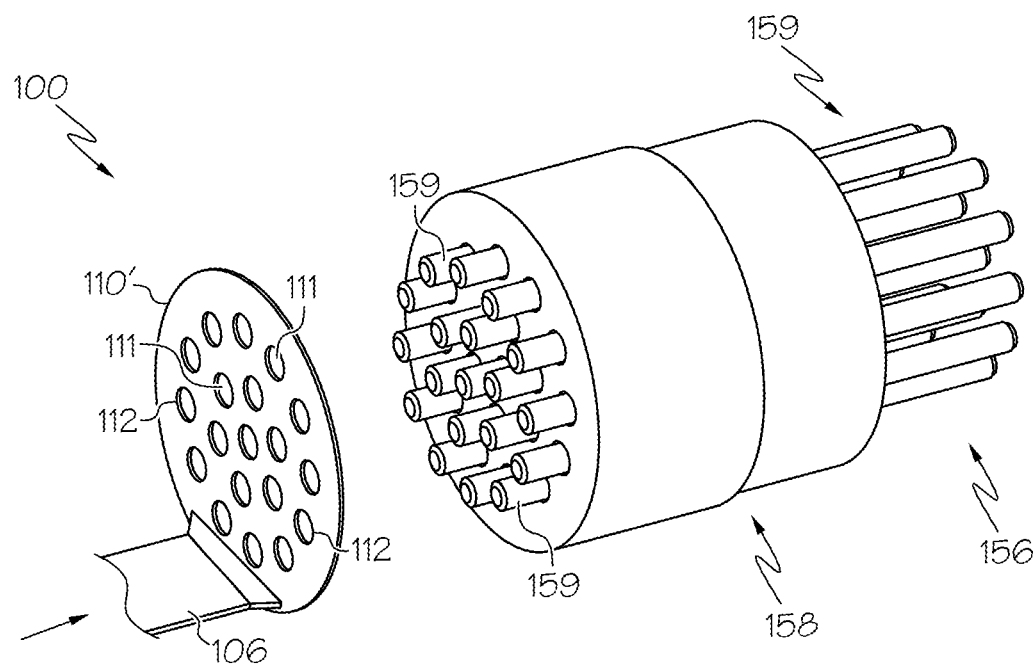
FIG. 11 illustrates a partial perspective view of the circuit device of FIG. 1 electrically coupled to a connector assembly, according to one or more embodiments of the present disclosure.

Referring now to FIG. 11, an alternative exemplary proximal tab 110' is depicted at proximal end 106. In the example, proximal tab 110' may have a circular shape and may extend at an angle relative to proximal end 106. In some embodiments, a position and/or orientation of proximal tab 110' relative to proximal end 106 may be selectively adjustable. Proximal tab 110' may include a plurality of apertures 111 formed therethrough and a plurality of conductive pads 112 positioned about the plurality of apertures 111.

Stated differently, each conductive pad 112 is formed about at least one aperture 111 such that conductive pads 112 may contact a device received through aperture 111. Internal components of electrical connector 156 are depicted with an outer housing of electrical connector 156 omitted for illustrative purposes. Electrical connector 156 may include a socket 158 having a plurality of openings, and a plurality of pins 159 extending through the plurality of openings. Each of the plurality of pins 159 may have a proximal end extending proximally out of socket 158 and a distal end extending distally out of socket 158.

Still referring to FIG. 11, the distal ends of pins 159 may be disposed within the outer housing of electrical connector 156 when in a fully assembled state for connection with proximal tab 110'. The proximal ends of pins 159 may extend outwardly from the outer housing of electrical connector 156 when in a fully assembled state for connection with a power source. Accordingly, the proximal ends of the plurality of pins 159 may define a connector interface of electrical connector 156.

Each of the plurality of apertures 111 may be sized and shaped to receive at least one of the plurality of pins 159. It should be appreciated that a quantity and position of apertures 111 relative to proximal tab 110' may be based on a number and position of pins 159 on socket 158. Circuit device 100 may establish connection with the power source in response to conductive pads 112 contacting pins 159. In some examples, proximal tab 110' may be soldered to socket 158 thereby securing an electrical connection between conductive pads 112 and pins 159.

Figure 12:
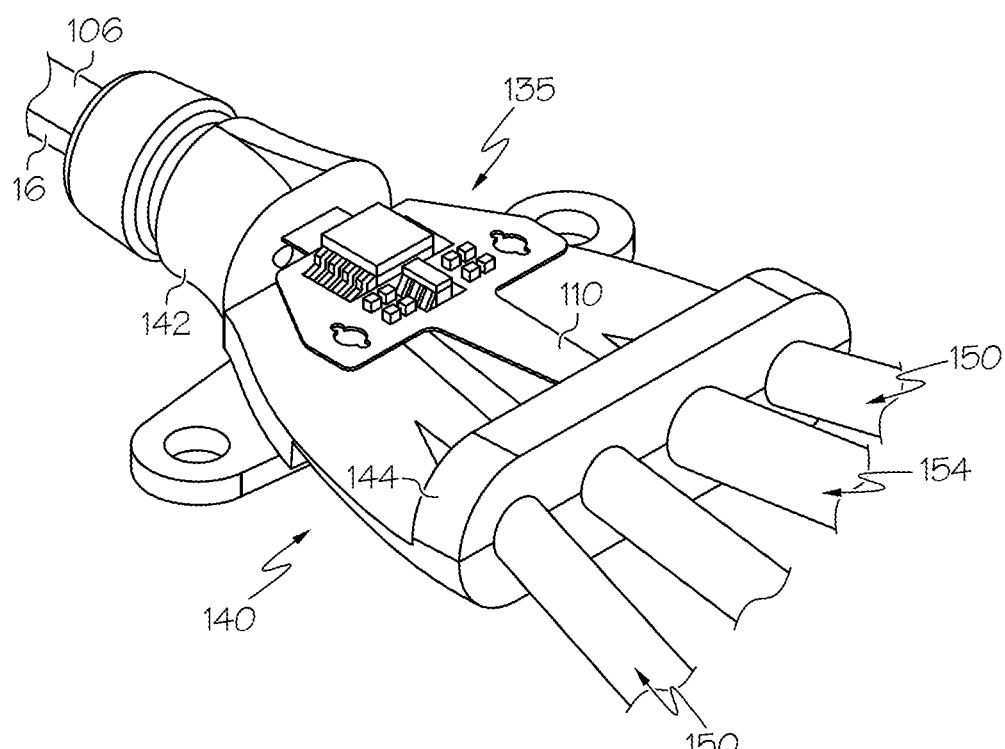
FIG. 12 illustrates of a partial perspective view of the circuit device of FIG. 1 electrically coupled to the hub of FIG. 8 and including a control unit, according to an embodiment of the present disclosure.

In other embodiments, referring now to FIG. 12, circuit device 100 may include an electronic component 135 mounted to flexible body 102 at proximal tab 110. Electronic component 135 may be positioned along exterior surface 101 and encapsulated within hub 140. Electronic component 135 may be secured to flexible body 102 (e.g., at proximal tab 110) via various suitable configurations, including, for example, by a pin and via, an overmolding, potting, and the like. In other embodiments, electronic component 135 may be secured directly to hub 140.

Electronic component 135 may include various suitable devices, including, for example, computer readable storage media such as various types of volatile and non-volatile storage media, including but not limited to, static memory, dynamic memory, a read-only memory chip, a read-write memory chip, an electrically erasable programmable read-only memory (EEPROM), random access memory, flash memory, and the like. In other embodiments, electronic component 135 may include a sensing circuit, a radio-frequency identification (RFID) tag, and other various devices.

For example, electronic component 135 may be configured to store product specific data relating to circuit device 100, such as a serial number, lot number, product configuration, expiration date, calibration constants for device component 130, etc. By way of further example, electronic component 135 may be configured to record use data of circuit device 100 and/or medical device 10, such as dates of activation, variable data from therapy procedure sessions, control unit function algorithms, sensor data of device component 130, etc.

In some embodiments, electronic component 135 may further include a computer system, such as, for example a processor (e.g., a central processing unit (CPU), a graphics processing unit (GPU), or both) in conjunction with the memory described above. For example, the processor may be part of a standard personal computer or a workstation.

The processor may be one or more general processors, digital signal processors, application specific integrated circuits, field programmable gate arrays, servers, networks, digital circuits, analog circuits, or combinations thereof, for analyzing and processing data. The processor may implement a software program, such as programmable code. In other embodiments, the memory may be an external storage device or database separate from electronic component 135.

Still referring to FIG. 12, electronic component 135 may include a controller that is generally configured to accept information from one or more other components of circuit device 100 (e.g., electrodes 114, device component 130, etc.), and process the information according to various algorithms to produce control signals for controlling the other components of circuit device 100.

For example, the controller may accept information from the system and system components, process the information according to various algorithms, and produce information signals that inform a user of circuit device 100 of a procedure status or other information that is being monitored by circuit device 100. The controller may be a digital IC processor, analog processor, or any other suitable logic or control system that carries out control algorithms. Electronic component 135 may be powered by a battery, a direct wire energy, or other suitable power devices. In some examples, electronic component 135 may be configured to communicate with the controller or other components of circuit device 100 via a wired and/or wireless connection.

According to an exemplary method of using circuit device 100 during a procedure, flexible body 102 may be initially bonded to tubular body 12 in one of a plurality of configurations as shown and described above. Proximal tab 110 may be received within hub 140 and coupled to a power source from a connection of conductive pads 114 with electrical connector 156. With circuit device 100 secured to medical device 10, tubular body 12 may be received within a subject (e.g., patient) and navigated toward a target treatment site.

Medical device 10 may be configured to traverse through blood vessels located relatively proximate to one or more nerves (e.g., phrenic nerves, vagus nerves, etc.), muscles, and/or other tissues. A flexibility (or lack thereof) of tubular body 12 may be at least partially determined by the flexural properties of circuit device 100 based on an attachment configuration of flexible body 102 and/or a material composition of flexible body 102. In other words, a geometry and arrangement of circuit device 100 may influence the flexural properties of medical device 10. Medical device 10 may be guided to a target treatment site using one or more devices received within lumens 11 (FIG. 6) via extension tubes 150 and hub 140. For example, medical device 10 may receive a stiffening element (e.g., polymer and/or metallic mandrels), a guidewire, a sensor, an imaging device, an illumination device, a shape memory material (e.g., Nitinol, etc.), and/or other therapeutic or diagnostic medical devices to facilitate placement of circuit device 100.

Accordingly, tubular member 12 may be configured to guide placement of circuit device 100 relative to the target treatment site. Upon arriving at the target treatment site, tubular body 12 may be moved (e.g., translated, rotated, etc.) to position electrodes 114 at a desired location relative to a target object (e.g., a nerve, a muscle, a tissue, etc.). With electrodes 114 positioned adjacent to the target object, activation of the power source may deliver an electrical current through wires 118, conductive pads 112, and to electrodes 114 via conductive leads 116. Electrodes 114 may be configured to stimulate the target object (e.g., a stimulation sufficient to cause a desired physiological result) upon receiving the electrical current from conductive leads 116.

Electrodes 114 may generate therapeutic effects for specific anatomical targets (e.g., nerve stimulation) and a relative position of electrodes 114 to one another on exterior surface 101 may generate one or more charge fields along tubular body 12 for certain therapeutic effects (e.g., asymmetric charge fields). Electrodes 114 may generate a sufficient charge to cause contraction of a diaphragm or other lung-accessory. In some embodiments, electrodes 114 may be positioned along tubular body 12 to form a sensor array antenna configured and operable to detect various forms of stimulation, including, for example, nerve stimulation, muscle stimulation, cardiac stimulation, phrenic nerve activation, diaphragm muscle activation, and more.

In examples where circuit device 100 includes device component 130 (e.g., a sensor, etc.), device component 130 (FIGS. 4B-6) may be positioned toward the target object and activated to detect and/or record one or more characteristics or properties of the target object (e.g., input on whether the requisite stimulation of an anatomical target occurred). Device component 130 may be communicatively coupled to one or more computing systems, such as, for example, via electrical component 135 (FIG. 12) by a wired or wireless connection.

It should be understood that with circuit device 100 secured to an exterior of medical device 10, lumens 11 may be utilized to receive other devices than those included in circuit device 100. Stated differently, circuit device 100 may be operable to maximize an available space within lumens 11 to receive other ancillary devices. For example, circuit device 100 may omit a necessity to route wires internally through tubular body 12 for connecting electrodes 114 to a power source, thereby allowing tubular body 12 to be sized with a smaller minimum diameter.

Further, circuit device 100 includes conductive leads 116 such that use of wires to connect electrodes 114 to a power source may be omitted entirely, whether received within and/or disposed over tubular body 12, thereby further reducing a complexity of medical device 10. Accordingly, tubular body 12 may include a smaller cross-sectional profile than other medical devices (e.g., catheters) sized and shaped to accommodate electrical components (e.g., wires) for including one or more electrodes on the device.

In some embodiments, medical device 10 may sense physiologic parameters of the target treatment site using one or more devices (e.g., intravascular ultrasound (IVUS)) received within lumens 11 (FIG. 6) via extension tubes 150 and hub 140. In other embodiments, medical device 10 may receive devices that vary the flexural properties of tubular body 12 to create zones of stiff and/or flexible regions. For example, a Nitinol wire (not shown) may be received within lumen 11 to alter or control the shape of tubular body 12 in response to the wire receiving a current applied thereto. In this instance, the wire may apply a force onto tubular body 12 from within lumen 11 to a fixed/desired configuration. Removal of the current may terminate the force applied to tubular body 12 by the wire, thereby permitting tubular body 12 to return to a flexible state. In other examples, the shape memory wire may be activated by the heat produced by the subject's body.

FIGS. 13-24 show alternative exemplary circuit devices that may be substantially similar to circuit device 100. A geometry, orientation, and layer construction of the circuit devices relative to an axis of tubular body 12 may influence the flexural properties of medical device 10 in specific regions along the longitudinal length of tubular body 12. It should be understood that the circuit devices described in the examples below may be configured and operable similar to circuit device 100 except for the differences explicitly noted herein, and therefore like reference numerals are used to identify like components. It should further be appreciated that the exemplary circuit devices below may be readily incorporated onto medical device 10.

Figure 13:
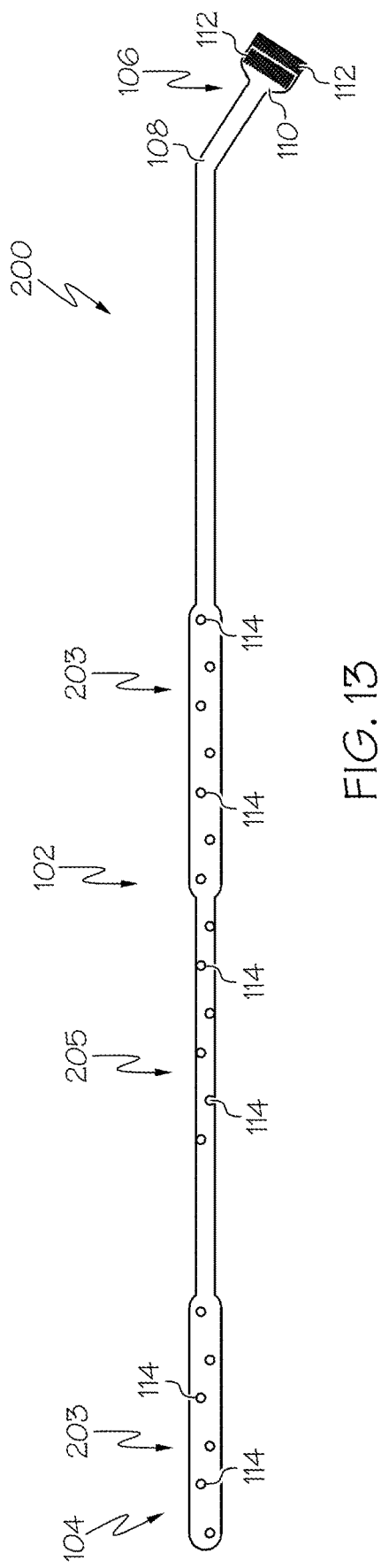
FIG. 13 illustrates a side view of another exemplary circuit device including a widened segment having reduced flexibility, according to one or more embodiments of the present disclosure.

Referring specifically to FIG. 13, an exemplary circuit device 200 is shown in accordance with an example of this disclosure. Circuit device 200 may include a varying geometry and/or width along a longitudinal length of flexible body 102. For example, flexible body 102 may include one or more widened segments 203 between distal end 104 and proximal end 106. In the present example, circuit device 200 may include a pair of widened segments 203 separated from one another along the longitudinal length of flexible body 102 by an intermediate segment 205 having a relatively smaller width.

Flexible body 102 may include layers having a greater thickness along widened segments 203 relative to intermediate segment 205. Widened segments 203 may be configured to impart reduced flexibility on flexible body 102. In the example, widened segments 203 have a relatively smaller longitudinal length than intermediate segment 205, however, it should be understood that various other relative lengths and/or configurations of segments 203, 205 may be included without departing from a scope of this disclosure. In other embodiments, additional and/or fewer widened segments 203 and/or intermediate segments 205 may be included along flexible body 102.

Still referring to FIG. 13, flexible body 102 may include a plurality of electrodes 114 along the pair of widened segments 203 and intermediate segment 205. Thus, proximal tab 110 may include a plurality of conductive pads 112 at proximal end 106 in accordance with a quantity of electrodes 114 on flexible body 102. In some embodiments, one or more of widened segments 203 and/or intermediate segment 205 may exclude any electrodes 114 thereon. In use, widened segments 203 may be configured and operable to reduce the flexural properties of tubular body 12 along the respective portions of tubular body 12 that align with widened segments 203 when circuit device 200 is attached to medical device 10.

Figure 14:
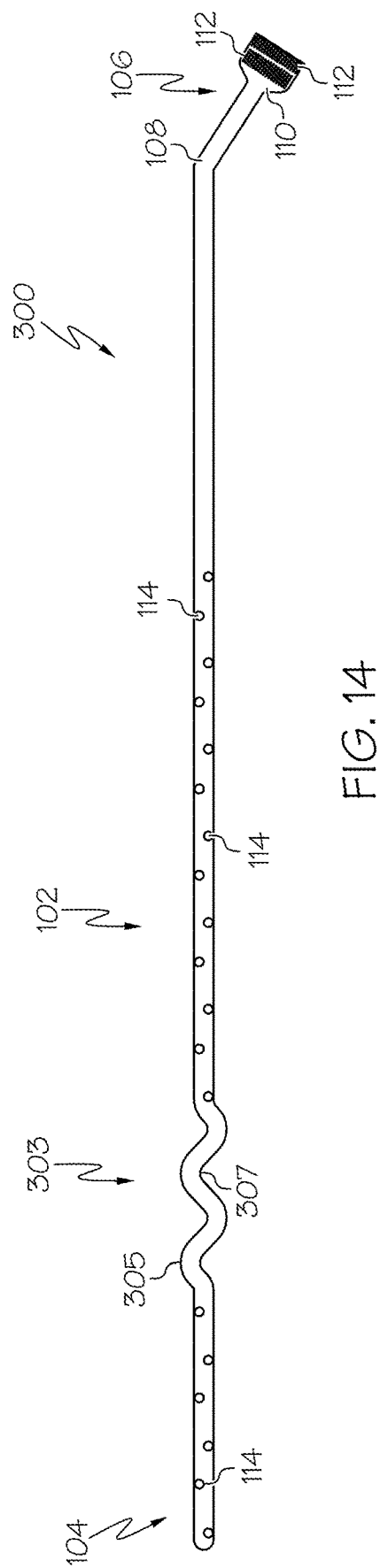
FIG. 14 illustrates a side view of another exemplary circuit device including a non-linear segment having enhanced flexibility, according to one or more embodiments of the present disclosure.

Referring now to FIG. 14, an exemplary circuit device 300 is shown in accordance with another example of this disclosure. Circuit device 300 may include an irregular segment 303 along a longitudinal length of flexible body 102. Irregular segment 303 may be included between distal end 104 and proximal end 106 and may have a geometry and/or configuration that is transverse to a remaining linear geometry of flexible body 102. For example, irregular segment 303 may have a sinusoidal-shape (e.g., S-profile) including a plurality of convex waves 305 (e.g., peaks) and a plurality of concave waves 307 (e.g., troughs). The plurality of waves 305, 307 may have various suitable lengths and/or amplitudes relative to a longitudinal axis of flexible body 102.

In the present example, irregular segment 303 includes a pair of convex waves 305 and a pair of concave waves 307, however, it should be understood that additional and/or fewer waves 305, 307 may be included on irregular segment 303. In other embodiments, flexible body 102 may include additional irregular segments 303 between distal end 104 and proximal end 106. In the present example, irregular segment 303 may be formed along flexible body 102 adjacent to distal end 104 and may include a constant width with a remaining portion of flexible body 102. Further, irregular segment 303 may be configured to increase a flexibility of flexible body 102 relative to the remaining portion of flexible body 102

Still referring to FIG. 14, flexible body 102 may include a plurality of electrodes 114 along portions of flexible body 102 proximal to and distal of irregular segment 303 such that irregular segment 303 excludes electrodes 114 thereon. In some embodiments, one or more of convex waves 305 and/or concave waves 307 may include electrodes 114 thereon. In use, irregular segment 303 may be configured and operable to relatively increase the flexural properties of tubular body 12 along the respective portions of tubular body 12 that align with irregular segment 303 when circuit device 300 is attached to medical device 10.

Figure 15:
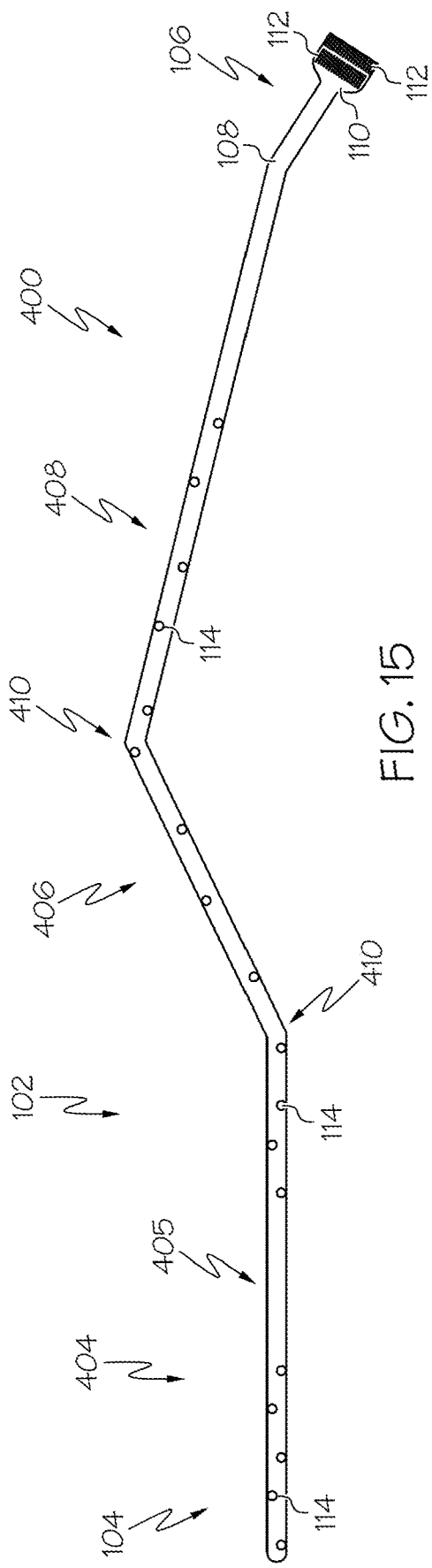
FIG. 15 illustrates a side view of another exemplary circuit device including angular bends, according to one or more embodiments of the present disclosure.

Referring now to FIG. 15, an exemplary circuit device 400 is shown in accordance with another example of this disclosure. Circuit device 400 may include one or more angular changes/bends along a longitudinal length of flexible body 102. For example, flexible body 102 may include a plurality of segments 404, 406, 408 separated from one another by at least one bend 410, respectively. Accordingly, each of the plurality of segments 404, 406, 408 may be positioned and aligned relatively transverse to one another.

In the present example, a distal segment 404 is positioned adjacent to distal end 104, a proximal segment 408 is positioned adjacent to proximal end 106, and an intermediate segment 406 is disposed between distal segment 404 and proximal segment 408. Flexible body 102 may include a pair of bends 410, at least one of which is disposed between distal segment 404 and intermediate segment 406 and another of which is disposed between intermediate segment 406 and proximal segment 406.

Still referring to FIG. 15, each of the plurality of segments 404, 406, 408 may have varying flexural properties relative to one another based on an angle of bends 410 between an adjacent pair of segments. Bends 410 may range from about 1 degree to about 60 degrees and each bend 410 may extend an adjacent pair of segments in a different (or similar) direction and/or angle relative to one another. Further, each bend 410 may include varying angles relative to the one or more other bends 410 on flexible body 102.

In other embodiments, circuit device 400 may include additional and/or fewer segments along flexible body 102 that may be separated by additional and/or fewer bends 410, respectively. Each of the plurality of segments 404, 406, 408 may include one or more electrodes 114; while in some embodiments, segments 404, 406, 408 may omit electrodes 114 entirely.

Figure 16:
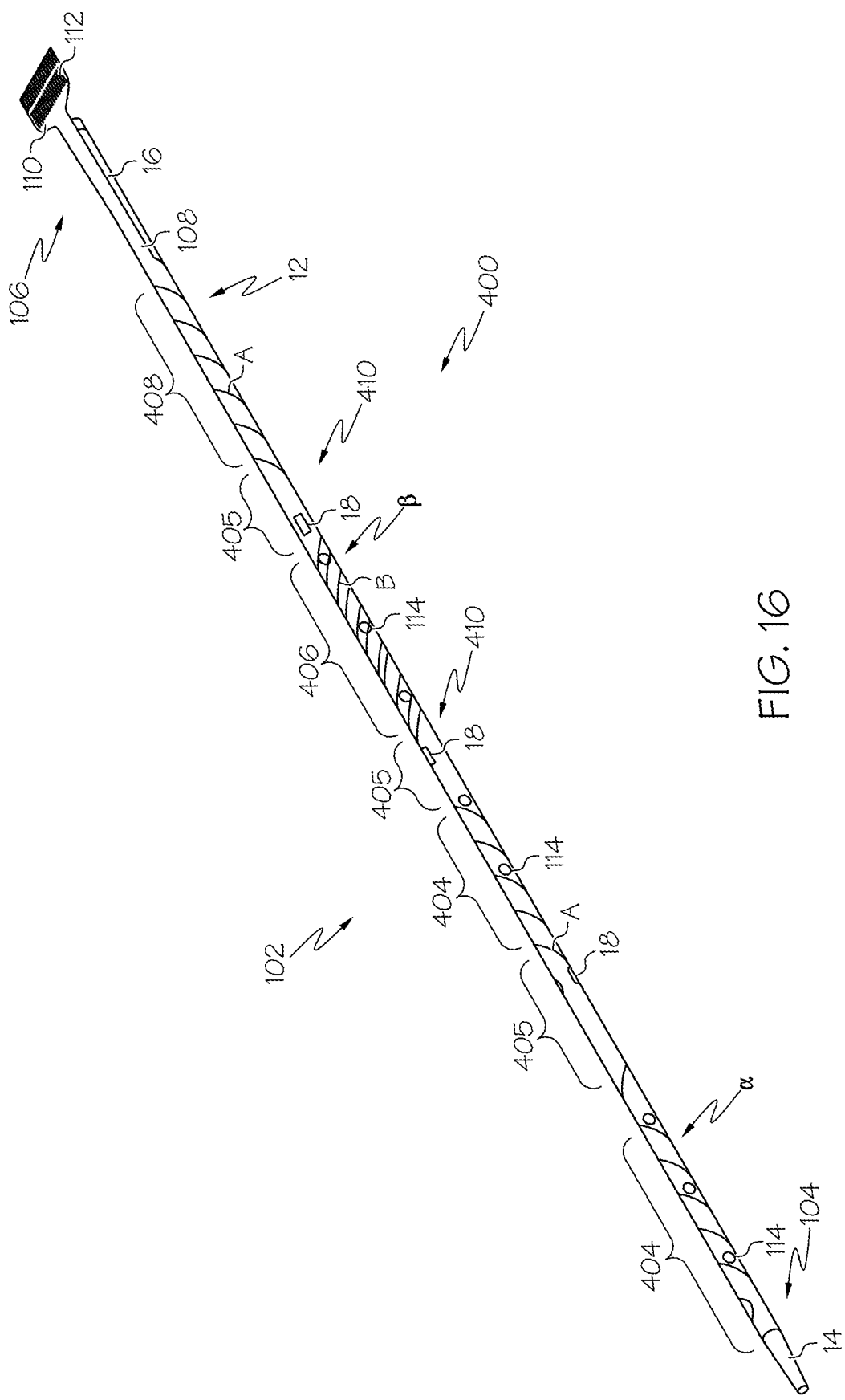
FIG. 16 illustrates a perspective view of the circuit device of FIG. 15 attached to the medical device of FIG. 3 and including a flexible segment (low density) and a rigid segment (high density) between the angular bends to provide variable flexibility and other attributes, according to one or more embodiments of the present disclosure.

Referring now to FIG. 16, each of the plurality of segments 404, 406, 408 may cause the corresponding portion of the overall medical device to have varying flexural properties relative to one another based on an angle of helical wrap of each segment 404, 406, 408 about tubular body 12. In other words, the angle, pitch, and/or spacing between windings that flexible body 102 helically winds about tubular body 12 may vary at each segment 404, 406, 408. For example, a pitch of helical wind of flexible body 102 may be relatively greater at distal segment 404 and proximal segment 408 than at intermediate segment 406. In this instance, flexible body 102 may be substantially flexible along distal segment 404 and proximal segment 408 relative to intermediate segment 406.

By way of further example, the pitch or angle that flexible body 102 helically winds about tubular body 12 may be relatively smaller along intermediate segment 406 such that flexible body 102 may be substantially rigid along intermediate segment 406. It should be appreciated that segments 404, 406, 408 may include various other angles and pitches of helical wrap than those shown and described herein, and relative to one another, than those shown and described herein dependent on a desired configuration of circuit device 400.

Still referring to FIG. 16, a direction of the helical wrap of flexible body 102 may change directions between one or more of the plurality of segments 404, 406, 408. In the present example, distal segment 404 and proximal segment 408 may be wound about tubular body 12 in a first direction A (e.g., clockwise direction) and intermediate segment 406 may wrap around tubular body 12 in a second direction B (e.g., counter clockwise direction) that is different than the first direction A. Further, distal segment 404 and/or proximal segment 408 may helically wind about tubular body 12 at a first helical pitch α and intermediate segment 406 may helically wind about tubular body 12 at a second helical pitch β that is different than first helical pitch α. For example, first helical pitch α may be relatively less than second helical pitch β such that distal segment 404 and/or proximal segment 408 may include fewer helical winds than intermediate segment 406. It should be appreciated that segments 404, 406, 408 may include various other helical pitches and/or winds relative to one another than those shown and described herein.

Circuit device 400 may be configured to form a gap 405 between adjacent segments 404, 406, 408 that change direction relative to one another when flexible body 102 is attached to tubular body 12. Circuit device 400 may not cover at least a portion of tubular body 12 when the helical wrap of flexible body 102 changes directions, thereby exposing a portion of tubular body 12 disposed beneath flexible body 102.

It should be appreciated that the flexural properties of tubular body 12 may vary along the portions that are exposed along gaps 405 relative to other portions that receive flexible body 102. For example, tubular body 12 may have a relatively decreased rigidity (i.e., an increased flexibility) along regions that omit flexible body 102 thereon. Further, an assembly of medical device 10 and circuit device 100 may provide areas having a greater material thickness along portions where flexible body 102 is attached to tubular body 12, thereby providing asymmetric properties along the longitudinal length of tubular body 12.

Still referring to FIG. 16, one or more features of medical device 10 on tubular body 12 (e.g., access holes 18) may be revealed and accessible along gap 405 when flexible body 102 is wound about tubular body 12. A size of gap 405 may vary and may be dependent on, for example, the angle of the helical wrap between the adjacent pair of segments defining gap 405. Access holes 18 may be in fluid communication with one or more lumens 11 (FIG. 6) such that a fluid and/or a device (e.g. a guidewire) may be delivered outwardly from tubular body 12 and/or a received into tubular body 12 via access holes 18. In some examples, access holes 18 may provide sensing portals to allow a device (e.g., fiber optic sensor, etc.) to measure one or more parameters, such as, for example, oxygen levels of a fluid (e.g., blood, etc.), central venous pressure, and more. Further, access holes 18 may provide deployment portals that allow one or more instruments to extend externally from tubular body 12. Although not shown, in some embodiments, access holes 18 may facilitate deployment of a Nitinol positioning device from tubular body 12 for contacting a vessel wall, thereby biasing tubular body 12 to a preferred configuration and stabilizing medical device 10 relative to a target treatment site.

It should be appreciated that an angle and/or a pitch of helical wrap of each the plurality of segments 404, 406, 408 may remain constant and/or vary relative to one another when a direction of the helical wind changes. In some embodiments, bend 410 may match an angle of the helical wrap of flexible body 102. In this instance, at least one of the plurality of segments 404, 406, 408 may have an elongated length extending along a longitudinal axis that is transverse to the remaining segments of flexible body 102.

Figure 17:
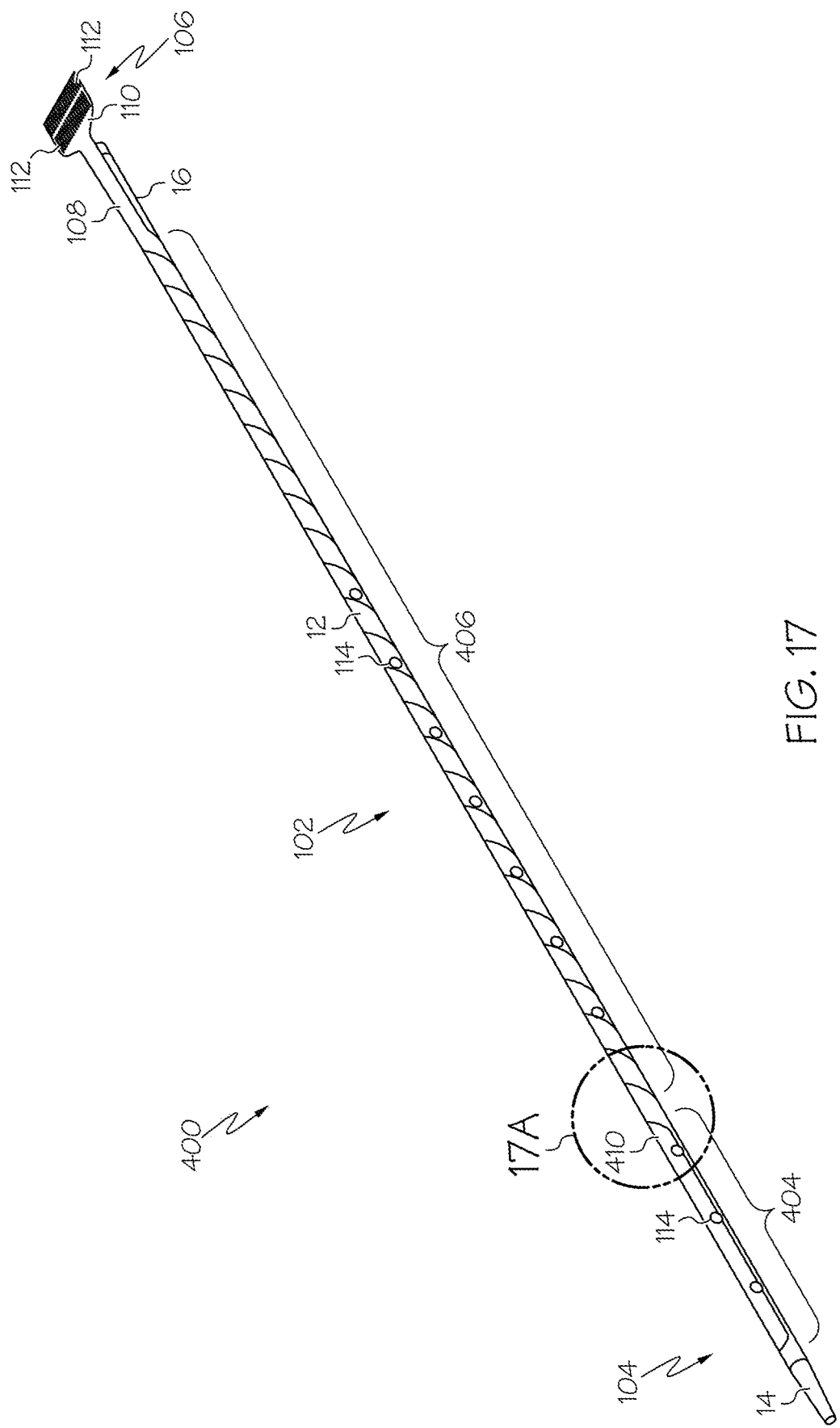
FIG. 17 illustrates a perspective view of another exemplary circuit device attached to the medical device of FIG. 3 and including a distal segment extending parallel to the medical device, according to one or more embodiments of the present disclosure.

For example, as seen in FIG. 17, distal segment 404 may extend parallel to a central axis of tubular body 12 when circuit device 400 is secured to medical device 10, and an angular change at bend 410 between distal segment 404 and intermediate segment 406 may be determinative of an angle of the helical wrap of flexible body 102 about tubular body 12. Stated differently, an angle of bend 410 may define, or correspond to, a helix angle of flexible body 102 wrapping about the central axis of tubular body 12.

As seen in FIG. 17A, bend 410 may define a bend angle C between distal segment 404 of flexible body 102 and intermediate segment 406. In some embodiments, bend angle C may range from about 1 degree to about 179 degrees, and may at least partially define a configuration of the plurality of helical winds (of flexible body 102) relative to tubular body 12. For example, relative to an axis T that is transverse to a central axis L of tubular body 12, the plurality of helical winds along intermediate segment 406 may include a helix angle D. Helix angle D may have a relationship relative to bend angle C such that bend angle C may be substantially equal to helix angle D plus about 90 degrees, when distal segment 404 is aligned with, or substantially parallel to, axis of tubular body 12, (C=D+90 degrees).

It should be understood that bend angle C and helix angle D of the present example are merely illustrative such that bend 410 and the plurality of helical winds along intermediate segment 406 may have various other suitable relationships relative to one another than those shown and described herein. Additionally, a helical pitch of intermediate segment 406 (e.g., see FIG. 16, first helical a, second helical pitch (3, etc.) may be at least partially defined by, or otherwise correspond to, bend angle C and/or helix angle D of flexible body 102. Thus, intermediate segment 406 may be wrapped in a helical configuration about tubular body 12. In the present example, circuit device 400 only includes a single bend 410 such that intermediate segment 406 extends to and terminates at bend 108.

Flexible body 102, and the portion of the medical device corresponding to it, may have varying flexural properties along distal segment 404 and intermediate segment 406 based on a respective geometry of each segment 404, 406. In the present example, distal segment 404 may be oriented parallel to a central axis of tubular body 12 such that the portion of the medical device corresponding to it distal segment 104 may have radial asymmetric flexural properties. Medical device 10 may experience greater deflection along a portion corresponding to distal segment 404 when a force that is transverse to a longitudinal axis of flexible body 102 and parallel to a central axis of tubular body 12 is applied, than when the force is perpendicular to both flexible body 102 and tubular body 12.

Still referring to FIG. 17, a radial flexural asymmetry of distal segment 404 may provide a greater rigidity on tubular body 12, such as, for example, in a specific direction when tubular body 12 is bent during use in a procedure. For example, a distal portion of tubular body 12 may be bent in one of a plurality of directions relative to a target treatment site, such as, for example, to contact a vessel wall within a subject. The distal portion of tubular body 12 may maintain contact with the vessel wall due to an enhanced rigidity of the distal portion provided by the radial flexural asymmetry of distal segment 404. In contrast to the radial asymmetric flexural properties of distal segment 404, intermediate segment 406 may have radial symmetric flexural properties based on the geometry of intermediate segment 406.

Figure 18:
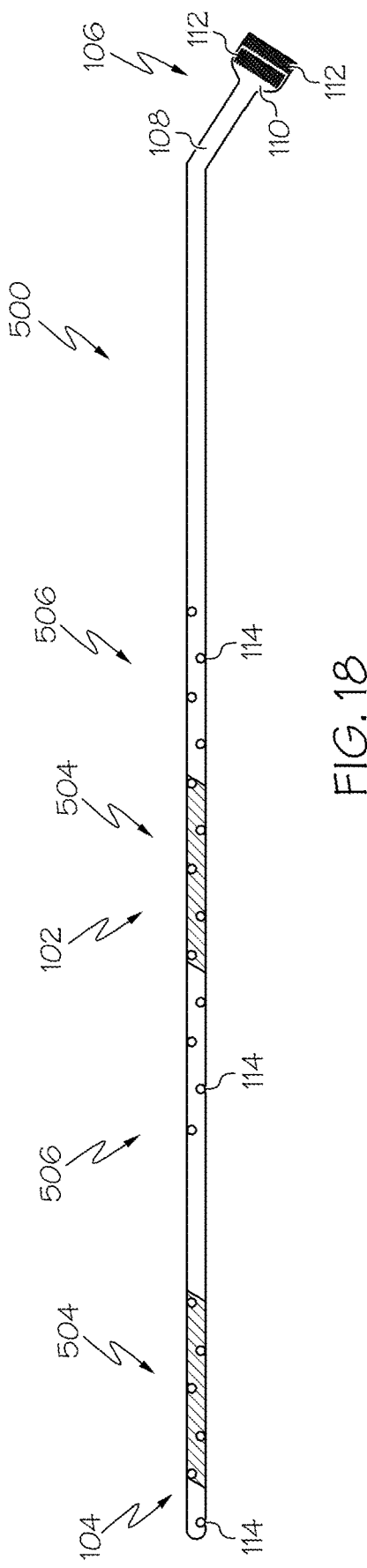
FIG. 18 illustrates a side view of another exemplary circuit device including a series of stiffener mechanisms, according to one or more embodiments of the present disclosure.

Referring now to FIG. 18, another exemplary circuit device 500 is shown in accordance with an example of this disclosure. Circuit device 500 may include one or more segments 504 having a stiffening structure formed therein, and one or more segments 506 omitting a stiffening structure. In the present example, circuit device 500 may include a pair of stiffened segments 504 and a pair non-stiffened segments 506 positioned between distal end 104 and proximal end 106. Stiffened segments 504 alternate with non-stiffened segments 506 along the length of circuit device 500. In other embodiments, circuit device 500 may include additional and/or fewer segments 504, 506 along flexible body 102 in various other suitable arrangements than those shown and described herein.

The stiffening structures may include components (e.g., additional layers, adhesive used for lamination, stiffening wires, etc.) made of materials of varying stiffness and/or thickness and that may be incorporated into regions of flexible body 102 to increase and/or decrease a stiffness of circuit device 500. Stiffeners may include glass-reinforced epoxy laminate materials (FR4), polyimide, polyester, polymers, and/or stainless steel. The stiffening structures may be formed of materials having a relatively high stiffness to increase a rigidity of tubular body 12 in the specific areas aligned with stiffening segments 504 when flexible body 102 is attached thereto.

Stated differently, flexible body 102 may be configured to reduce a flexibility of tubular body 12 along areas aligned with stiffening segments 504. The stiffening structures may provide additional layers on tubular body 12, thereby varying a width of the assembly of medical device 10 and circuit device 500 along a longitudinal length of tubular body 12. Accordingly, the flexural properties of tubular body 12 may vary at the selective regions corresponding to a location of stiffened segments 504 thereon. In other embodiments, a stiffening structure may be disposed between an exterior surface of tubular body 12 and interior surface 103 of flexible body 102 prior to attaching circuit device 100 to medical device 10. In this instance, the stiffening structure may be encapsulated between tubular body 12 and flexible body 102.

Figure 19:
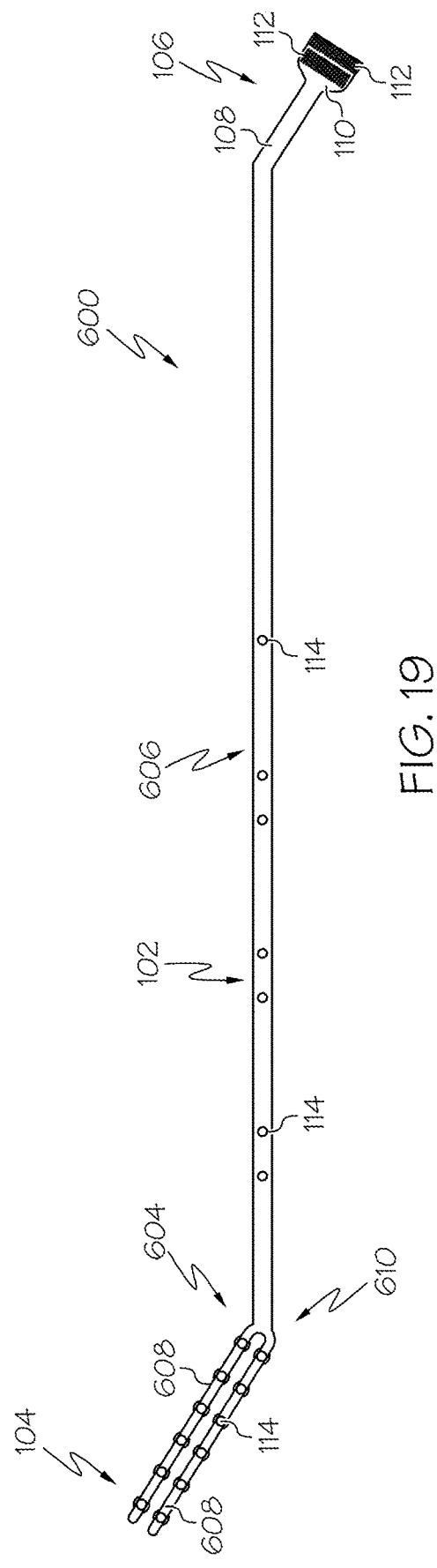
FIG. 19 illustrates a side view of another exemplary circuit device including an angled distal segment formed of a pair of branches, according to one or more embodiments of the present disclosure.

Referring now to FIG. 19, another exemplary circuit device 600 is shown in accordance with an example of this disclosure. Circuit device 600 may include a distal segment 604 and an intermediate segment 606 defining a longitudinal length of flexible body 102 between distal end 104 and proximal end 106. Distal segment 604 may include a pair of branch segments 608 extending distally from intermediate segment 606 such that distal end 104 may be defined by the pair of branch segments 608. Each branch segment 608 may be in parallel alignment with one another and may have a longitudinal length that is equal to, greater than, and/or less than one another. In the present example, branch segments 608 may have a substantially similar length that is less than a longitudinal length of intermediate segment 606. Each of branch segments 608 may have a width that is relatively less than a width of intermediate segment 606.

Still referring to FIG. 19, flexible body 102 may further include a bend 610 at a proximal end of the pair of branch segments 608 such that branch segments 608 may be angled relative to intermediate segment 606. Thus, each branch segment 608 may have a longitudinal axis that is transverse to an axis of intermediate segment 606. In some examples, an angular change of flexible body 102 at bend 610 may be determinative of an angle of a helical wrap of intermediate segment 606 about tubular body 12 when circuit device 600 is secured to medical device 10 (see, e.g., FIG. 17A, bend angle C).

Distal segment 604 and/or intermediate segment 606 may include one or more (e.g., a plurality) of electrodes 114. In the present example, each of the pair of branch segments 608 may define an array of electrodes 114 along distal segment 604, thereby providing a complex circuit density at distal segment 604. It should be appreciated that circuit device 600 may be configured to generate greater current and/or fields of coverage with the array of electrodes 114 on branch segments 608 for providing enhanced treatment therapies to a target site. The array of electrodes 114 may provide medical device 10 with complex electrode geometries capable of selectively generating greater current densities and/or concentrated density fields.

Circuit device 600 may be assembled onto medical device 10 such that the longitudinal axis of each branch segment 608 may be parallel to a center, longitudinal axis of tubular body 12. Stated differently, distal segment 604 may be secured onto a distal portion of tubular body 12 in a linear arrangement such that branch segments 608 extend parallel to the center axis of tubular body 12. Further, an axis of intermediate segment 606 may be transverse to the center axis of tubular body 12 such that flexible body 102 may be helically wound about an exterior of tubular body 12 along intermediate segment 606. Accordingly, circuit device 600 may be configured to impart different flexural properties onto tubular body 12 along a portion receiving distal segment 604 and intermediate segment 606, respectively.

Still referring to FIG. 19, branch segments 608 may be spaced apart from one another by an angle and/or distance when flexible body 102 is mounted onto tubular body 12. For example, each branch segment 608 may be positioned about 180 degrees apart from another when secured to a distal portion of tubular body 12. Thus, circuit device 600 may be configured to provide a pair of opposing electrode arrays that are offset from one another and positioned about a circumference of tubular body 12. For example, branch segments 608 may be positioned along a top and bottom (e.g., or a left and right) exterior surface of tubular body 12 when circuit device 600 is attached to medical device 10.

It should be appreciated that branch segments 608 may be selectively spaced apart from one another at various other relative degrees and/or distances dependent on a desired therapeutic effect to be provided by circuit device 600 and medical device 10. In other embodiments, circuit device 600 may include additional branch segments 608 at distal segment 604, intermediate segment 606, and/or at various other portions of flexible body 102.

Figure 20:
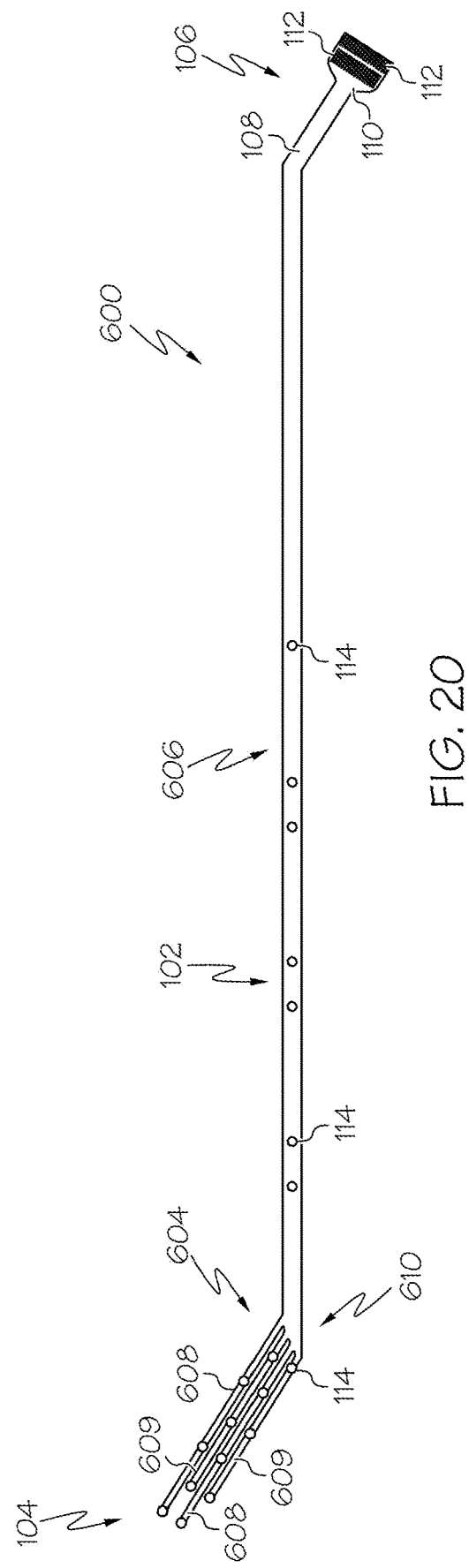
FIG. 20 illustrates a side view of another exemplary circuit device including an angled distal segment formed of a plurality of branches, according to one or more embodiments of the present disclosure.

For example, as shown in FIG. 20, circuit device 600 may include a second pair of branch segments 609 extending distally from intermediate section 606 and angled relative thereto by bend 610. In the present example, the pair of branch segments 609 may extend parallel to branch segments 608 and may have a longitudinal length that is equal to, greater than, and/or less than a longitudinal length of branch segments 608. In the example, branch segments 609 may have a smaller length than branch segments 608 and may be positioned in an alternating configuration with branch segments 608. Thus, each branch segment 608 may be separated from one another by at least one branch segment 609 positioned therebetween.

Each branch segment 609 may include one or more (e.g., a plurality) of electrodes 114, thereby defining an array of electrodes 114 on each branch segment 609. In some examples, electrodes 114 may be arranged along each branch segment 609 to be longitudinally aligned with one another, and longitudinally offset from the plurality of electrodes 114 along branch segments 608.

Still referring to FIG. 20, branch segments 609 may be spaced apart from one another, and/or from branch segments 608, by an angle and/or distance when flexible body 102 is mounted onto tubular body 12. For example, each branch segment 609 may be positioned about 180 degrees from one another and about 90 degrees from each branch segment 608 when secured to a distal portion of tubular body 12. Thus, circuit device 600 may provide two pairs of opposing electrode arrays that are offset from one another and positioned about a circumference of tubular body 12.

Figure 21:
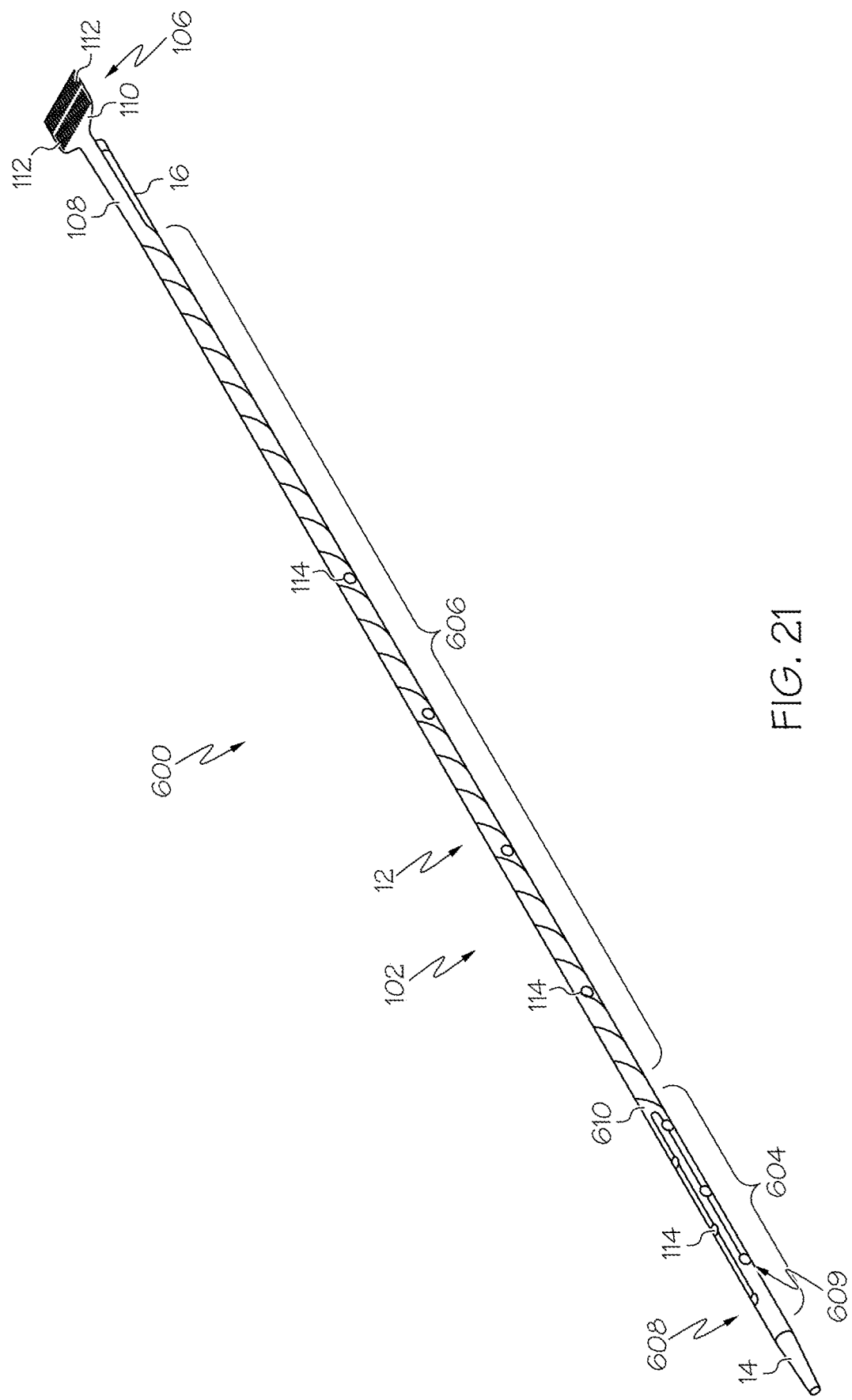
FIG. 21 illustrates a perspective view of the circuit device of FIG. 20 attached to the medical device of FIG. 3, according to one or more embodiments of the present disclosure.

For example, FIG. 21 shows branch segments 608 positioned along a top and bottom exterior surface of tubular body 12 (only the top can be seen in the Figure), and branch segments 609 positioned along a left and right side surface (only the left side can be seen in the Figure) when circuit device 600 is attached to medical device 10. It should be understood that branch segments 608 are spaced apart from one another by 180 degrees on tubular body 12 and branch segments 609 are spaced apart from one another by 180 degrees. Further, each branch segment 608 is positioned apart from branch segment 609 by 90 degrees on tubular body 12. In other embodiments, circuit device 600 may include additional and/or fewer branch segments 608, 609 at distal segment 604, intermediate segment 606, and/or at various other portions of flexible body 102.

Referring now to FIG. 22, an exemplary circuit device 700 is schematically depicted in accordance with another example of this disclosure. Circuit device 700 may include flexible body 102 having a longitudinal length defined by a distal segment 702, a first intermediate segment 704, a second intermediate segment 706, and a proximal segment 708. Distal segment 702 may terminate at distal end 104 and extend distally relative to first intermediate segment 704. Distal segment 702 may include the pair of branch segments 608 extending at an angle relative to first intermediate segment 702 by a bend 710.

First intermediate segment 704 may extend distally relative to second intermediate segment 706 such that first intermediate segment 704 may be disposed between distal segment 702 and second intermediate segment 706. First intermediate segment 704 may have a longitudinal length (an axis) extending transverse to the longitudinal axes of each of distal segment 702 and second intermediate segment 706. In some examples, first intermediate segment 704 may include one or more (e.g., a plurality) of electrodes 114; while in other examples, first intermediate segment 704 may exclude electrodes 114 thereon.

Still referring to FIG. 22, flexible body 102 may further include a second bend 712 between first intermediate segment 704 and second intermediate segment 706 such that first intermediate segment 704 may be configured to extend at an angle relative to second intermediate segment 706 by bend 712. Second intermediate segment 706 may include the pair of branch segments 609, with first intermediate segment 704 extending distally from a distal end of at least one of the pair of branch segments 609. Stated differently, each branch segment 608, 609 has a free distal end except for at least one of branch segments 609 which is secured to a proximal end of first intermediate segment 704.

Accordingly, the pair of branch segments 609 may be positioned proximal to, and at angle from, the pair of branch segments 608. Thus, each branch segment 609 may have a longitudinal axis that is transverse to an axis of the pair of branch segments 608. Second intermediate segment 706 may extend distally relative to proximal intermediate segment 708 such that second intermediate segment 706 may be disposed between first intermediate segment 704 and proximal segment 708. Second intermediate segment 706 may have a longitudinal length (an axis) extending transverse to a longitudinal axis of each of first intermediate segment 704 and proximal segment 708. In some examples, first intermediate segment 704 may have an axis that is parallel to an axis of proximal segment 708.

Still referring to FIG. 22, second intermediate segment 706 may include one or more (e.g., a plurality) of electrodes 114 on one or more of the pair of branch segments 609; while in other examples, second intermediate segment 706 may exclude electrodes 114 entirely. Flexible body 102 may include a bend 714 between second intermediate segment 706 and proximal segment 708 such that second intermediate segment 706 may be configured to extend at an angle relative to proximal segment 708 by bend 714.

Distal segment 702 and second intermediate segment 706 may extend parallel to each other and to a central longitudinal axis of tubular body 12, and first intermediate segment 704 and proximal segment 708 may be helically wrapped about tubular body 12, when circuit device 700 is attached to medical device 10. Accordingly, varying flexural properties may be imparted on tubular body 12 along those portions receiving segments 702, 706 thereon compared to segments 704, 708.

The pair of branches 608 may be secured to tubular body 12 along a similar or different radial location about the axis of body 12 than the pair of branches 609 (i.e., either spaced 180 degrees or 90 degrees apart, respectively, or any other suitable angle apart). An angular change of flexible body 102 at bends 710, 712, 714 may be determinative of an angle of a helical wrap of first intermediate segment 704 and proximal segment 708 about tubular body 12 when circuit device 700 is secured to medical device 10 (see, e.g., FIG. 17A, bend angle C). Accordingly, one or more gaps may be formed between branch segments 608 and branch segments 609.

Referring now to FIG. 23, an exemplary circuit device 800 is schematically depicted in accordance with another example of this disclosure. Circuit device 800 may include an alternative exemplary proximal tab 110" at proximal end 106. Proximal tab 110" may include a rectangular shape having one or more (e.g. a plurality) conductive pads 112 positioned thereon. In the example, proximal tab 110" may define a connector interface of circuit device 800 for connection with a power source (not shown). Stated differently, proximal tab 110" may be configured to directly connect with a power source in lieu of the circuit device establishing connection with the power source via one or more wires 118 (FIGS. 8-9).

Figure 24:
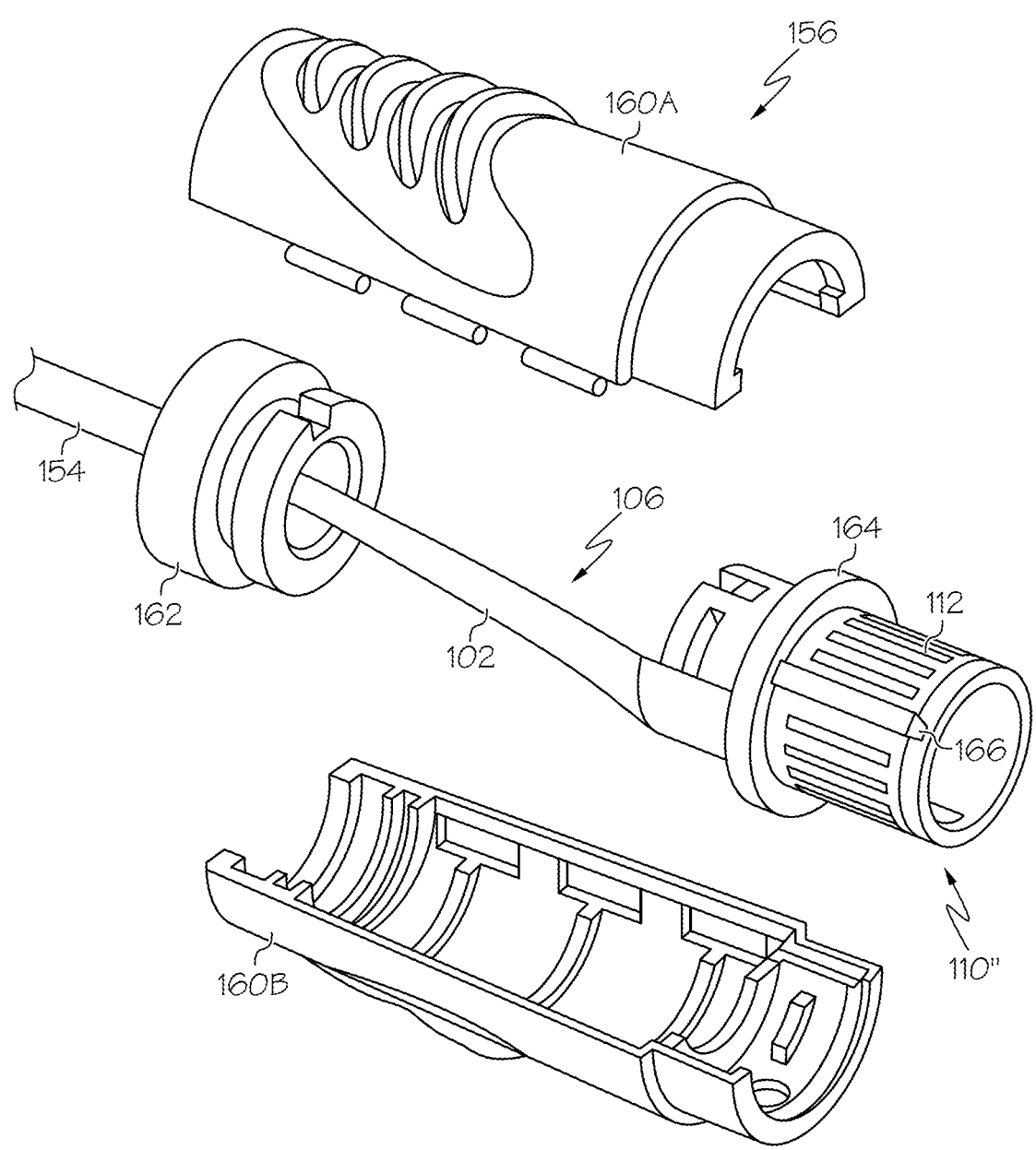
FIG. 24 illustrates a perspective view of the circuit device of FIG. 23 with the electrical circuit received within a connector assembly, according to one or more embodiments of the present disclosure.

FIG. 24 shows electrical connector 156 in a disassembled state for illustrative purposes. As shown, flexible body 102 may be received within electrical connector 156 via protective sheath 154. In the example, protective sheath 154 may be secured to electrical connector 156 at an inlet port 162 of electrical connector 156. Further, electrical connector 156 may include a top housing 160A and a bottom housing 160B defining an interior cavity for receiving proximal end 106. In the example, electrical connector 156 may include an outlet connector 164 in lieu of socket 158 and pins 159 (see FIG. 11).

Outlet connector 164 may extend proximally outward from housings 160A, 160B when electrical connector 156 is in a fully assembled state. Outlet connector 164 may define a connector interface of electrical connector 156 for connection with a power source and may be configured to receive proximal tab 110". Proximal tab 110" may be disposed about an exterior of outlet connector 164 with the plurality of conductive pads 112 facing radially outward. Outlet connector 164 may include a keying feature 166 configured to facilitate an alignment and attachment of proximal tab 110" to outlet connector 164. For example, keying feature 166 may engage the terminal ends of proximal tab 110" and/or designate a starting and ending point for wrapping proximal tab 110" about a circumference of outlet connector 164.

Still referring to FIG. 24, proximal tab 110" may be secured to outlet connector 164 by various suitable mechanisms, including, for example, by an adhesive. In exemplary use, conductive pads 112 may be exposed from housings 160A, 160B when proximal end 106 is received within electrical connector 156 and proximal tab 110" is secured to outlet connector 164. Conductive pads 112 may connect directly to the power source when electrical connector 156 is coupled thereto and outlet connector 164 is received within the power source, thereby providing electrical power to circuit device 800.

Each of the aforementioned systems, devices, assemblies, and methods may be used to provide electrical circuitry at a target treatment site in a subject (e.g., a patient) that may be capable of providing diagnostic or therapeutic effects. By providing a medical device including a circuit device disposed at the exterior of the medical device (over the sheath or tube), a user may utilize the lumens of the medical device for receipt of others devices and/or materials. With the circuit device having a minimal size and flexible electrical circuitry, the circuit device may minimize an overall physical profile of the medical device while maximizing a selective positioning of the electrical components at various locations along the medical device. In this instance, a user may increase efficiency of procedures, reduce overall procedure time, and/or avoid unnecessary harm to a subject's body caused by the medical device having an invasive profile for accommodating electrical circuitry devices within the lumens.

It will be apparent to those skilled in the art that various modifications and variations may be made in the disclosed devices and methods without departing from the scope of this disclosure. Other aspects of the disclosure will be apparent to those skilled in the art from consideration of eth specification and practice of the features disclosed herein. It is intended that the specification and examples be considered as exemplary only.

What is claimed is:

1. A medical device comprising:
    a flexible body having a proximal end and a distal end;
    an electrode positioned on the body proximate the distal end, wherein the electrode is configured to provide an electrical charge for stimulating tissue;
    an electrical connection positioned on the body proximate the proximal end, wherein the electrical connection is configured to electrically couple the electrode to a power source; and
    an electrical lead connecting the electrode to the electrical connection, wherein the lead is on or in the flexible body,
    wherein the body is configured to have a first configuration prior to being secured to an exterior of a tube and a second configuration having a shape that conforms to a profile of the tube with the electrode secured to an exterior of the tube; and
    wherein the flexible body, in the first configuration, includes at least one bend between the proximal end and the distal end, and the at least one bend causes a change in a pitch of a helical wind of the flexible body about the tube, when the flexible body is in the second configuration.

2. The medical device of claim 1, further comprising the tube, wherein the flexible body is helically wound about the exterior of the tube in a plurality of winds, to achieve the second configuration.

3. The medical device of claim 1, further comprising the tube, and securing the flexible body about the exterior of the tube causes the tube to have regions of varying flexibility at locations of the tube having the flexible body.

4. The medical device of claim 1, wherein the flexible body includes a dielectric substrate film disposed between the electrode and the electrical lead.

5. The medical device of claim 4, wherein the flexible body further includes a hole through the dielectric substrate film, and the hole is filled with a conductive material electrically connecting the electrode to the electrical lead.

6. The medical device of claim 4, further including a sensor, an electronic chip, or an integrated circuit disposed within the dielectric substrate film and between the electrode and the electrical lead.

7. The medical device of claim 1, wherein the flexible body, in the first configuration, includes at least one segment having an enlarged width relative to an adjacent portion of the flexible body, wherein the at least one segment is less flexible than the adjacent portion of the flexible body.

8. The medical device of claim 1, wherein the flexible body, in the first configuration, includes at least one segment having a nonlinear configuration adjacent to a portion of the flexible body having a linear configuration, wherein the at least one segment is more flexible than the portion.

9. The medical device of claim 1, further comprising the tube, wherein a longitudinal axis of a proximal portion of the flexible body, proximal to the bend, is transverse to a longitudinal axis of a distal portion of the flexible body, distal to the bend; and
    wherein a flexibility of a segment of the medical device having the proximal portion differs from a flexibility of a segment of the medical device having the distal portion, due to the arrangements of the proximal and distal portions on the tube.

10. The medical device of claim 1, wherein the flexible body includes at least one segment having a stiffening structure that is configured to increase a stiffness of the flexible body relative to an adjacent portion of the flexible body.

11. The medical device of claim 1, wherein the flexible body includes at least one segment at the distal end having a plurality of branches, wherein each of the plurality of branches includes an array of electrodes.

12. The medical device of claim 11, wherein the at least one segment is angled relative to the proximal end such that such that a longitudinal axis of the plurality of branches is transverse to a longitudinal axis of the flexible body.

13. The medical device of claim 11, wherein the flexible body includes a second segment proximal of the distal end and having a plurality of second branches, wherein each of the plurality of second branches includes a second array of electrodes.

14. A medical device comprising:
a tube having a longitudinal length and at least one lumen, wherein the tube is configured to receive at least one of a device and a fluid in the at least one lumen;
a flexible body having a stimulation array configured to provide an electrical charge for stimulating tissue, wherein the flexible body includes a proximal portion and a distal portion separated from the proximal portion by at least one bend;
wherein the flexible body is configured to cover at least a portion of the longitudinal length of the tube such that the stimulation array is disposed about an exterior of the tubular body; and
wherein the at least one bend is configured to arrange one of the proximal portion and the distal portion in a linear configuration and the other of the proximal portion and the distal portion in a nonlinear configuration relative to the tube, when the flexible body is wound about the exterior of the tube.

15. The medical device of claim 14, wherein the stimulation array includes
a distal electrode array positioned on the flexible body proximate to the distal portion, wherein the distal electrode array is configured to provide the electrical charge for stimulating tissue at a first location;
a proximal electrode array positioned on the flexible body proximate to the proximal portion, wherein the proximal electrode array is configured to provide the electrical charge for stimulating tissue at a second location that is different than the first location; and
an electrical connection positioned on the flexible body proximate to the proximal portion and configured to electrically couple the distal electrode array and the proximal electrode array to a power source.

16. The medical device of claim 14, wherein the at least one bend causes a change in direction of a helical wind of the flexible body about the tube, and a longitudinal axis of the proximal portion proximal to the at least one bend is transverse to a longitudinal axis of the distal portion distal to the at least one bend.

17. The medical device of claim 14, wherein a flexibility of a portion of the medical device having the proximal portion differs from a flexibility of a portion of the medical device having the distal portion, due to the arrangements of the proximal portion and distal portion on the tube.

18. A medical device comprising:
a tube; and
a circuit having a flexible body including a proximal portion and a distal portion that is angled relative to the proximal portion, the distal portion having a plurality of branches each including an array of electrodes configured to provide an electrical charge for stimulating tissue;
wherein the flexible body is configured to engage the tube with the proximal portion disposed over the tube in a helical configuration, and the distal portion is disposed over the tube in a linear configuration, such that the plurality of branches is arranged substantially parallel to a longitudinal axis of the tube.

19. The system of claim 18, wherein the plurality of branches are positioned about a circumference of the tube at spaced intervals; and
wherein the circuit is configured to modify a flexibility of the tube when the flexible body engages the tube, with the flexibility varying between a segment of the tube having the proximal portion and a segment of the tube having the distal portion.

20. The system of claim 18, wherein the circuit includes a conductive lead, a conductive layer, and a via connecting the conductive lead to the conductive layer.

* * * * *

UNITED STATES PATENT AND TRADEMARK OFFICE
CERTIFICATE OF CORRECTION

| | |
|---|---|
| PATENT NO. | : 11,771,900 B2 |
| APPLICATION NO. | : 16/898157 |
| DATED | : October 3, 2023 |
| INVENTOR(S) | : Viral S. Thakkar and Douglas G. Evans |

It is certified that error appears in the above-identified patent and that said Letters Patent is hereby corrected as shown below:

In the Claims

Claim 12, Column 28, Lines 65-66, delete "such that such that" and insert -- such that --.

Signed and Sealed this
Twenty-seventh Day of February, 2024

Katherine Kelly Vidal
Director of the United States Patent and Trademark Office